United States Patent
Yoshikawa et al.

(10) Patent No.: US 7,794,711 B2
(45) Date of Patent: Sep. 14, 2010

(54) AGENT FOR TREATING CHONDROMA AND CHONDROSARCOMA

(75) Inventors: Hideki Yoshikawa, Osaka (JP); Takahiro Miyaji, Osaka (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 233 days.

(21) Appl. No.: 10/533,584

(22) PCT Filed: Aug. 22, 2003

(86) PCT No.: PCT/JP03/10627

§ 371 (c)(1), (2), (4) Date: May 3, 2005

(87) PCT Pub. No.: WO2004/045643

PCT Pub. Date: Jun. 3, 2004

(65) Prior Publication Data

US 2007/0053905 A1    Mar. 8, 2007

(30) Foreign Application Priority Data

Nov. 18, 2002    (JP) ............................. 2002-334081

(51) Int. Cl.
*A61K 39/395*    (2006.01)

(52) U.S. Cl. .................. 424/130.1; 530/387.1

(58) Field of Classification Search ........................ None
See application file for complete search history.

(56) References Cited

U.S. PATENT DOCUMENTS 6,903,194 B1    6/2005    Sato et al.

2004/0001824 A1 *    1/2004    Yoshida et al. ........... 424/141.1

FOREIGN PATENT DOCUMENTS

EP    1 283 057    2/2003
WO    01/82968    11/2001

OTHER PUBLICATIONS

Zips et al. New anticancer agents: In vitro and In vivo evaluation. In Vivo. Jan.-Feb. 2005;19(1):1-7.*
Behar et al. (JBC, vol. 275(1), pp. 9-17, 2000).*
T. Miyaji et al., "Apoptosis Inducing effect and Differentiation Accelerating Effect on Chondrosarcoma Cell Line of Monoclonal Antibody to Parathyroid Hormone-Related Protein", Japan Journal of Cancer Research, Aug. 25, 2002, p. 174 with (English Translation).
M. Zenmyo et al., "p21 and Parathyroid Hormone-Related Peptide in the Growth Plate", Calcified Tissue International, vol. 67, No. 5, 2000, pp. 378-381.
T. Kunisada et al., "Co-Expression of Parathyroid Hormone-Related (PTHrP) and PTH/PTHrP Receptor in Cartilaginous Tumours: A Marker for Malignancy", Pathology, vol. 34, No. 2, 2002, pp. 133-137.

* cited by examiner

*Primary Examiner*—Larry R. Helms
*Assistant Examiner*—Meera Natarajan
(74) *Attorney, Agent, or Firm*—Wenderoth, Lind & Ponack, L.L.P.

(57) ABSTRACT

The present invention relates to a novel agent for treating chondroma and chondrosarcoma containing a substance which inhibits binding of parathyroid hormone related peptide to its receptor for improving the prognosis of chondroma or chondrosarcoma.

6 Claims, 7 Drawing Sheets

AGENT FOR TREATING CHONDROMA AND CHONDROSARCOMA

This application is a U.S. national stage of International Application No. PCT/JP2003/010627 filed Aug. 22, 2003.

TECHNICAL FIELD

The present invention relates to an agent for treating chondroma and chondrosarcoma containing a substance which inhibits binding of parathyroid hormone related peptide (parathyroid hormone related protein (PTHrP)) to its receptor.

BACKGROUND ART

Parathyroid hormone related peptide (hereinafter referred to as "PTHrP") is a peptide discovered as a humoral factor produced by tumor cells in hypercalcemia in association with a malignant tumor. Further, PTHrP causes neoplastic hypercalcemia (Humoral hypercalcemia of malignancy; hereinafter referred to as "HHM") by promoting bone resorption by osteoclast and calcium reabsorption in renal tubules.

It has been reported that PTHrP is produced not only in various neoplastic tissues but also in a wide variety of normal tissues throughout ontogeny including skin, central nerves, womb, placenta, mammary gland during breastfeeding, thyroid gland, parathyroid gland, adrenal gland, liver, kidney and bladder (see, for example, Non-patent Documents 1 and 2).

PTHrP has physiological effects such as: control of differentiation and proliferation of cells, relaxation of smooth muscle, promotion of transplacental calcium transportation, promotion of apoptosis and causes clinical conditions such as hypercalcemia represented by HHM, hypophosphatemia. These effects of PTHrP are exhibited through the binding of PTHrP to PTH/PTHrP receptors mainly found in bone and kidney, which activates plural intracellular signaling systems.

Meanwhile, the present inventors have already reported that PTHrP controls differentiation of cartilage cells from pre-hypertrophy stage to hypertrophy stage. As for the differentiation regulation of cartilage cells, participation of feedback between intracellular signaling of PTHrP and Indian hedgehog is suggested, but the mechanism through which ATTACHMENT A PTHrP effects on bone formation has not yet been elucidated (see, for example, Non-patent Documents 3 and 4).

Many of the bones constituting the framework of a vertebrate animal are built by the ossification process called enchondral bone formation. In the enchondral bone formation, proliferated cartilage cells, while continuing differentiation, build an environment which facilitates bone to be formed, and finally they die and are replaced by bone. Apoptosis is proposed as a mechanism of the extinction of the cartilage cells in the enchondral bone formation (see, for example, Non-patent Documents 5 and 6).

Apoptosis is controlled by the expression ratio of cell death inhibiting factor Bcl-2 and cell death inducing factor Bax in some cell systems. That is, whether a cell will be alive or dead is determined by the ratio of Bcl-2 and Bax in the cell. It has been revealed recently that the Bcl-2 gene is located downstream of the PTHrP gene in the signaling path which controls maturity of cartilage cells and that PTHrP increases expression of Bcl-2 (see, for example, Non-patent Document 7).

Meanwhile, it has been reported that both the expressions of PTHrP and Bcl-2 are high in chondrosarcoma cells (see, for example, Non-patent Documents 8 and 9). Chondrosarcoma is a chondrogenetic malignant tumor and is the second most bone tumor after osteosarcoma. Because it has a bad response to chemotherapy or radiotherapy, it is chiefly treated by surgical excision. However, the prognosis of chondrosarcoma is not good in mesenchymal dedifferentiated chondrosarcoma in the grade III while it is comparatively good (65% of five-year probability of survival) in the case of Grades I and II. Accordingly, a new medical treatment method of improving the prognosis of chondrosarcoma is desired.

On the other hand, it is already known that the antibody to PTHrP (hereinafter referred to as "anti-PTHrP antibody") is useful for treating HHM or cachexia resulting from PTHrP (see, for example, Patent Document 1 and Non-patent Document 10) and preventing progress of bone metastasis of cancer. However, the effect of PTHrP on chondroma, chondrosarcoma and the like has not been scarcely clarified and in addition, there is no report until now indicating the use of PTHrP or anti-PTHrP antibody in the treatment of chondroma or chondrosarcoma.

Patent Document 1:
  JP Patent Publication (Kokai) No. 11-80025 A (1999)

Non-Patent Document 1:
  Burtis, W. J., Clin. Chem. 1992; 38: p 2171-2183

Non-Patent Document 2:
  Stewart, A. F. & Broadus, A. E. J., Clin. Endocrinol. 1991; 71: p 1410-1414

Non-Patent Document 3:
  Nakase T. et al., Histochem. Cell Biol. 2001; 116: p 277-284

Non-Patent Document 4:
  Suda N. et al., Oral Dis. 1997; 3: p 229-231

Non-Patent Document 5:
  Farnum C. E., et al., Am. J. Anat. 1989; 186: p 346-358

Non-Patent Document 6:
  Lewinson D. et al., Anat. Rec. 1992; 233: p 504-514

Non-Patent Document 7:
  Amling M., et al., J. Cell Biol. 1997; 136: p 205-213

Non-Patent Document 8:
  Amling M. et al., Verh. Dtsch. Ges. Pathol. 1998; 82: p 160-169

Non-Patent Document 9:
  Bovee J. V., et al., Lab. Invest. 2000; 80: p 1925-1934

Non-patent Document 10:
  Sato et al., J. bone & Mine. Res. 1993; 8: p 849-860

DISCLOSURE OF THE INVENTION

An object of the present invention is to provide a novel agent for treating chondroma and chondrosarcoma for improving the prognosis of chondroma or chondrosarcoma.

In order to attain the above-mentioned object, the present inventors have conducted intensive studies and come to the conclusion that if PTHrP is inhibited and the expression of Bcl-2 in chondrosarcoma cells is decreased, apoptosis of the cells will be induced and the treatment of chondrosarcoma will be enabled. Further, the present inventors have discovered that by using a substance which inhibits binding of PTHrP and its receptor, chondroma and chondrosarcoma can be effectively controlled, and thus completed the present invention.

That is, the present invention provides following (1) to (9):

(1) An agent for treating chondroma and chondrosarcoma containing a substance which inhibits binding of parathyroid hormone related peptide to a receptor thereof.

(2) The agent according to the above (1), wherein the substance is an antagonist of the parathyroid hormone related peptide receptor.

(3) The agent according to the above (1), wherein the substance is an anti-parathyroid hormone related peptide antibody.

(4) The agent according to the above (1), wherein the substance is a fragment and/or a modified antibody of an anti-parathyroid hormone related peptide antibody.

(5) The agent according to the above (3) or (4), wherein the antibody is a monoclonal antibody.

(6) The agent according to the above (3) or (4), wherein the antibody is a humanized or chimerized antibody.

(7) The agent according to the above (6), wherein the humanized antibody is a humanized #23-57-137-1 antibody (a humanized antibody produced by hybridoma clone #23-57-137-1 (internationally deposited as FERM BP-5631 on Aug. 15, 1996 under the Budapest Treaty with International Patent Organism Depositary, National Institute of Advanced Industrial Science and Technology, an Independent Administrative Institution, located at Tsukuba Central C; 1-1-1 Higashi, Tsukuba, Tbaraki, Japan)).

(8) A method of inducing apoptosis in chondroma and chondrosarcoma cells by administering a substance which inhibits binding of parathyroid hormone related peptide and a receptor thereof.

(9) The method according to the above (8), wherein the substance is an anti-parathyroid hormone related peptide antibody.

Hereinafter, the present invention will be described in detail.

1. Agent for Treating Chondroma and Chondrosarcoma

The present invention provides an agent for treating chondroma and chondrosarcoma containing a substance which inhibits binding of parathyroid hormone related peptide (parathyroid hormone related protein: PTHrP) and its receptor (PTHrP receptor) as an active ingredient.

The "chondroma and chondrosarcoma" mean a chondrogenetic benign or malignant tumor in this specification. The "chondroma" is a benign tumor generated from mesodermal cells to be differentiated into cartilage, and includes enchondroma generated from medullary cavity, extraskeletal chondroma generated in soft tissue and having no connection with the bone or periosteum beneath the tissue, periosteal chondroma generated from periosteum or connective tissue of periosteum, parosteal chondroma, etc. The "chondrosarcoma" is a malignant tumor originating from cartilage cells, and includes central chondrosarcoma generated in the central part of the bone, peripheral chondrosarcoma generated from the cartilage cap of osteochondroma, chondrosarcoma derived from undifferentiated cells of mesenchymal origin having cartilage differentiation ability, etc. Some chondrosarcomas shift from chondromas and therefore the boundary therebetween is sometimes not clear, and for this reason, they are collectively referred to as "chondroma and chondrosarcoma" in this specification.

In this specification, "PTHrP receptor" means a receptor which binds to PTHrP as is described, for example, in JP Patent Publication (Kohyo) No. 6-506598 A (1994), and does not discriminate whether or not the PTHrP receptor exists on a target organ (for example, bone or kidney).

The "substance which inhibits binding of PTHrP and a PTHrP receptor" means either one or both substances which bind to PTHrP and prevents the PTHrP from binding to a PTHrP receptor and a substance which binds to a PTHrP receptor and prevents PTHrP from binding to the PTHrP receptor. Examples of the substance which falls under the former category include an anti-PTHrP antibody and examples of the substance which falls under the latter category include an antagonist to a PTHrP receptor (also referred to as PTHrP antagonist).

The above-mentioned "anti-PTHrP antibody" may be of any origin, type (monoclonal or polyclonal) or form as long as it binds to PTHrP and inhibits disintegration of tissue. The anti-PTHrP antibody includes, for example, humanized antibody, human antibody (WO96/33735), chimeric antibody (JP Patent Publication (Kokai) No. 4-228089A (1992)), mouse antibody (for example, antibody produced by hybridoma #23-57-137-1 (#23-57-137-1 antibody)), etc. Although the antibody may be a polyclonal antibody or a monoclonal antibody, a monoclonal antibody is more preferable for the purpose of the present invention.

Although the above-mentioned "PTHrP antagonist" may be generally a polypeptide or a low molecule substance, it is not limited to these. The PTHrP antagonist includes, for example, polypeptides having PTHrP antagonist activity described in JP Patent Publication (Kokai) No. 7-165790A (1995), JP Patent Publication (Kohyo) No. 5-509098A (1993), Peptides (UNITED STATES) 1995, 16(6)1031-1037, Biochemistry (UNITED STATES) Apr. 281992, 31 (16) 4026-4033 etc. Polypeptides in which at least one amino acid is deleted, added, replaced or inserted are included in the PTHrP antagonist of the present invention as long as they function as a PTHrP antagonist.

Hereafter, an anti-PTHrP antibody is described as a suitable example of the "substance which inhibits binding of PTHrP and a PTHrP receptor" of the present invention.

1-1 Anti-PTHrP Antibody

The anti-PTHrP antibody used in the present invention can be obtained as a polyclonal or monoclonal antibody using well-known means. In the present invention, a mammal derived monoclonal antibody is the preferred anti-PTHrP antibody.

The above-mentioned mammal derived monoclonal antibody includes one produced by a hybridoma, and one produced by a host transformed with an expression vector which contains an antibody gene by a genetic engineering technique. These antibodies bind to PTHrP, thereby inhibiting PTHrP from binding to a PTH/PTHrP receptor, and can block signaling by PTHrP and inhibit biological activity of PTHrP.

Suitable examples of such an antibody include #23-57-137-1 antibody produced by hybridoma clone #23-57-137-1, for example.

The hybridoma clone #23-57-137-1 was internationally deposited as FERM BP-5631 on Aug. 15, 1996 under the Budapest Treaty with International Patent Organism Depositary, National Institute of Advanced Industrial Science and Technology, an Independent Administrative Institution, located at Tsukuba Central 6, 1-1-1 Higashi, Tsukuba, Ibaraki, Japan.

1-2 Antibody Producing Hybridoma

The hybridoma which produces a monoclonal antibody is prepared according to a usual method as follows. That is, PTHrP is used as a sensitizing antigen to immunize an animal such as a mouse, and the resultant immunized cell is fused with a well-known parent cell by usual cell fusion method, and monoclonal antibody producing hybridomas are screened.

The human PTHrP used as a sensitizing antigen for obtaining the antibody can be prepared based on the PTHrP gene/amino acid sequence disclosed in Suva, L. J. et al., Science (1987) 237, 893. That is, after inserting the gene sequence encoding the PTHrP into a well-known expression vector system to transform a suitable host cell, the target PTHrP protein is purified from the host cell or culture supernatant by a well-known method.

As a sensitizing antigen besides the above-mentioned PThrP protein, 34 peptides at N-end of PTHrP may be chemically synthesized and used.

Mammals to be immunized with a sensitizing antigen are not particularly limited and preferably selected in consideration of compatibility with the parent cell to be used for cell fusion. Typically rodent animals (for example, mouse, rat, hamster, etc.) or rabbit, monkey, etc. may be used.

The immunization of an animal with a sensitizing antigen is performed according to a well-known method. Examples of a general method include intraperitoneally or hypodermically injecting the sensitizing antigen to the mammal. Specifically, the sensitizing antigen is suitably diluted and suspended in PBS (Phosphate-Buffered Saline) or normal saline, etc., to which a suitable amount of usual adjuvant, for example, complete Freund's adjuvant is optionally added and emulsified, and then it is administered to a mammal a couple of times every 4 to 21 days. A suitable carrier may be used at the time of immunization with a sensitizing antigen.

The animal is thus immunized, and after the antibody level in the serum is confirmed to rise to a desired level, immunized cells are extracted from the animal and subjected to cell fusion, and particularly, preferable immunized cells include splenic cells.

An example of a parent cell would be another cell to be fused with the above-mentioned immunized cell. A mammalian myeloma cell is typically used as a parent cell. Various well-known cell lines are preferably used as the myeloma cell, for example, P3 (P3x63Ag8.653) (J. Immunol. (1979) 123, 1548-1550), P3x63Ag8U.1 (Current Topics in Microbiology and Immunology (1978) 81, 1-7), NS-1 (Kohler. G. and Milstein, C. Eur. J. Immunol. (1976) 6, 511-519), MPC-11 (Margulies. D. H. et al., Cell (1976) 8, 405-415), SP 2/0 (Shulman, M. et al., Nature (1978), 276, 269-270), FO (de St. Groth, S. F. et al., J. Immunol. Methods (1980) 35, 1-21), S194 (Trowbridge, I. S. J. Exp. Med. (1978) 148, 313-323), R210 (Galfre, G. et al., Nature (1979) 277, 131-133), etc.

The cell fusion of the above-mentioned immunized cell and a myeloma cell can be fundamentally performed according to a well-known method, for example, the method by Milstein et al. (Kohler. G. and Milstein, C., Methods Enzymol. (1981) 73, 3-46), etc.

The above-mentioned cell fusion is carried out, for example, in the presence of a cell fusion accelerator in a usual nutrient culture solution. As this fusion accelerator, polyethyleneglycol (PEG), Hemagglutinating Virus of Japan (HVJ), and etc. are used. For example, if desired, an auxiliary agent such as dimethylsulfoxide may be added and used in order to enhance fusion efficiency.

The ratio of the immunized cell and myeloma cell to be used can be arbitrarily set. Typically, the immunized cell is preferably used one to ten times to a myeloma cell. As a culture solution used for the above-mentioned cell fusion, RPMI1640 culture solution suitable for proliferation of the above-mentioned myeloma cell line, MEM culture solution, and the other usual culture solutions used for this kind of cell culturing can be used. Further, supplemental liquid to serum such as Fetal Bovine Serum (FCS) can be used together.

Cell fusion can be performed by thoroughly mixing the predetermined amounts of the above-mentioned immunized cells and the myeloma cells in the above-mentioned culture solution, and a PEG solution (for example, about 1000 to 6000 in average molecular weight) warmed beforehand at about 37° C. is added usually at a concentration of 30-60% (w/v) and mixed. Thereby, fusion cells (hybridomas) are formed. Next, a suitable culture solution is successively added thereto. Centrifugation to remove the supernatant is repeated to remove the cell fusion agent which is not preferable for the growth of hybridomas.

The thus obtained hybridoma is cultured for selection in a usual selection culture solution (culture solution containing hypoxanthine, aminopterin and thymidine), for example, HAT culture solution. The culturing in this HAT culture solution is continued for a sufficient period of time (usually several days to several weeks) so that the cells (non-fused cells) other than the hybridomas to be obtained may be annihilated. Subsequently, screening and single cloning of the hybridoma which produces the target antibody are performed using a traditional limiting dilution method.

As mentioned above, in addition to the method for obtaining a hybridoma by immunizing an non-human animal with PTHrP, a hybridoma which produces a human antigen having PTHrP binding activity can be obtained by sensitizing a human lymphocyte with PTHrP in vitro and fusing the obtained sensitized lymphocyte with a myeloma cell derived from human and having permanent division ability (see JP Patent Publication (Kokoku) No. 1-59878 B (1989)). In addition, PTHrP may be administered to a transgenic animal which has all the repertories of human antibody genes to obtain anti-PTHrP antibody producing cells and obtain a human antibody to PTHrP from the immortalized cells (see International Patent Publication Nos. WO94/25585, WO93/12227, WO92/03918 and WO94/02602).

The thus prepared hybridoma which produces the monoclonal antibody can be passaged in a usual culture solution and can also be stored in liquid nitrogen over a long period of time.

In order to obtain the monoclonal antibody from these hybridomas, a method in which such hybridomas are cultured according to a usual method to obtain the antibody from the culture supernatant is used. One can also administer hybridomas to a compatible mammal and proliferated to obtain the antibody from the ascitic fluid etc. The former method is suitable for obtaining highly pure antibody, while the latter method is suitable for mass production of an antibody.

1-3 Recombinant Antibody

In the present invention, recombinant antibody obtained by incorporating the antibody gene cloned from the hybridoma in a suitable vector and introducing and expressing it in a host can be used as a monoclonal antibody (see, for example, Vandamme, A. M. et al., Eur. J. Biochem. (1990) 192, 767-775, 1990).

Specifically, mRNA encoding the variable (V) domain of anti-PTHrP antibody is isolated from the hybridoma which produces the anti-PTHrP antibody. Isolation of mRNA can be performed using mRNA Purification Kit (Pharmacia) etc. from total RNA prepared by a well-known method. Well known methods include for example: guanidine ultracentrifugal method (Chirgwin, J. M. et al., Biochemistry (1979)18, 5294-5299), AGPC method (Chomczynski, P. et al., Anal.

Biochem. (1987) 162, 156-159), etc. The target mRNA can also be directly prepared by using QuickPrep mRNA Purification Kit (Pharmacia).

Next, cDNA of the V domain of the antibody is synthesized from the obtained mRNA using a reverse transcriptase. Synthesis of cDNA can be performed using AMV Reverse Transcriptase First-strand cDNA Synthesis Kit (Seikagaku Corporation) etc. In addition, synthesis and amplification of cDNA can be performed by 5'-RACE method (Frohman, M. A. et al., Proc. Natl. Acad. Sci. USA (1988)85, 8998-9002, Belyavsky, A. et al., Nucleic Acids Res. (1989) 17, 2919-2932) using 5'-Ampli FINDER RACE Kit (Clontech) and PCR, etc.

Furthermore, the target DNA fragment is purified from the obtained PCR product and ligated with a vector DNA. The thus prepared recombination vector is introduced into E. coli, etc. and the desired recombination vector is prepared from the generated colonies. The nucleotide sequence of the target DNA is confirmed by a well-known method, for example, dideoxynucleotide chain termination method etc.

Once the DNA encoding the V domain of the target anti-PTHrP antibody is obtained, it is incorporated into an expression vector containing DNA encoding the constant domain (C domain) of the desired antibody.

On this occasion, the above-mentioned antibody gene must be incorporated into an expression vector so that it may be appropriately expressed under the control of an expression control domain, for example, an enhancer and a promoter. The target antibody gene is expressed by transforming the host cell with this expression vector.

Expression of the antibody gene can be performed by incorporating a DNA encoding the heavy chain (H chain) or the light chain (L chain) of the antibody separately into expression vectors to simultaneously transform the host cell, or alternatively by incorporating a DNA encoding the H chain and the light chain L chain into a single expression vector to transform the host cell (see WO94/11523).

Not only the host cell mentioned above but a transgenic animal can be used for the production of a recombinant antibody. For example, an antibody gene is inserted in a gene encoding a protein inherently produced in milk (goat β casein etc.) to prepare a fusion gene. A DNA fragment containing the fusion gene in which this antibody gene has been inserted is injected into an embryo of a goat, and this embryo is introduced into a female goat. The desired antibody can be obtained from milk produced by a transgenic goat delivered by the goat having received the embryo or its posterity. In order to increase the milk production containing the desired antibody produced by the transgenic goat at this time, a suitable hormone may be used for the transgenic goat (Ebert, K. M. et al., Bio/Technology (1994)12, 699-702).

1-4 Modified Antibody (Chimeric Antibody, Humanized Antibody)

In the present invention, besides the above-mentioned antibody, recombinant antibodies artificially modified for the purpose of reducing heterologous antigenicity to human etc., for example, a chimeric antibody and a humanized antibody can be used. These modified antibodies can be manufactured using the following methods:

A chimeric antibody useful for the present invention can be obtained by ligating a DNA encoding the V domain of the antibody as mentioned above to a DNA encoding the C domain of human antibody, incorporating this into an expression vector, and introducing and expressing it in a host.

A humanized antibody is also referred to as a reshaped human antibody, and means an antibody in which the complementarity determination region (CDR; complementarity determining region) of a non-human mammal. For example, a mouse antibody, is transplanted to the complementarity determination region of a human antibody. The humanized antibody can be produced based on a common technique of recombination of genes (see Europe Patent Application Publication EP 125023 and WO96/02576).

Specifically, a DNA sequence designed for connecting the CDR of a mouse antibody and the framework region (FR) of a human antibody is amplified by PCR method using as primers some oligonucleotides prepared so that they may have a portion overlapping to the end regions of both the CDR and FR. The desired humanized antibody can be obtained by connecting the obtained DNA to a DNA encoding the C domain of a human antibody, incorporating it in an expression vector, and introducing and expressing it in a host (see EP239400 and WO96/02576).

As a framework region of the human antibody connected through the above CDR, a region is selected so that the CDR forms a good antigen binding site. If needed, the amino acid(s) in the framework region in the variable domain of the antibody may be replaced so that the complementarity determination region of the reshaped human antibody may form a suitable antigen binding site (Sato, K. et al., Cancer Res. (1993) 53, 851-856).

As the C domain of a chimeric antibody and a humanized antibody, those of a human antibody is used, and for example, Cγ1, Cγ2, Cγ3 or Cγ4 can be used in the H chain and CK and Ck in the L chain. In addition, in order to improve the stability of an antibody or the production thereof, the C domain of the human antibody may be suitably modified.

A chimeric antibody consists of a variable domain of an antibody derived from a mammal other than human and a constant domain derived from human. On the other hand, a humanized antibody consists of a complementarity determination region derived from a mammal other than human and the framework region and C domain derived from human. Since the humanized antibody has an reduced antigenecity in the human body, the humanized antibody is useful as an active ingredient of the inhibiting agent of the present invention.

As a humanized antibody which can be used in the present invention, humanized #23-57-137-1 antibody can be mentioned. The humanized #23-57-137-1 antibody is the complementarity determination region of #23-57-137-1 antibody derived from a mouse connected to three FR fragments (FR1, FR2 and FR3) derived from human antibody HSU03868 (GEN-BANK, Deftos M. et al., Scand. J. Immunol., 39, 95-103, 1994) and FR fragment (FR4) derived from human antibody S25755 (NBRF-PDB) for the L chain, and for the H chain, that connected to the framework region of human antibody S31679 (NBRF-PDB, Cuisinier A M et al., Eur. J. Immunol., 23, 110-118, 1993) and a part of amino acid residues in the framework region is replaced so that it may have antigen binding activity.

As for the E. coli which has a plasmid containing DNA encoding L chain or H chain of humanized #23-57-137-1 antibody, E. coli which has a plasmid containing DNA encoding the H chain (Escherichia coli JM109 (hMBC1 HcDNA/pUC19)) was internationally deposited as FERM BP-5629 and E. coli which has a plasmid containing DNA encoding the L chain (Escherichia coli JM109 (hMBC1Lqλ/pUC19)) was internationally deposited as FERM BP-5630, respectively on Aug. 15, 1996 under the Budapest Treaty with International Patent Organism Depositary, National Institute of Advanced Industrial Science and Technology, an Independent Administrative Institution, located at Tsukuba Central 6, 1-1-1 Higashi, Tsukuba, Ibaraki, Japan.

1-5 Modified Antibody

The antibody used in the present invention may be a fragment of an antibody or a modified substance thereof, as long as it binds with PTHrP and inhibits the activity of PTHrP. Examples of a fragment of an antibody include Fab, F(ab')$_2$, Fv, or a single chain Fv(scFv) in which Fv of H chain or L chain was linked with a suitable linker. This fragment may be formed by treating the antibody with an enzyme, for example, papain or pepsin or may be prepared by constructing a gene encoding an antibody fragment, and introducing this into an expression vector and expressing it in a suitable host cell (see, for example, Co, M. S. et al., and J. Immunol. (1994) 152, 2968-2976, Better, M. & Horwitz, A. H. Methods in Enzymology (1989) 178, 476-496, Academic Press, Inc., Plueckthun, A. & Skerra, A. Methods in Enzymology (1989) 178, 476-496, Academic Press, Inc., Lamoyi, E., Methods in Enzymology (1989) 121, 652-663, Rousseaux, J. et al., Methods in Enzymology (1989)121, 663-669, Bird, R. E. et al., TIBTECH (1991) 9, 132-137).

The above-mentioned scFv can be obtained by linking a V domain of H chain and a V domain of L chain of an antibody. In this scFv, the V domain of H chain and the V domain of L chain are linked with a linker, preferably with a peptide linker (Huston, J. S. et al., Proc. Natl. Acad. Sci. U.S.A. (1988) 85, 5879-5883). The V domain of H chain and the V domain of L chain in scFv may be derived from any one described in this specification as an antibody. As a peptide linker which joins V domains, any single chain peptide consisting of 12-19 amino acid residues, for example, can be used.

The DNA encoding the scFv is prepared using as a template, the whole sequence of the DNAs encoding the H chain or the V domain of the H chain of the above-mentioned antibody, and the L chain or the V domain of the L chain, or DNA portion encoding the desired amino acid sequences. That is, it can be obtained by carrying out PCR amplification using a primer pair which specifies the both ends of this sequence, and then by further amplifying using a primer pair so that DNA encoding a peptide linker portion being linked at its both ends respectively to the H chain and the L chain.

Once a DNA which encodes scFv is thus prepared, an expression vector containing the same and the host transformed with this expression vector can be obtained according to a usual method. And scFv can be obtained using this host according to a usual method.

In addition, as for the fragment of the above-mentioned antibody, a gene corresponding thereto can be obtained similarly, and the fragment can be produced from a host transformed with this. The "antibody" in the present invention also encompasses these antibody fragments.

The modified antibody can be obtained by subjecting the obtained antibody to a chemical modification. The modification method of such an antibody is already established in this field. Examples of the modified antibody include anti-PTHrP antibodies bound with various molecules such as polyethyleneglycol (PEG). The "antibody" in the present invention also encompasses these modified antibodies.

1-6 Expression and Production of Recombinant Antibody or Modified Antibody

Expression and production of the recombinant antibody or the modified antibody can be attained by expressing the antibody gene constructed as mentioned above according to a well-known method. In such an expression system, both eukaryotic and prokaryotic cell systems can be used.

Examples of the eucaryotic cell include animal cells such as an established mammal cell system, insect cell system, filamentous fungi and yeast cell, etc. Examples of the procaryotic cell include bacteria cells such as E. coli cell.

In the case of E. coli, plasmids derived from E. coli (pBR322, pBR325, pUC18, pUC119, pTrcHis, pBlueBacHis, etc.), λ phage, etc. can be used for example as a vector for the introduction and expression of the target gene.

For the expression of the gene in E. coli, a useful promoter regularly used, a signal sequence for the antibody secretion and the antibody gene to be expressed should be functionally linked. Examples of the promoter include lacz promoter and araB promoter. The expression can be effected according to the method by Ward et al. (Nature (1098)341, 544-546; FASEB J. (1992) 6, 2422-2427) when the lacz promoter is used, or according to the method by Better et al. (Science (1988)240, 1041-1043) when the araB promoter is used.

As a signal sequence for antibody secretion, pelB signal sequence (Lei, S. P. et al. J. Bacteriol. (1987) 169, 4379) may be used, if it is the case where it is produced by periplasm of E. coli. The antibody produced by periplasm is separated and then used by appropriately refolding the structure of the antibody.

In addition, the expression vector can include a selection marker if needed. Examples of the selection marker include dihydrofolate reductase gene and drug resistance genes such as ampicillin resistance gene, neomycin resistance gene, etc.

Preferably, the antibody used in the present invention is expressed in a mammal cell, for example, CHO, COS, myeloma, BHK, Vero and HeLa cell.

In the case of a mammalian cell, as a vector for the introduction and expression of the target gene, those derived from viruses such as SV 40, polyoma virus, adenovirus virus and bovine papilloma virus (BPV) can be used.

For the purpose of expressing the antibody gene in a host cell, a useful promoter regularly used, the antibody gene to be expressed and a poly A signal on the 3' side downstream thereof must be linked functionally. Examples of this promoter/enhancer include human cytomegalovirus immediate early promoter/enhancer.

In addition to this, examples of the promoter/enhancer which can be used for the antibody expression used in the present invention include viral promoters/enhancers such as retrospective virus, polyoma virus, adenovirus virus and simian virus 40 (SV 40) as well as promoters/enhancers derived form mammalian cells such as human elongation factor 1α (HEF1α).

Gene expression can be easily performed according to the method by Mulligan et al. (Nature (1979) 277, 108) in the case where the above-mentioned SV 40 promoter/enhancer is used or according to the method by Mizushima et al. (Nucleic Acids Res. (1990) 18, 5322) in the case where HEF1α promoter/enhancer is used.

The expression vector can contain aminoglycoside transferase (APH) gene, thymidine kinase (TK) gene, adenosine deaminase (ADH) gene, hygromycin B phosphotransferase (HPH) gene, dihydrofolate reductase (dhfr) gene, etc. as a selection marker if needed.

The transformed host cells are cultured either in vitro or in vivo to produce the target antibody. Culturing of host cells can be performed according to a well-known method. For example, DMEM, MEM, RPM11640 and IMDM can be used as a culture solution, and as long as it is required, a serum supplementary liquid such as Fetal Bovine Serum (FCS) can be used together.

1-7 Separation and Purification of Antibody

The expressed and produced antibody as mentioned above is separated from a cell or a host animal and purified as a homogeneous antibody. Separation and purification of the antibody used in the present invention can be performed using affinity column. Examples of such a column include Hyper D, POROS, Sepharose F. F. (Pharmacia), etc. which are columns using protein A. In addition, any method of separation and purification used for usual protein can be used if needed. For example, the antibody can be separated and purified by suitably selecting and combining chromatography columns other than the above-mentioned affinity column, filter, ultrafiltration, salting out, dialysis, etc. (Antibodies A Laboratory Manual. Ed Harlow, David Lane, Cold Spring Harbor Laboratory, 1988).

1-8 Confirmation of Activity of Antibody

A well-known means can be used for measurement of the antigen binding activity (Antibodies A Laboratory Manual. Ed Harlow, David Lane, Cold Spring Harbor Laboratory, 1988), inhibitory activity against ligand-receptor binding (Harada, A. et al., International Immunology (1993) 5, 681-690) of the antibody used in the present invention.

As a method of measuring the antigen binding activity of the anti-PTHrP antibody used in the present invention, ELISA (enzyme-linked immunosorbent assay), EIA (enzyme immunoassay) and RIA (radioimmunoassay), or a fluorescence antibody method can be used. For example, when using an enzyme immunoassay, the sample which contains an anti-PTHrP antibody, for example, a culture supernatant of an anti-PTHrP antibody producing cells or the purified antibody is added to the plate coated with PTHrP (1-34). The secondary antibody labeled with an enzyme such as alkaline phosphatase is added, and after the plate is incubated and washed, a substrate of the enzyme such as p-nitrophenyl phosphate is added and the absorption is measured to estimate the antigen binding activity.

In order to confirm the activity of the antibody used in the present invention, the neutralization activity of the anti-PTHrP antibody is measured.

1-9 The Administration Method and Preparation

Although the agent for treating chondroma and chondrosarcoma which contains the anti-PTHrP antibody of the present invention as an active ingredient can be either administered orally or parentally, but parental administration is preferable. Specifically, examples of a suitable dosage form include a transpulmonary dosage form (for example, transpulmonary administration agent using instruments such as nebulizer), a transnasal administration dosage form, a transcutaneous administration dosage form (for example, ointment, cream agent), an injection dosage form, etc. Examples of the injection dosage form include intravenous infusion, for example, drip and the like, intramuscular injection, intraperitoneal administration, hypodermic injection, etc. thereby, systemic or local administration can be performed. Administration method can also be suitably selected according to the age and condition of a patient.

The effective amount of administration of the agent of the present invention is usually selected from the range of 0.001 to 1000 mg per 1 kg of body weight per time. Or alternatively, it is selected from the range of 0.01 to 100000 mg/body. However, the amount of administration of the agent for treating chondroma and chondrosarcoma containing the anti-PTHrP antibody of the present invention is not limited to these ranges.

Although the diseases which can be the object for which the agent of the present invention is administered are chondroma and chondrosarcoma, they encompass chondroma and chondrosarcoma associated or concurred with the other diseases.

The agent of the present invention induces differentiation and apoptosis of a chondroma and chondrosarcoma cell, and thereby kills the cell and controls chondroma and chondrosarcoma.

The time to administrate the agent of the present invention may be either before or after the clinical condition of the above-mentioned disease arises, and it may be preventively administered or sustainingly administered.

The agent which contains the anti-PTHrP antibody of the present invention as an active ingredient can be formulated according to a usual method (Remington's Pharmaceutical Science, latest edition, Mark Publishing Company, Easton, U.S.), and may contain pharmaceutically accepted carriers and additives as well.

Examples of such carriers and pharmaceutical additives include: water, pharmaceutically accepted organic solvents, collagen, polyvinyl alcohol, polyvinylpyrrolidone, carboxy vinyl polymer, sodium carboxymethylcellulose, sodium polyacrylate, sodium alginate, water-soluble dextran, sodium carboxymethyl starch, pectin, methylcellulose, ethyl cellulose, xanthan gum, gum arabic, casein, agar, polyethyleneglycol, diglycerol, glycerin, propylene glycol, vaseline, paraffine, stearyl alcohol, stearin acid, human serum albumin (HSA), mannitol, sorbitol, lactose, and surfactant accepted as pharmaceutical additives.

Although the particular additives may be selected alone or in combination with the above according to the dosage form of the agent of the present invention, they are not limited to this particular list. For example, when the preparation is used as a formulation for injection, the purified anti-PTHrP antibody can be dissolved in a solvent, for example, saline, buffer solution, glucose solution, etc., and can be used in combination with an absorption preventing agent, for example, Tween80, Tween20, gelatin, human serum albumin, etc. added thereto. Alternatively, the preparation may be freeze-dried to create a dosage form to be dissolved and reconstructed prior to use, and as an excipient for freeze-drying, a sugar alcohol and a sugar such as mannitol and glucose can be used, for example.

2. Method for Inducing Apoptosis to Chondroma and Chondrosarcoma Cells

The present invention also provides a method of inducing apoptosis to chondroma and chondrosarcoma cells by administering a substance which inhibits binding of a parathyroid hormone related peptide and a receptor thereof.

"Apoptosis" as used herein means the cell death caused by the cell itself under physiological conditions. Apoptosis is morphologically characterized by chromatin condensation, fragmentation of nucleus and atrophy of a cell by condensation of cytoplasm, and it is not accompanied by discharge of the contents of the cell. At this point, apoptosis is clearly distinguished from the necrosis accompanied by discharge of the contents of the cell.

In the method of the present inventor, "the substance which inhibits binding of parathyroid hormone related peptide and a receptor thereof" is preferably an anti-parathyroid hormone related peptide antibody. Fragments and/or modified substances thereof are also contained in this antibody, and the antibody is preferably a monoclonal antibody. Furthermore, if it is the case where the antibody is used for human chondroma and chondrosarcoma cell, the antibody is preferably a humanized antibody or a chimerized antibody. Suitable examples of such an antibody include humanized #23-57-137-1 antibody, for example. Although the mechanism by which apoptosis is induced in chondroma and chondrosarcoma cells by the method of the present invention is not clear, it is presumed that activation of caspase-3 and/or expression control of Bcl-2/Bax which closely relates to apoptosis may mediate apoptosis.

This specification incorporates the contents disclosed in the specification and/or drawings of the Japanese Patent Application No. 2002-334081 from which the present application claims priority.

BEST MODE FOR CARRYING OUT THE INVENTION

The present invention will be described more specifically below by way of Examples and Referential Examples. The technical scope of the present invention, however, is not limited to these Examples, etc.

EXAMPLE 1

Effect of an Anti-PTHrP Antibody on Chondrosarcoma Cell (HTB-94)

1. Test Method 1.1 Culturing of Cells

Human chondrosarcoma cell HTB-94 (ATCC) was suspended in Dulbecco's Modified Eagle's Medium (DMEM) containing 10% FBS, L-glutamine, penicillin-streptomycin (all are available from GIBCO-BRL), and was cultured and proliferated at 37° C. under 5% $CO_2$ wet condition.

1.2 Preparation of Mouse Monoclonal Antibody to Human PTHrP (1-34)

The mouse monoclonal antibody (hereinafter referred to as "anti-PTHrP MoAb") to human PTHrP (1-34: peptide which consists of 1-34 amino-acid sequence of PTHrP) was prepared from hybridoma ##23-57-137-1 (FERM BP-5631; JP Patent Publication (Kokai) No. 11-092500A (1999)). The general procedure of hybridoma preparation is described in Referential Example 1.

1.3 Viability of Cells

HTB-94 cells ($1\times10^4$ cells/well in 100 μL) were incubated for two days in a DMEM culture medium containing anti-PTHrP MoAb (0, 10, 100, or 200 μg/ml), and the viability of the cells was evaluated by Premix WST-1 Cell Proliferation Assay System (TAKARA SHUZO). That is, reduction ratio of tetrazolium salt (WST-1) by viable cells was determined from the increase in OD450, and it was considered as the index of the number of viable cells.

Similarly, viability of the cells which were treated with a caspase-3 inhibitory agent DEVO-CHO (20 μM (Calviochem)) 2 hours before the addition of anti-PTHrP MoAb was also evaluated.

1.4 Western Blotting

HTB-94 cells were treated for two days with anti-PTHrP MoAb (0, 10, 30, 50, 100, and 200 μg/ml). In the experiment with regard to the following collagen type-X, the cells were treated by anti-PTHrP MoAb for further five days (for total seven days). All the cell lysates (50 μg as protein) of the above-mentioned cells were separated by SDS-PAGE using 12% gel and blotted on a nitrocellulose film (Bio-Rad Laboratories). The blocked film was incubated together with an anti-procaspase-3 antibody (Wako Pure Chemical) diluted to 1/100, an anti-PARP antibody, an anti-Bcl-2 antibody and an anti-Bax antibody (both from Santa Cruz Biotechnology), an anti-collagen type X antibody (Calbiochem-Novabiochem Corporation) and a peroxidase conjugated secondary antibody (Amersham) diluted to 1/1000.

Here, PARP (poly(ADP-ribose) polymerase) is an enzyme important for the survival in a cell, and caspase-3 causes cleavage of this PARP. The above-mentioned anti-PARP antibody is an antibody which recognizes 116 kDa and 85Da PARP fragments but does not recognize 25 kDa fragment. Procaspase-3 is an inactive caspase having no caspase activity.

Figure 3:
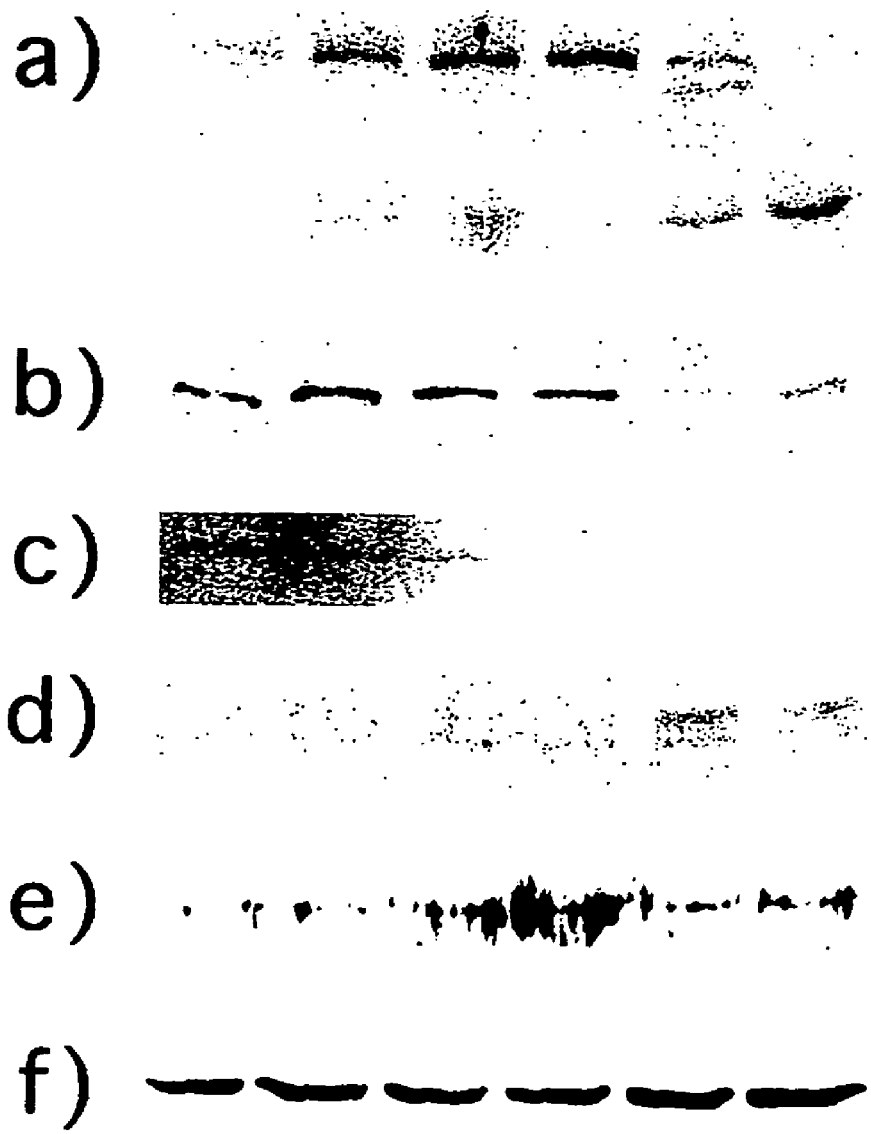
FIG. 3 shows the results of Western blotting, in which a) PARP, b) procaspase-3, c) Bcl-2, d) Bax, e) collagen type X, f) β-actin; Each column corresponds to the anti-PTHrP MoAb concentration 0, 10, 30, 50, 100, and 200 μg/ml, respectively from the left to the right.

Detection was performed using ECL Western blotting detection system (Amersham). Each blot was further re-detected by ECL using anti-o-actin antibody (Santa Cruz Biotechnology) and the peroxidase conjugated secondary antibody. The results are shown in FIG. 3.

1.5 Immunocytochemistry

1) Analysis using Anti-Collagen Type X Antibody

Figure 4:
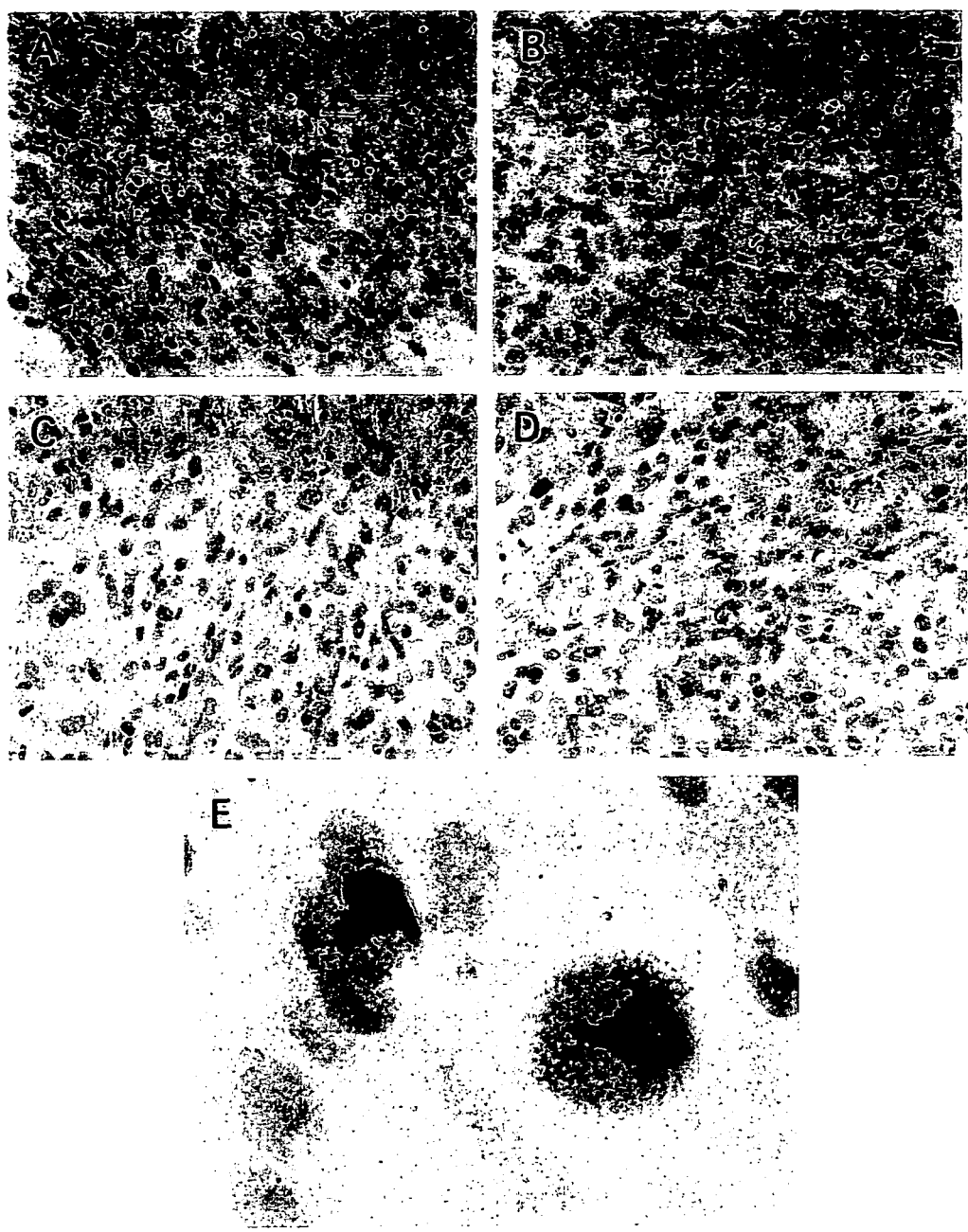
FIG. 4 shows the results of the immunocytochemistry using the anti-collagen type X antibody, in which A: untreated, B: treated with 10 μg/ml of anti-PTHrP MoAb, C: treated with 100 μg/ml anti-PTHrP MoAb, D-F: treated with 200 μg/ml anti-PTHrP MoAb (A-D: ×200, E: ×400)

Immunocytochemistry was performed by streptavidin-peroxidase method using histofine SAB-PO kit (NICHIREI). That is, HTB-94 cells were cultured until they became 50% confluent on a chamber slide, treated with anti-PTHrP MoAb (0, 10, 100, or 200 μg/ml), cultured for further seven days. Subsequently, the cells were transferred to 3% $H_2O_2$ methanol to block endogenous peroxidase activity, washed with PBS (pH 7.2), and then blocked with PBS containing normal 10% serum (secondary antibody) of the congeneric origin in order to make the background minimum and incubated with anti-collagen type X antibody (primary antibody) at room temperature for 2 hours. Afterwards the cells were washed with PBS, incubated with the secondary antibody at room temperature in a wet chamber for 20 minutes, and incubated with peroxidase conjugated streptavidin (NICHIREI) for 20 minutes under the same conditions. Finally, coloring reaction was performed with 3,3-diaminobenzidine tetrahydrochloride (DAB) reagent (Dojindo). The cells were counterstained with hematoxylin and microscopically observed at 200-fold and 400-fold magnification. The results are shown in FIG. 4.

2) TUNEL Staining

Figure 5:
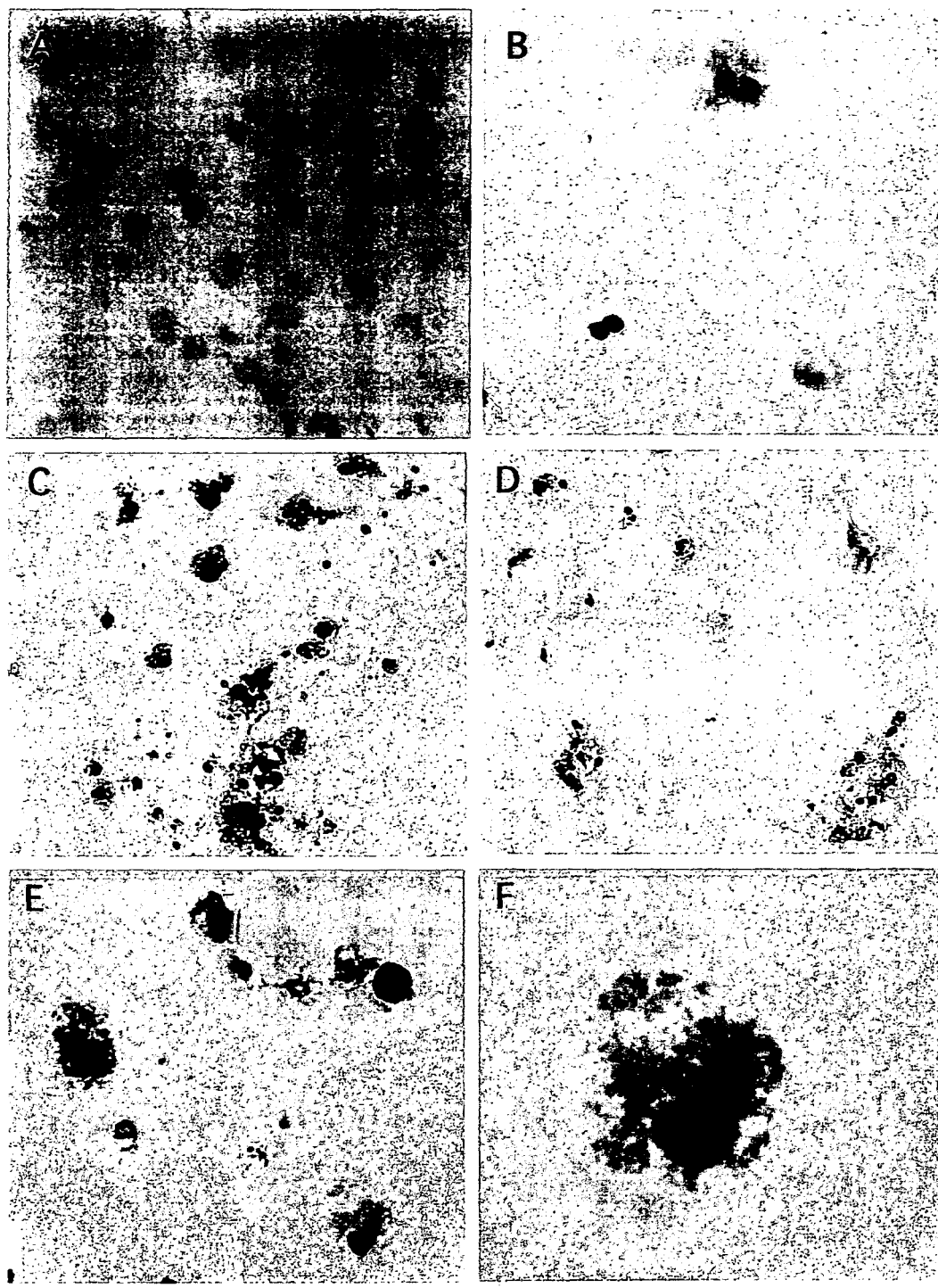
FIG. 5 shows the results of TUNEL staining, in which A: untreated, B: treated with 10 μg/ml anti-PTHrP MoAb, C: treated with 100 μg/ml anti-PTHrP MoAb, and D-F: treated with 200 μg/ml anti-PTHrP MoAb (A-D: ×200, E: ×400, F: ×600)

TUNEL staining was performed using Apoptag Peroxidase Kit (Intergen Company). That is, after HTB-94 cells (0, 10, 100, or 200 μg/ml) were treated with anti-PTHrP MoAb for two days, they were treated with methanol containing 0.3% $H_2O_2$ for 20 minutes and equilibrated in an end nucleotide transferase (TdT) buffer at room temperature for 15 minutes. Subsequently, the cells were incubated with a TdT reaction mixture (TdT solution+digoxigenin-11-dUDP and dATP) at 37° C. for 60 minutes, and further incubated with peroxidase conjugated anti-dioxygenin antibody at room temperature for 30 minutes. The cells were stained with DAB and then counterstained with Mayer's hematoxylin and microscopically observed at 200-fold, 400-fold and 600-fold magnification. The results are shown in FIG. 5.

1.6 RT-PCR

Total RNA was extracted from HTB-94 cells (control and treated with 100 μg/ml anti-PTHrP MoAb for two days) using ISOGEN. cDNA was synthesized from a mixture containing 2 μg of total RNA using (dT) 12-18 primer and 200 units of SuperScript II reverse transcriptase (GIBCO BRL) at 37° C. for 60 minutes.

PCR of cDNA was performed using Ready-to-Go PCR beads (Pharmacia) and primers for human Bcl-2, Bax, Ihh, ColX (α1) and β-actin amplification (12.5 pmol(s) each).

human Bcl-2(PCR product 235 bp)

```
        sense:                    (SEQ ID No. 76)
    5'-CAGATGCACC TGACGCCCTT-3' antisense:                (SEQ ID No. 77)
    3'-CCCAGCCGTG GTTATCCTGGA-3'
``` human Bax(PCR product 224 bp)

```
        sense:                    (SEQ ID No. 78)
    5'-GTCCACCAAG AAGCTGAGCG-3' antisense:                (SEQ ID No. 79)
    3'-TTGGTGCACA GGGCCTTGAG-3'
``` human Collagen type X (PCR product 288 bp)

```
        sense:                    (SEQ ID No. 80)
    5'-CAGGAAAACC AGGTCTCGAT G-3' antisense:                (SEQ ID No. 81)
    3'-TTGAGGCCCT TAGTTGCTAT G-3'
``` human Collage type II(PCR product 351 bp)

```
        sense:                    (SEQ ID No. 82)
    5'-AGAGTGCTGC CCCATCTGCC CAACTGACCT-3' antisense:                (SEQ ID No. 83)
    3'-CATTACTCCC AACTGGGCGC CACCAGCCTT-3'
``` human β-actin: PCR product 320 bp

```
        sense:                    (SEQ ID No. 84)
    5'-CGGACTCGTC ATACTCCTGC TT-3' antisense:                (SEQ ID No. 85)
    3'-CACTCTTCCA GCCTTCCTTC C-3'
```

Amplification was performed using Perkin-Elmer/Cetus DNA Thermal Cycler (TAKARA SHUZO) on the conditions of 30 cycles each of 94° C., 0.5 min; 55° C., 0.5 min; 72° C., 0.5 min and last extension reaction at 72° C. for 7 minutes.

Figure 6:
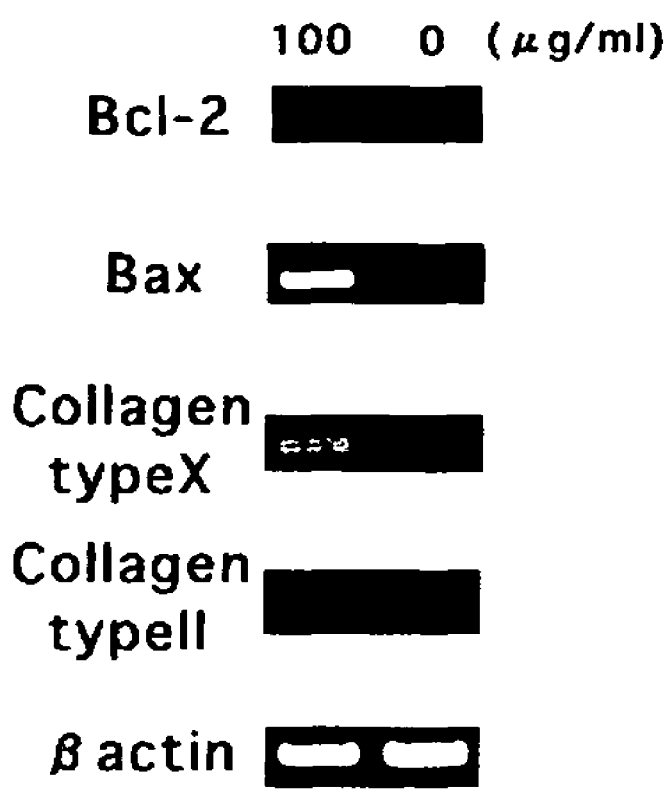
FIG. 6 shows the results of RT-PCR in the cells treated with anti-PTHrP MoAb and untreated cells (wherein the vertical axis is anti-PTHrP MoAb concentration)

Electrophoresis of the obtained PCR product (10 μL) was carried out on a 4% agarose gel, and stained and observed with ethidium bromide. The results are shown in FIG. 6.

1.7 DNA Fragmentation Assay

Figure 7:
FIG. 7 shows the results of DNA fragmentation assay in the cells treated with anti-PTHrP MoAb and untreated cells.

After HTB-94 cells ($1\times10^7$) were treated with anti-PTHrP MoAb (0, 10 and 200 μg/ml) for two days, they were washed with PBS and DNA was isolated using Apopladder Ex kit (TAKARA SHUZO). That is, the cells were dissolved in a dissolution buffer, DNA was isolated, extracted with an organic solvent and ethanol precipitation was carried out. The precipitated DNA was centrifuged (12,000 g, 10 min) and then washed with 80% ethanol, and dissolved in 30 μl of TE buffer. Each sample (10 μl) was subjected to electrophoresis on a 1.2% agarose gel, and stained with ethidium bromide. The results are shown in FIG. 7.

2. Test Results

2.1 Cell Viability

Figure 1:
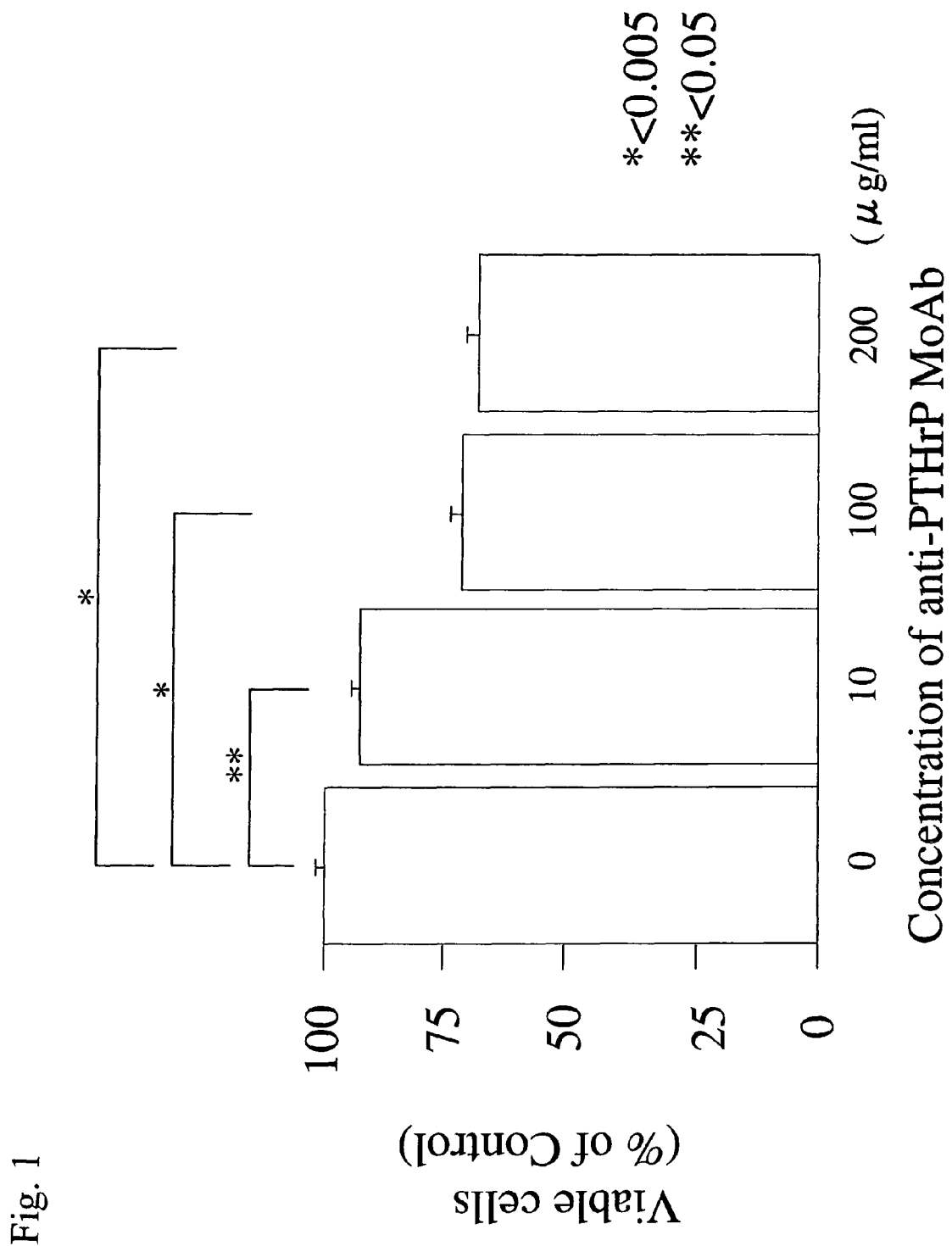
FIG. 1 is a graph showing the effect of anti-PTHrP MoAb on the cell viability.
Figure 2:
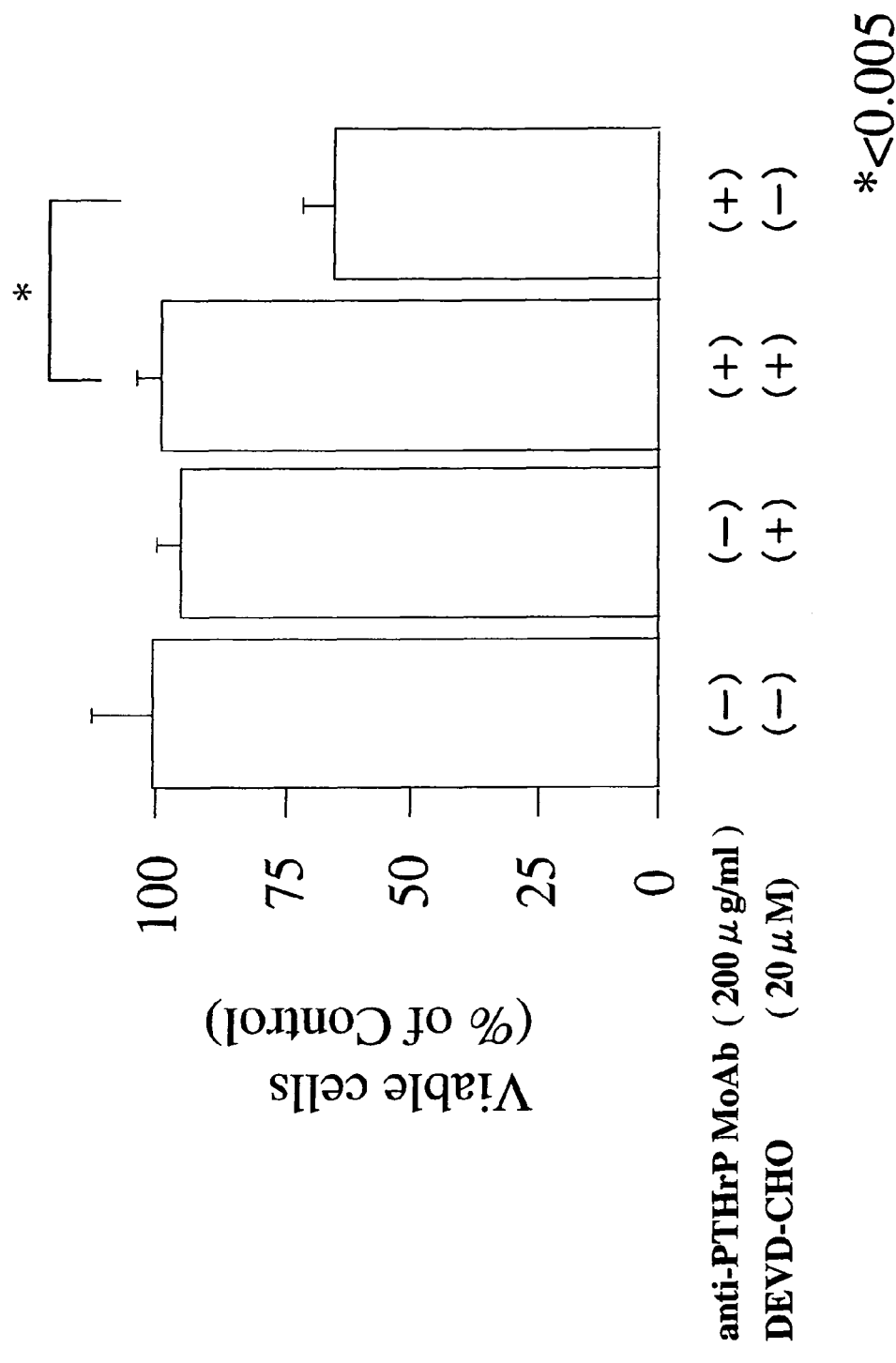
FIG. 2 is a graph showing the effect of caspase-3 inhibitory agent (DEVD-CHO) on the viability of an anti-PTHrP MoAb treated cell.

The viability of HTB-94 cell was inhibited depending on the concentration of anti-PTHrP MoAb (FIG. 1). Moreover, DEVD-CHO which is a specific inhibitor of caspase-3 inhibited the effect of this anti-PTHrP MoAb. The viability of cells is higher for those treated rather than those not treated with caspase-3. In the drawing, the number of viable cells in each concentration is shown by % to control (untreated).

2.2 Western Blotting a) Although the 85 kDa fragment of PARP increased depending on the concentration for HTB-94 cells treated with Anti-PTHrP MoAb, increase was not confirmed in untreated cells. Although low molecular weight fragments were slightly confirmed in any cell, these were considered to be spontaneousy decomposed from PARP.

b) Although procaspase-3 (35 kDa) was also detected, it was decreased in the high-concentration anti-PTHrP MoAb (100 and 200 μg/ml) treated cells. This is considered to be attributable to active heterodimers resulted from cleavage of procaspase-3 with anti-PTHrP MoAb treatment.

c) Bcl-2 decreased as the concentration of anti-PTHrP MoAb increased.

d) Bax increased as the concentration of anti-PTHrP MoAb increased.

e) There was more collagen type X in the cells treated with Anti-PTHrP MoAb than in untreated cells and the maximum was 50 μg/ml concentration of anti-PTHrP MoAb.

f) As for β-actin, there was little difference in the amount of expression in any cell.

2.3 Immunocytochemistry

1) Analysis using Anti-Collagen Type X Antibody

The ratio of stained HTB-94 cells increased depending on the concentration of anti-PTHrP MoAb. Among the cells treated with Anti-PTHrP MoAb (particularly at high concentration), a number of cells which roundly expanded were observed (FIG. 4). There are many reports that cartilage cells become expanded as differentiation proceeds, and that the expression of collagen type X antibody is high in these expanded cartilage cells. Therefore, the above-mentioned result shows that differentiation of HTB-94 cells was promoted by anti-PTHrP MoAb treatment.

2) TUNEL Staining

HTB-94 cells stained brown are cells in apoptosis. The frequency of appearance increased depending on the concentration of anti-PTHrP MoAb. Furthermore, in the cell after Anti-PTHrP MoAb treatment, morphological changes of contraction and round outline were also recognized (FIG. 5). This morphological change is characteristic of apoptosis. Therefore, the above-mentioned results show that the apoptosis of HTB-94 cells was promoted by anti-PTHrP MoAb treatment.

2.4 RT-PCR

The amount of expression of Bax and Collagen type II increased while the amount of expression of Bcl-2 decreased by anti-PTHrP MoAb treatment. There was no change in the amount of expression of collagen type II and β-actin.

2.5 DNA Fragmentation Assay

Fragmentation of DNA in nucleosome specific to apoptosis was observed in the cells treated with 10 μg/ml and 200 μg/ml of anti-PTHrP MoAb. On the other hand, fragmentation was not observed in untreated cells.

3. Consideration

From the above result, it was proved that differentiation and apoptosis of HTB-94 cells were induced by anti-PTHrP MoAb treatment. This effect strongly supports that anti-PTHrP MoAb can be useful as an agent of chondroma and chondrosarcoma.

It is reported that proteins important for cell maintenance like PARP are cleaved with activated caspase-3 in apoptosis leading to cell death. That is, the above-mentioned results suggest that anti-PTHrP MoAb induces apoptosis mediated by Bcl-2/Bax and caspase-3 and inhibits proliferation of HTB-94 cell.

REFERENTIAL EXAMPLE 1

Preparation of Hybridoma Producing Anti-PTHrP (1-34) Mouse Monoclonal Antibody

Hybridomas #23-57-154 and #23-57-137-1 which produce monoclonal antibody to human PTHrP (1-34) were produced as follows (Sato, K. et al., J. Bone Miner. Res. 8, 849-860, 1993). The amino acid sequence of human PTHrP (1-34) is shown in the SEQ ID No. 75.

In order to use as an immunogen, a career protein, silo globulin was linked with PTHrP (1-34) (product of Peninsula) using carbodiimide (Dojinn). PTHrP (1-34) linked with silo globulin was dialyzed and adjusted to 2 μg/nm as a protein concentration, it was mixed with Freund's adjuvant (Difco) by 1:1, and after an emulsion was prepared, 16 female BALB/C mice were immunized with 100 μg per animal 11 times hypodermically on the back or interperitoneally. Complete Freund's adjuvant was used for the first time immunization, and incomplete Freund's adjuvant was used for the additional immunization of the second time and thereafter.

Measurement of antibody value in the serum of the immunized mouse was carried out by the following method. That is, the blood was collected from the mouse tail vein, and after the serum was separated, the anti-serum diluted with RIA buffer and $^{125}$I labeled PTHrP (1-34) were mixed, and binding activity was measured. The mice with elevated antibody value were subjected to the final immunization using 50 μg per animal of PTHrP (1-34) not bound with career protein by interperitoneal injection.

The mouse was slaughtered on the third day of the final immunization. The mouse's spleen was removed and the cell fusion of the spleen cell and mouse myeloma cell line P3x63Ag8U.1 was carried out according to a usual method using 50% polyethyleneglycol 4000. The fused cells were seeded on 85 sheets of 96-well plate with the number of cells of $2\times10^4$/well. Selection of hybridomas was performed using HAT culture medium.

Screening of hybridomas was performed by measuring and selecting the existence of a PTHrP recognizing antibody by applying solid phase RIA method to the culture supernatant of the wells where growth was recognized in HAT culture medium. Hybridomas were collected from the wells where binding ability with an antibody was recognized, suspended to the culture medium prepared by adding OPI-supplement (Sigma) to the RPMI-1640 culture medium containing FCS 15%, and the hybridomas was simplified by the limiting dilution method. Clones #23-57-154 and #23-57-137-1 with strong binding ability with PTHrP (1-34) were obtained.

As mentioned above, hybridoma clone #23-57-137-1 was internationally deposited as mouse-mouse hybridoma #23-57-137-1 under FERM BP-5631 on Aug. 15, 1996 under the Budapest Treaty with International Patent Organism Depositary, National Institute of Advanced Industrial Science and Technology, an Independent Administrative Institution, located at Tsukuba Central 6, 1-1-1 Higashi, Tsukuba, Tbaraki, Japan.

REFERENTIAL EXAMPLE 2

Cloning of DNA Encoding the V Domain of the Mouse Monoclonal Antibody to Human PTHrP (1-34

The cloning of the DNA encoding the variable domain of mouse monoclonal antibody #23-57-137-1 to human PTHrP (1-34) was carried out as follows.

(1) Preparation of mRNA mRNA from hybridoma #23-57-137-1 was prepared using Quick Prep mRNA Purification Kit (Pharmacia Biotech). The cells of hybridoma #23-57-137-1 was completely homogenized with an extraction buffer, mRNA was purified in oligo (dT)-Cellulose Spun Column according to the instructions appended to the kit, and ethanol precipitation was performed. The mRNA sediment was dissolved in an elution buffer.

(2) Production and Amplification of cDNA of a Gene Encoding the V Domain of the Mouse H Chain (i) Cloning of #23-57-137-1 Antibody H Chain V Domain cDNA The cloning of the gene encoding the V domain of the H chain of mouse monoclonal antibody to human PTHrP was performed by 5'-RACE method (Frohman, M. A. et al., Proc. Natl. Acad. Sci. USA, 85, 8998-9002, 1988; Belyavsky, A. et al., Nucleic Acids Res. 17, 2919-2932, 1989). The 5'-RACE method was carried out using 5'-Ampli FINDER RACE kit (CLONETECH) and operations according to the instructions appended to the kit. As a primer to be used for cDNA synthesis, MHC2 primer (SEQ ID No. 1) which hybridizes with the constant domain (C domain) of mouse H chain was used. Ten (10) pmoles of MHC2 primer was added using as a template about 2 μg of mRNA prepared as mentioned above, and reverse transcription to cDNA was performed by reacting at 52° C. for 30 minutes with a reverse transcriptase.

After hydrolyzing RNA with 6N NaOH (65° C., 30 minutes), cDNA was purified by ethanol precipitation. Ampli FINDER Anchor (SEQ ID No. 42) was linked to 5'-end of the synthesized cDNA by reacting with T4RNA ligase at room temperature for 6 hours and at 37° C. for 16 hours. This was used as a template and amplified by PCR using Anchor primer (SEQ ID No. 2) and MHC-G1 primer (SEQ ID No. 3) (S. T. Jones, et al., Biotechnology, 9, 88, 1991).

PCR solution contains 10 mM Tris-HCl (pH 8.3), 50 mM KCl, 0.25 mM dNTPs (dATP, dGTP, dCTP, and dTTP), 1.5 mM $MgCl_2$, 2.5 units of TaKaRa Taq (TAKARA SHUZO), 10 pmoles of Anchor primer and 1 µl of reaction mixture of cDNA to which MHC-G1 primer and Ampli FINDER Anchor were linked in 50 µl of the solution. To this solution 50 µl of a mineral oil layer was blanketed. PCR was performed using Thermal Cycler Model 480J (Perkin Elmer) with 30 times of the temperature cycle consisting of 94° C. for 45 seconds, 60° C. for 45 seconds and 72° C. for 2 minutes.

(ii) Cloning of cDNA of #23-57-137-1 Antibody L Chain V Domain

The cloning of the gene encoding the V domain of the L chain of mouse monoclonal antibody to human PTHrP was performed by 5'-RACE method (Frohman, M. A. et al., Proc. Natl. Acad. Sci. USA, 85, 8998-9002, 1988; Belyavsky, A. et al., Nucleic Acids Res. 17, 2919-2932, 1989). The 5'-RACE method was carried out using 5'-Ampli FINDER RACE kit (CLONETECH) and operations according to the instructions appended to the kit. As a primer to be used for cDNA synthesis, oligo-dT was used. The oligo-dT primer was added using as a template about 2 µg of mRNA prepared as mentioned above, and reverse transcription to cDNA was performed by reacting at 52° C. for 30 minutes with a reverse transcriptase.

After hydrolyzing RNA with 6N NaOH (65° C., 30 minutes), cDNA was purified by ethanol precipitation. The above-mentioned Ampli FINDER Anchor was linked to 5'-end of the synthesized cDNA by reacting with T4RNA ligase at 37° C. for 6 hours and at room temperature for 16 hours.

A PCR primer MLC (SEQ ID No. 4) was designed from the conserved sequence of a mouse L chain λ chain constant domain, and synthesized using 394 DNA/RNA Synthesizer (ABI company). PCR solution contains 10 mM Tris-HCl (pH 8.3), 50 mM KCl, 0.25 mM dNTPs (dATP, dGTP, dCTP, and dTTP), 1.5 mM $MgCl_2$, 2.5 units of AmpliTaq (PERKIN ELMER), 50 pmoles of Anchor primer (SEQ ID No. 2) and 1 µl of reaction mixture of cDNA to which MLC (SEQ ID No. 4) and Ampli FINDER Anchor were linked in 100 µl of the solution. To this solution 50 µl of a mineral oil layer was blanketed. PCR was performed using Thermal Cycler Model 480J (Perkin Elmer) with 35 times of the temperature cycle consisting of 94° C. for 45 seconds, 60° C. for 45 seconds and 72° C. for 2 minutes.

(3) Purification and Fragmentation of PCR Product

The DNA fragment amplified by the PCR method as mentioned above was separated by agarose gel electrophoresis using 3% Nu Sieve GTG agarose (FMC Bio. Products). Pieces of agarose which contains the DNA fragment of about 550 bp length as the V domain of the L chain and about 550 bp length as the V domain of the H chain were excised, and the DNA fragment was purified using GENECLEAN II Kit (BIO101) according to the instructions appended to the kit. The purified DNA was precipitated with ethanol, and then dissolved in 10 mM Tris-HCl (pH 7.4) and 20 µl of 1 mM EDTA solution. 1 µl of the obtained DNA solution was digested with a restriction enzyme XmaI (New England Biolabs) at 37° C. for 1 hour, and subsequently it was digested with the restriction enzyme EcoRI (TAKARA SHUZO) at 37° C. for 1 hour. This digested mixture was extracted with phenol and chloroform, and DNA was collected by ethanol precipitation.

In this way, a DNA fragment containing a gene encoding the mouse H chain V domain and L chain V domain which has EcoRI recognition sequence at the 5'-end and has XmaI recognition sequence at the 3'-end was obtained.

The EcoRI-XmaI DNA fragment containing a gene encoding the mouse H chain V domain and L chain V domain prepared as mentioned above and a pUC19 vector prepared by digesting by EcoRI and XmaI were ligated using DNA ligation kit ver. 2 (TAKARA SHUZO) at 16° C. for 1 hour according to the appended instructions. Next, 10 µl of the above-mentioned ligated mixture was added to 100 µl of *E. coli* JM109 competent cells (NIPPON GENE), and these cells were allowed to stand still for 15 minutes on ice, at 42° C. for 1 minute and further allowed to stand still for 1 minute on ice. Subsequently, 300 µl of SOC culture medium (Molecular Cloning: A Laboratory Manual, Sambrook, et al., Cold Spring Harbor Laboratory Press, 1989) was added and incubated at 37° C. for 30 minutes and then the *E. coli* was seeded on LB agar culture medium or 2xYT agar culture medium (Molecular Cloning: A Laboratory Manual, Sambrook, et al., Cold Spring Harbor Laboratory Press, 1989) which contains ampicillin (100 µg/ml or 50 µg/ml), 0.1 mM IPTG and 20 µg/ml of X-gal and incubated at 37° C. overnight to obtain transformed *E. coli*.

Overnight culturing of this transformant was carried out at 37° C. in LB culture medium containing 100 µg/ml or 50 µg/ml of ampicillin or 2 ml of 2xYT culture medium, and plasmid DNA was prepared using plasmid extraction machine PI-100Σ (Kurabo Industries) or QIAprep Spin Plasmid Kit (QIAGEN) from the cell body fraction, and nucleotide sequence was determined.

(4) Determination of Nucleotide Sequence of Gene Encoding Mouse Antibody V Domain The nucleotide sequence of the cDNA code domain in the above-mentioned plasmid was determined using Dye Terminator Cycle Sequencing kit (Perkin-Elmer) and by DNA Sequencer 373A (ABI company Perkin-Elmer). The sequence was determined by confirming the nucleotide sequence of both directions using M13 Primer M4 (TAKARA SHUZO) (SEQ ID No. 5) and M13 Primer RV (TAKARA SHUZO) (SEQ ID No. 6) as primers for sequence determination.

The obtained plasmid containing a gene encoding the mouse H chain V domain originating from hybridoma #23-57-137-1 was designated as MBC1H04 and the plasmid containing a gene encoding the mouse L chain V domain was designated as MBC1L24. The nucleotide sequence (including corresponding amino acid sequences) of the gene encoding the H chain V domain and L chain V domain of mouse #23-57-137-1 antibody which are contained in plasmid MBC1H04 and MBC1L24 are shown as SEQ ID Nos. 57 and 65, respectively. The amino acid sequences are shown as SEQ ID No. 46 for the fragment of the V domain of the H chain and as SEQ ID No. 45 for the fragment of the V domain of the L chain.

The *E. coli* which has the above-mentioned plasmid MBC1H04 and MBC1L24 were internationally deposited as *Escherichia coli* JM109 (MBC1H04) and *Escherichia coli* JM109 (MBC1L24) on Aug. 15, 1996 under the Budapest Treaty with International Patent Organism Depositary, National Institute of Advanced Industrial Science and Technology, an Independent Administrative Institution, located at Tsukuba Central 6, 1-1-1 Higashi, Tsukuba, Ibaraki, Japan under accession number FERM BP-5628 for *Escherichia coli* JM109 (MBC1H04) and FERM BP-5627 for *Escherichia coli* JM109 (MBC1L24).

(5) Determination of CDR of Mouse Monoclonal Antibody #23-57-137-1 to Human PTHrP The whole structure of V domain of the H chain and V domain of the L chain has similarity mutually, and four framework portions are connected by three super variable domains (CDR), i.e., a complementarity determination region, respectively. Although the amino acid sequence of the frameworks is comparatively well conserved, on the other hand, the mutation ratio of the amino acid sequence of the CDR domain is very high (Kabat, E. A. et al., "Sequence of Proteins of Immunological Interest" US Dept. Health and Human Services, 1983).

Based on the above fact, the amino acid sequence of the variable domain of the mouse monoclonal antibody to human PTHrP was applied to the database of the amino acid sequence of the antibody created by Kabat et al., and by investigating homology, it determined as a CDR domain was shown in Table 1.

The amino acid sequences of CDRs 1 to 3 of the V domain of the L chain was shown in the SEQ ID Nos. 59 to 61, respectively, and the amino acid sequence of CDR 1 to 3 of the V domain of the H chain are shown in the SEQ ID No. 62 to 64, respectively.

TABLE 1

| V domain | SEQ ID No. | CDR1 | CDR2 | CDR3 |
|---|---|---|---|---|
| H chain V domain | 57 | 31-35 | 50-66 | 99-107 |
| L chain V domain | 65 | 23-34 | 50-60 | 93-105 |

REFERENTIAL EXAMPLE 3

Construction of Chimeric Antibody (1) Construction of Chimeric Antibody H Chain (i) Construction of V Domain of H Chain In order to ligate to an expression vector containing a genome DNA of Cγ1 of human H chain C domain, the cloned mouse H chain V domain was modified by PCR method. Reverse primer MBC1-S1 (SEQ ID No. 7) was designed so that it might hybridize with DNA encoding the 5'-side of the leader sequence of V domain and might have Kozak consensus sequence (Kozak, M. et al., J. Mol. Biol., 196, 947-950, 1987) and the recognition sequence of a restriction enzyme Hind III. Forward primer MBC1-a (SEQ ID No. 8) was designed so that it might hybridize with DNA encoding the 3'-side of J domain and it might have splice donor sequence and the recognition sequence of a restriction enzyme BamHI. PCR was performed using TaKaRa Ex Taq (TAKARA SHUZO) and the appended buffer solution under the condition where 0.07 μg of plasmid MBC1H04 as a template DNA, 50 pmoles each of MBC1-a and MBC1-S1 as primers, 2.5 U of TaKaRa Ex Taq and 0.25 mM dNTP were contained in 50 μl of the reaction mixture solution with 30 times of the temperature cycle consisting of 94° C. for 1 minute, 55° C. for 1 minute and 72° C. for 2 minutes while the solution was blanketed with 50 μl of a mineral oil layer. The DNA fragments amplified by the PCR method as mentioned above were separated by agarose gel electrophoresis using 3% Nu Sieve GTG agarose (FMC Bio. Products).

A piece of agarose which contains a DNA fragment of 437 bp length was excised, and the DNA fragment was purified using GENECLEAN II Kit (BIO101) according to the instructions appended to the kit. The purified DNA was collected by ethanol precipitation, and then dissolved in 10 mM Tris-HCl (pH 7.4) and 20 μl of 1 mM EDTA solution. 1 μl of the obtained DNA solution was digested with restriction enzymes BamHI and Hind III (TAKARA SHUZO) at 37° C. for 1 hour. This digested mixture was extracted with phenol and chloroform, and DNA was collected by ethanol precipitation.

The Hind III-BamHI DNA fragment containing a gene encoding the mouse H chain V domain prepared as mentioned above was subcloned into pUC19 vector prepared by digesting with Hind III and BamHI. In order to confirm the nucleotide sequence of this plasmid, M13 Primer M4 and M13 Primer RV were used as primers with Dye Terminator Cycle Sequencing kit (Perkin-Elmer) and the nucleotide sequence was determined using DNA Sequencer 373A (Perkin-Elmer). The plasmid containing a gene encoding the mouse H chain V domain originating from hybridoma #23-57-137-1 which has the correct nucleotide sequence and Hind III recognition sequence and Kozak sequence at 5'-side and BamHI recognition sequence at 3'-side was designated as MBC1H/pUC19.

(ii) Construction of the H Chain V Domain for Production of cDNA Type Mouse-Human Chimera H Chain In order to ligate to cDNA of Cγ1 of human H chain C domain, the mouse H chain V domain constructed as mentioned above was modified by PCR method. Reverse primer MBC1HVS2 (SEQ ID No. 9) for the V domain of the H chain was designed so that asparagine at the second position in the sequence encoding the beginning of the leader sequence of V domain might be changed into glycine and it might have Kozak consensus sequence (Kozak, M. et al., J. Mol. Biol., 196, 947-950, 1987), Hind III and EcoRI recognition sequence. The forward primer MBC1HVR2 (SEQ ID No. 10) for the V domain of the H chain was designed so that it might hybridize with DNA encoding the 3'-side of J domain and it might encode 5'-side of C domain and might have ApaI and SmaI recognition sequence.

PCR was performed using TaKaRa Ex Taq (TAKARA SHUZO) and the appended buffer solution under the condition where 0.6 μg of plasmid MBC1H/pUC19 as a template DNA, 50 pmoles each of MBC1HVS2 and MBC1HVR2 as primers, 2.5 U of TaKaRa Ex Taq and 0.25 mM dNTP were contained in 50 μl of the reaction mixture solution with 30 times of the temperature cycle consisting of 94° C. for 1 minute, 55° C. for 1 minute and 72° C. for 2 minutes while the solution was blanketed with 50 μl of a mineral oil layer. The DNA fragments amplified by the PCR method as mentioned above were separated by agarose gel electrophoresis using 1% Sea Kem GTG agarose (FMC Bio. Products). A piece of agarose which contains a DNA fragment of 456 bp length was excised, and the DNA fragment was purified using GENECLEAN II Kit (BIO101) according to the instructions appended to the kit. The purified DNA was precipitated with ethanol, and then dissolved in 10 mM Tris-HCl (pH 7.4) and 20 μl of 1 mM EDTA solution.

One (1) μl of the obtained DNA solution was digested with restriction enzymes EcoRI and SmaI (TAKARA SHUZO) at 37° C. for 1 hour. This digested mixture was extracted with phenol and chloroform, and DNA was collected by ethanol precipitation.

The EcoRI-SmaI DNA fragment containing a gene encoding the mouse H chain V domain prepared as mentioned above was subcloned into pUC19 vector prepared by digesting with EcoRI and SmaI. In order to confirm the nucleotide sequence of this plasmid, M13 Primer M4 and M13 Primer RV were used as primers with Dye Terminator Cycle Sequencing kit (Perkin-Elmer) and the nucleotide sequence was determined using DNA Sequencer 373A (Perkin-Elmer). The plasmid containing a gene encoding the mouse H chain V domain originating from hybridoma #23-57-137-1 which has the correct nucleotide sequence and EcoRI and Hind III recognition sequences and Kozak sequence at 5'-side and ApaI and SmaI recognition sequences at 3'-side was designated as MBC1Hv/pUC19.

(iii) Construction of Expression Vector of Chimeric Antibody H Chain cDNA which contains Cγ1 of human H chain C domain was prepared as follows. That is, mRNAs were prepared from the CHO cell into which an expression vector DHFR-ΔE-RVh-PM-1-f (WO92/19759) encoding a humanized PM1 antibody H chain V domain and a genome DNA of human antibody H chain C domain IgG1 (N. Takahashi, et al., Cell 29, and 671-679 1982) as well as an expression vector RV1-PM1a (WO92/19759) encoding a humanized PM1 antibody L chain V domain and a genome DNA of human antibody L chain K chain C domain were introduced. The cloning of the cDNA which contained a humanized PM1 antibody H chain V domain and Cγ1 of human antibody C domain was carried out by RT-PCR method, and subcloning was carried out to Hind III and BamHI sites of pUC19. After confirming the nucleotide sequence, the plasmid with the correct sequence was designated as pRVh-PM1f-cDNA.

An expression vector from which the Hind III site between the SV40 promoter on DHFR-ΔE-RVh-PM-1-f and DHFR gene and the EcoRI site between the EF-1alpha promoter and a humanized PM1 antibody H chain V domain were deleted was prepared, and used for the construction of the expression vector of cDNA which contains humanized PM1 antibody H chain V domain and Cγ1 of human antibody C domain.

After digesting pRVh-PM1f-cDNA with BamHI, Klenow fragment was used to form a blunt end, and digestion with Hind III further was effected to prepare a Hind III-BamHI blunt end fragment. The Hind III-BamHI blunt end fragment was ligated to the above-mentioned expression vector prepared by digesting DHFR-ΔE-RVh-PM1-f from which the Hind III site and the EcoRI were deleted with Hind III and SmaI, and an expression vector RVh-PM1f-cDNA containing cDNA encoding humanized PM1 antibody H chain V domain and Cγ1 of human antibody C domain was constructed.

After digesting the expression vector RVh-PM1f-cDNA containing cDNA encoding humanized PM1 antibody H chain V domain and Cγ1 of human antibody C domain with ApaI and BamHI, DNA fragments including an H chain C domain were collected, and introduced into MBC1Hv/pUC19 prepared by digesting with ApaI and BamHI. The thus prepared plasmid was designated as MBC1HcDNA/pUC19. This plasmid contains cDNA to which encodes H chain V domain of a mouse antibody and Cγ1 of human antibody C domain and has EcoRI and Hind III recognition sequences at 5'-end, and has BamHI recognition sequence at 3'-end.

An expression vector obtained by digesting the plasmid MBC1 HcDNA/pUC19 with EcoRI and BamHI and digesting the obtained DNA fragment containing the nucleotide sequence which encodes the H chain of the chimeric antibody with EcoRI and BamHI was introduced into the expression vector pCOS1. The thus obtained expression plasmid of the chimeric antibody was designated as MBC1HcDNA/pCOS1. The expression vector pCOS1 was constructed by deleting the antibody gene by EcoRI and SmaI digestion from HEF-PMh-g γ1 (see WO92/19759) and ligating an EcoRI-NotI-BamHI adapter (TAKARA SHUZO).

Furthermore, in order to produce the plasmid for using for expression in a CHO cell, an expression plasmid pCHO1 prepared by digesting the plasmid MBC1 HcDNA/pUC19 with EcoRI and BamHI and digesting the obtained DNA fragment containing the nucleotide sequence which encodes the H chain of the chimeric antibody with EcoRI and BamHI was introduced into the expression plasmid pCHO1. The thus obtained expression plasmid of the chimeric antibody was designated as MBC1HcDNA/pCHO1. The expression vector pCHO1 was constructed by deleting the antibody gene by EcoRI and SmaI digestion from DHFR-ΔE-rvH-PM1-f (see WO92/19759) and ligating an EcoRI-NotI-BamHI adapter (TAKARA SHUZO).

(2) Construction of Human L Chain Constant Domain (i) Preparation of Cloning Vector In order to construct a pUC19 vector including human L chain constant domain, a Hind III site deleted pUC19 vector was prepared. Two (2) μg of pUC19 vector was digested in 20 μl of reaction mixture solution containing 20 mM Tris-HCl (pH 8.5), 10 mM $MgCl_2$, 1 mM DTT, 100 mM KCl, and 8 U of Hind III (TAKARA SHUZO) at 37° C. for 1 hour. The digestive mixture solution was extracted with phenol and chloroform, and DNA was collected by ethanol precipitation.

The collected DNA was reacted at room temperature for 20 minutes in 50 μl of a reaction mixture solution containing 50 mM Tris-HCl (pH 7.5), 10 mM $MgCl_2$, 1 mM DTT, 100 mM NaCl, 0.5 mM dNTP, and 6 U of Klenow fragment (GIBCO BRL) to form a blunt end. The reaction mixture solution was extracted with phenol and chloroform, and the vector DNA was collected by ethanol precipitation.

The collected vector DNA was reacted at 16° C. for 2 hours in 10 μl of reaction mixture solution containing 50 mM Tris-HCl (pH 7.6), 10 mM $MgCl_2$, 1 mM ATP, 1 mM DTT, 5% (v/v) polyethyleneglycol-8000 and 0.5 U of T4 DNA ligase (GIBCO BRL) to effect self-ligation. After 5 μl of the reaction mixture solution was added to 100 μl of *E. coli* JM109 competent cell (NIPPON GENE), the solution was allowed to stand still for 30 minutes on ice, at 42° C. for 1 minute and further allowed to stand still for 1 minute on ice. After 500 μl of SOC culture medium was added, incubation at 37° C. for 1 hour was carried out, the solution was spread on 2xYT agar culture medium (containing 50 μg/ml of ampicillin) on the surface of which were applied X-gal and IPTG (Molecular Cloning: A Laboratory Manual, Sambrook, et al., Cold Spring Harbor Laboratory Press, and 1989), and cultured at 37° C. overnight to obtain transformant.

The transformant was cultured on 20 ml of 2xYT agar culture medium containing 50 μg/ml of ampicillin at 37° C. overnight, and plasmid DNA was purified from the cell body fraction using Plasmid Mini Kit (QIAGEN) according to the appended instructions. The purified plasmid was digested with Hind III and the plasmid in which the deletion of Hind III site was confirmed was designated as pUC19 ΔHind III.

(ii) Construction of Gene Encoding Human L Chain λ Chain Constant Domain

As the human antibody L chain λ chain C domain, at least four isotypes of Mcg+Ke+Oz−, Mcg−Ke−Oz−, Mcg−Ke−Oz+ and Mcg−Ke+Oz− are known (P. Dariavach, et al., Proc. Natl. Acad. Sci. USA, 84, 9074-9078, 1987). As a result of searching in the EMBL database a human antibody L chain λ chain C domain which has homology to the #23-57-137-1 mouse L chain λ chain C domain, the human antibody L chain λ chain of the isotype Mcg+Ke+Oz− (accession No. X57819) (P. Dariavach, et al., Proc. Natl. Acad. Sci. USA, 84, 9074-9078, and 1987) showed the highest homology and the homology with # 23-57-137-1 mouse L chain λ chain C domain was 64.4% in amino acid sequence and 73.4% in the nucleotide sequence.

Then, the construction of the gene encoding this human antibody L chain λ chain C domain was performed using PCR method. Synthesis of each primer was performed using 394 DNA/RNA synthesizer (ABI company). HLAMB1 (SEQ ID No. 11) and HLAMB3 (SEQ ID No. 13) have sense DNA sequence, and HLAMB2 (SEQ ID No. 12) and HLAMB4 (SEQ ID No. 14) have antisense DNA sequence, and they have a complementary sequence of 20 to 23 bp from the both ends of each primer.

The external primers HLAMBS (SEQ ID No. 15) and HLAMBR (SEQ ID No. 16) have homologous sequences to HLAMB1, HLAMB4, respectively, and HLAMBS contains EcoRI, Hind III, and BlnI recognition sequences, and HLAMBR contains EcoRI recognition sequence, respectively. The reaction of HLAMB1-HLAMB2 and HLAMB3-HLAMB4 was performed in the first PCR. After the reaction, they were mixed in the same amount and the assembly was performed by the second PCR. Furthermore, the external primers HLAMBS and HLAMBR were added and full length DNA was amplified by the third PCR.

PCR was performed using TaKaRa Ex Taq (TAKARA SHUZO) according to the appended instructions. In the first PCR, 100 µl of the reaction mixture solution containing 5 pmoles of HLAMB1, 0.5 pmole of HLAMB2 and 5 U of TaKaRa Ex Taq (TAKARA SHUZO) or 100 µl of the reaction mixture solution containing 0.5 pmole of HLAMB3, 0.5 pmole of HLAMB4 and 5 U of TaKaRa Ex Taq (TAKARA SHUZO) were used and blanketed with 50 µl of a mineral oil layer and 5 times of the temperature cycle consisting of 94° C. for 1 minute, 60° C. for 1 minute and 72° C. for 1 minute were performed.

The second PCR was performed by mixing 50µ/l each of the reaction liquids, and carrying out 3 times of the temperature cycle consisting of 94° C. for 1 minute, 60° C. for 1 minute and 72° C. for 1 minute while blanketed with 50 µl of a mineral oil layer.

The third PCR was performed by adding 50 pmoles each of external primers HLAMBS and HLAMBR to the reaction liquid, and carrying out 30 times of the temperature cycle consisting of 94° C. for 1 minute, 60° C. for 1 minute and 72° C. for 1 minute.

After carrying out electrophoresis of the DNA fragment of the third PCR product on a 3% low melting point agarose gel (NuSieve GTG Agarose and FMC), GENECLEANII Kit (BIO101) was used, and the fragment was collected and purified from the gel according to the appended instructions.

The obtained DNA fragment was digested at 37° C. for 1 hour in 20 µl of the reaction mixture solution containing 50 mM Tris-HCl (pH 7.5), 10 mM $MgCl_2$, 1 mM DTT, 100 mM NaCl, and 8 U of EcoRI (TAKARA SHUZO). After the digestive mixture solution was extracted with phenol and chloroform, DNA was collected by ethanol precipitation and dissolved in 10 mM Tris-HCl (pH 7.4) and 8 µl of 1 mM EDTA solution.

Similarly, 0.8 µg of plasmid pUC19 ΔHind III was digested with EcoRI, extracted with phenol and chloroform and collected by ethanol precipitation. The digested plasmid pUC19 ΔHind III was reacted at 37° C. for 30 minutes in 50 µl of the reaction mixture solution containing 50 mM Tris-HCl (pH 9.0), 1 mM $MgCl_2$ and alkaline phosphatase (*E. coli* C75, TAKARA SHUZO), and dephosphorylation treatment (BAP treatment) was carried out. After the reaction liquid was extracted with phenol and chloroform, DNA was collected by ethanol precipitation and dissolved in 10 mM Tris-HCl (pH 7.4) and 10 µl of 1 mM EDTA solution.

One (1) µl of the plasmid pUC19 ΔHind III treated with BAP and 4 µl of the above-mentioned PCR product were ligated using DNA Ligation Kit Ver. 2 (TAKARA SHUZO), and the *E. coli* JM109 competent cell was transformed therewith. The obtained transformant was cultured overnight in 2 ml of 2xYT culture media containing 50 µg/ml of ampicillin, and the plasmid was purified using QIAprep Spin Plasmid Kit (QIAGEN) from the cell body fraction.

As for the above-mentioned cloned plasmid, the cloned nucleotide sequence of DNA was confirmed. 373A DNA sequencer (ABI company) was used for the determination of nucleotide sequence and M13 Primer M4 and M13 Pricer RV (TAKARA SHUZO) were used as primers. Consequently, it became clear that 12 bp was deleted in the inside of the cloned DNA. The plasmid containing this DNA was designated as CλΔ/pUC19. Then, primers HCLMS (SEQ ID No. 17) and HCLMR (SEQ ID No. 18) were newly synthesized for compensating the portion, and the correct DNA was again constructed by PCR.

The first PCR was performed with the plasmid CλΔ/pUC19 which contains deleted DNA as a template using primers HLAMBS, HCLMR, HCLMS and HLAMB4. The PCR product was purified, respectively and the assembly was performed by the second PCR. Furthermore, external primers HLAMB and HLAMBS4 were added, and full length DNA was amplified by the third PCR.

In the first PCR, 100 µl of the reaction mixture solution containing 0.1 µg of CλΔ/pUC19 as a template, 50 pmoles each of primers HLAMBS and HCLMR, or 50 pmoles each of primers HCLMS and HLAMB4 and 5 U of TaKaRa Ex Taq (TAKARA SHUZO) was used and blanketed with 50 µl of a mineral oil layer and 30 times of the temperature cycle consisting of 94° C. for 1 minute, 60° C. for 1 minute and 72° C. for 1 minute were performed.

After carrying out electrophoresis of the PCR products HLAMBS-HCLMR (236 bp) and HCLMS-HLAMB4 (147 bp) on a 3% low melting point agarose gel, respectively, GENECLEANII Kit (BIO101) was used, and the products were collected and purified from the gel. In the second PCR, 20 µl of the reaction mixture solution containing 40 ng each of the purified DNA fragments, 1 U of TaKaRa Ex Taq (TAKARA SHUZO) was used and blanketed with 25 µl of a mineral oil layer and 5 times of the temperature cycle consisting of 94° C. for 1 minute, 60° C. for 1 minute and 72° C. for 1 minute were performed.

In the third PCR, 100 µl of the reaction mixture solution containing 2 µl of the second PCR reaction liquid, 50 pmoles each of external primers HLAMBS and HLAMB4, and 5 U of TaKaRa Ex Taq (TAKARA SHUZO) was used and blanketed with 50 µl of a mineral oil layer. PCR was performed with 30 times of the temperature cycle consisting of 94° C. for 1 minute, 60° C. for 1 minute and 72° C. for 1 minute. After carrying out electrophoresis of the DNA fragment of 357 bp, which is the third PCR product, on a 3% low melting point agarose gel, GENECLEANII Kit (BIO101) was used, and the products were collected and purified from the gel.

0.1 µg of the obtained DNA fragment was digested with EcoRI and subcloned into pUC19ΔHind III subjected to BAP treatment. *E. coli* JM109 competent cells were transformed, cultured overnight in 2 ml of 2xYT culture media containing 50 µg/ml ampicillin, and the plasmid was purified using QIAprep Spin Plasmid Kit (QIAGEN) from the cell body fraction. The nucleotide sequence was determined in 373A DNA sequencer (ABI company) using M13 Primer M4 and M13 Primer RV (TAKARA SHUZO) for the purified plasmid. The plasmid which was confirmed to have the correct nucleotide sequence without deletion was designated as Cλ/pUC19.

(iii) Construction of Gene Encoding Human L Chain κ Chain Constant Domain

The fragment of DNA encoding L chain κ chain C domain was cloned using the PCR method from plasmid HEF-PM1k-gk (WO92/19759). The forward primer HKAPS (SEQ ID No.

19) synthesized using 394 DNA/RNA synthesizer (ABI company) was designed so as to have EcoRI, Hind III and BlnI recognition sequences and reverse primer HKAPA (SEQ ID No. 20) was designed so as to have EcoRI recognition sequence.

100 μl of the reaction mixture solution containing 0.1 μg of plasmid HEF-PM1k-gk used as a template, 50 pmoles each of primers HKAPS and HKAPA, and 5 U of TaKaRa Ex Taq (TAKARA SHUZO) was used and blanketed with 50 μl of a mineral oil layer. PCR was performed with 30 times of the temperature cycle consisting of 94° C. for 1 minute, 60° C. for 1 minute and 72° C. for 1 minute. After carrying out electrophoresis of the PCR product of 360 bp on a 3% low melting point agarose gel, GENECLEANII Kit (BIO101) was used, and the product were collected and purified from the gel.

After digesting the obtained DNA fragment with EcoRI, the digested fragment was subcloned into pUC19 ΔHind III which had been subjected to BAP treatment. $E.\ coli$ JM109 competent cells were transformed, cultured overnight in 2 ml of 2xYT culture media containing 50 μg/ml ampicillin, and the plasmid was purified using QIAprep Spin Plasmid Kit (QIAGEN) from the cell body fraction.

The nucleotide sequence of the purified plasmid was determined on 373A DNA sequencer (ABI company) using M13 Primer M4 and M13 Primer RV (TAKARA SHUZO). The plasmid which was confirmed to have the correct nucleotide sequence was designated as CK/pUC19.

(3) Construction of Chimeric Antibody L Chain Expression Vector

The chimera #23-57-137-1 antibody L chain expression vector was constructed. The pUC19 vectors encoding the chimera #23-57-137-1 antibody L chain V domain and L chain λ chain, or L chain K chain constant domain, respectively were prepared by linking the gene encoding the #23-57-137-1 L chain V domain to Hind III and BlnI sites which are just before the human antibody constant domain of plasmids Cλ/pUC19 and Cκ/pUC19. By EcoRI digestion, the chimeric antibody L chain gene was excised and subcloned into HEF expression vector.

That is, the cloning of the #23-57-137-1 antibody L chain V domain was carried out using the PCR method from the plasmid MBC1L24. Synthesis of each primer was performed using 394 DNA/RNA synthesizer (ABI company).

The reverse primer MBCCHL1 (SEQ ID No. 21) was designed so as to have Hind III recognition sequence and Kozak sequence (Kozak, M. et al., J. Mol. Biol. 196, 947-1987) and the forward primer MBCCHL3 (SEQ ID No. 22) was designed so as to have BglII and EcoRI recognition sequences.

PCR was performed using 100 μl of the reaction mixture solution containing 10 mM Tris-HCl (pH 8.3), 50 mM KCl, 1.5 mM $MgCl_2$, 0.2 mM dNTP, 0.1 μg MBC1L24 and 50 pmoles each of MBCCHL1 and MBCCHL3 as primers and 1 μl of AmpliTaq (PERKIN ELMER) and by carrying out 30 times of the temperature cycle consisting of 94° C. for 45 seconds, 60° C. for 45 seconds and 72° C. for 2 minutes while blanketed with 50 μl of a mineral oil layer.

After carrying out electrophoresis of the PCR product of 444 bp on a 3% low melting point agarose gel, GENECLEAN II kit (BIO101) was used, and the product were collected and purified from the gel, and dissolved in 10 mM Tris-HCl (pH 7.4), 20 μl of 1 mM EDTA solution. One (1) μl of the PCR product was digested at 37° C. for 1 hour in 20 μl of a reaction mixture solution which contained 10 mM Tris-HCl (pH 7.5), 10 mM $MgCl_2$, 1 mM DTT, 50 mM NaCl, 8 U of Hind III (TAKARA SHUZO) and 8 U of EcoRI (TAKARA SHUZO), respectively. The digest mixture solution was extracted with phenol and chloroform, and DNA was collected by ethanol precipitation, and dissolved in 10 mM Tris-HCl (pH 7.4) and 8 μl of 1 mM EDTA solution.

Plasmid pUC19 1 μg was similarly digested with Hind III and EcoRI, extracted with phenol and chloroform, collected by ethanol precipitation, and BAP treatment was carried out with alkaline phosphatase ($E.\ coli$ C75 and TAKARA SHUZO). After the reaction liquid was extracted with phenol and chloroform, and DNA was collected by ethanol precipitation, it was dissolved in 10 mM Tris-HCl (pH 7.4) and 10 μl of 1 mM EDTA solution.

One (1) μl plasmid pUC19 subjected to BAP treatment and 4 μl of previous PCR product was ligated using DNA Ligation Kit Ver. 2 (TAKARA SHUZO), and $E.\ coli$ JM109 competent cell (NIPPON GENE) was transformed in the similar manner as above. This was spread on 2xYT agar culture medium containing 50 μg/ml of ampicillin, and cultured at 37° C. overnight. The obtained transformant was cultured at 37° C. overnight in 2 ml of 2xYT culture media containing 50 μg/ml of ampicillin. The plasmid was purified using QIAprep Spin Plasmid Kit (QIAGEN) from the cell body fraction. After the nucleotide sequence was determined, the plasmid which has the correct nucleotide sequence was designated as CHL/pUC19.

One (1) μg each of plasmids Cλ/pUC19 and Cκ/pUC19 was separately digested at 37° C. for 1 hour in 20 μl of the reaction mixture solution containing 20 mM Tris-HCl (pH 8.5), 10 mM $MgCl_2$, 1 mM DTT, and 100 mM KCl and 8 U of Hind III (TAKARA SHUZO) and 2 U of BlnI (TAKARA SHUZO). After the digested mixture solution was extracted with phenol and chloroform and DNA was collected by ethanol precipitation, BAP treatment was performed at 37° C. for 30 minutes. The reaction liquid was extracted with phenol and chloroform, DNA was collected by ethanol precipitation, and dissolved in 10 mM Tris-HCl (pH 7.4) and 10 μl of 1 mM EDTA solution.

Eight (8) μg was similarly digested with Hind III and BlnI from plasmid CHL/pUC19 containing #23-57-137-1 L chain V domain. After carrying out electrophoresis of the obtained DNA fragment of 409 bp on a 3% low melting point agarose gel, collected and purified from the gel using GENECLEA-NII Kit (BIO101) and dissolved in 10 mM Tris-HCl (pH 7.4) and 10 μl of 1 mM EDTA solution.

Four (4) μl of this L chain V domain DNA was subcloned into 1 μl each of plasmid Cλ/pUC19 or Cκ/pUC19 subjected to BAP treatment, and $E.\ coli$ JM109 competent cells were transformed. They were cultured overnight in 3 ml of 2xYT culture media containing 50 μg/ml ampicillin, and the plasmid was purified using QIAprep Spin Plasmid Kit (QIAGEN) from the cell body fraction. These were designated as plasmids MBC1L(λ)/pUC19 and MBC1L(κ)/pUC19, respectively.

After digesting plasmids MBC1L(λ)/pUC19 and MBC1L(κ)/pUC19 by EcoRI separately and carrying out electrophoresis on a 3% low melting point agarose gel, GENECLEANII Kit (BIO101) was used, and the DNA fragment of 743 bp was collected, purified from the gel, and dissolved in 10 mM of Tris-HCl (pH 7.4) and 10 μl of 1 mM EDTA solution.

2.7 μg of plasmid HEF-PM1k-gk was digested with EcoRI as an expression vector, extracted with phenol and chloroform and DNA was collected by ethanol precipitation. After carrying out BAP treatment of the collected DNA fragment, electrophoresis was carried out on a 1% low melting point agarose gel, GENECLEANII Kit (BIO101) was used, and the DNA fragment of 6561 bp was collected and purified from the gel, dissolved in 10 mM Tris-HCl (pH 7.4) and 10 μl of 1 mM EDTA solution.

Two (2) μl of HEF vector subjected to BAP treatment was linked to 3 μl each of EcoRI fragments of the above-mentioned plasmid MBC1L(λ) or MBC1L(κ) and transformed into E. coli JM109 competent cells. They were cultured in 2 ml of 2xYT culture media containing 50 μg/ml of ampicillin, and the plasmid was purified using QIAprep Spin Plasmid Kit (QIAGEN) from the cell body fraction.

The purified plasmid was digested at 37° C. for 1 hour in 20 μl of the reaction mixture solution containing 20 mM Tris-HCl (pH 8.5), 10 mM $MgCl_2$, 1 mM DTT, 100 mM KCl, 8 U of Hind III (TAKARA SHUZO) and 2 U of PvuI (TAKARA SHUZO). The plasmid inserted in the right direction results in a digested fragment of 5104/2195 bp while the plasmid inserted in the wrong direction results in a digested fragment of 4378/2926 bp and the plasmids inserted in the right direction were designated as MBC1L(λ)/neo and MBC1L(κ)/neo, respectively.

(4) Transfection of COS-7 Cells

In order to evaluate the antigen binding activity and neutralization activity of a chimeric antibody, the above-mentioned expression plasmid was constructed to express transiently in COS-7 cell.

That is, transient expression of a chimeric antibody is effected by simultaneous transducing the combination of plasmids MBC1HcDNA/pCOS1 and MBC1L(λ)/neo, or MBC1HcDNA/pCOS1 and MBC1L(κ)/neo into COS-7 cell by electroporation using Gene Pulser equipment (Bio Rad). Ten (10) μg each of plasmid DNA was added to 0.8 ml of COS-7 cells suspended at a cell concentration of $1 \times 10^7$ cell/ml in PBS (−), and the pulse was given to them by the capacitance of 1,500V and 25 μF. After allowed to recover at room temperature for 10 minutes, the cells subjected to electroporation processing were suspended in a DMEM culture medium (GIBCO) containing 2% of Ultra Low IgG Fetal Bovine Serum (GIBCO), and cultured in a $CO_2$ incubator using 10 cm culturing plate. Culturing supernatant was collected after culturing 72 hours, centrifugal separation removed the cell fragments, and the sample of ELISA was prepared.

Purification of the chimeric antibody from the culture supernatant of COS-7 cells was performed using AffiGel Protein A MAPSII kit (BioRad) according to the instructions appended to the kit.

(5) ELISA (i) Measurement of Antibody Concentration

An ELISA plate for antibody concentration measurement was prepared as follows. Each well of a 96 well plate for ELISA (Maxisorp, NUNC) is coated with 100 μl of goat anti-man IgG antibody (TAGO) adjusted to 1 μg/ml concentration with the coating buffer (0.1M NaHCO3, 0.02% NaN3), blocked with 200 μl of a dilution buffer (50 mM Tris-HCl, 1 mM $MgCl_2$, 0.1M NaCl, 0.05% Tween20, 0.02% NaN3 and 1% bovine serum albumin (BSA), pH 7.2), culture supernatant of the COS cells in which the chimeric antibody was expressed or the purified chimeric antibody was stepwise diluted and added to each well. After the plate was incubated at room temperature for 1 hour and washed with PBS-Tween20, 100 μl of alkaline phosphatase (TAGO) conjugated goat anti-man IgG antibody was added. After the plate was incubated at room temperature for 1 hour and washed with PBS-Tween20, 1 mg/ml of a substrate solution (Sigma104, p-nitrophenylphosphate, SIGMA) was added, and, next, 405 nm absorption was measured with a micro plate reader (Bio Rad). As the standard for concentration measurement, Hu IgG1λ Purified (The Binding Site) was used.

(ii) Measurement of Antigen Binding Ability

The ELISA plate for antigen binding measurement was prepared as follows. Each well of a 96 well plate for ELISA was coated with 100 μl of human PTHrP(1-34) (Peptide Research Institute) adjusted to 1 μg/ml concentration by the coating buffer. After blocking with 200 μl of the dilution buffer, culture supernatant of the COS cells in which the chimeric antibody was expressed or the purified chimeric antibody was stepwise diluted and added to each well. After the plate was incubated at room temperature and washed with PBS-Tween20, 100 μl of alkaline phosphatase (TAGO) conjugated goat anti-man IgG antibody was added. After the plate was incubated at room temperature and washed with PBS-Tween20, 1 mg/ml of a substrate solution (Sigma104, p-nitrophenylphosphate, SIGMA) was added, and, next, 405 nm absorption was measured with a micro plate reader (Bio Rad).

Consequently, it was shown that the chimeric antibody had a binding ability to human PTHrP (1-34) and had a correct structure of the cloned mouse antibody V domain. In addition, since the binding ability to PTHrP (1-34) of an antibody did not change even if the L chain C domains were either λ chain or κ chain in the chimeric antibody, the L chain C domain of the humanized antibody was constructed using the humanized antibody L chain λ chain.

(6) Establishment of Stably Producing CHO Cell Line

In order to establish a cell line stably producing a chimeric antibody, the above-mentioned expression plasmid was introduced into the CHO cell (DXB11).

That is, establishment of stably producing a chimeric antibody is effected by simultaneous transducing the combination of expression plasmids for CHO cells MBC1HcDNA/pCHO1 and MBC1L(λ)/neo or MBC1HcDNA/pCHO1 and MBC1L(κ)/neo into CHO cells by electroporation using Gene-Pulser equipment (Bio Rad). Each expression vector was cleaved with a restriction enzyme PvuI to produce a linear DNA, and after phenol and chloroform extraction, the DNA was collected by ethanol precipitation and used for electroporation. Ten (10) μg each of plasmid DNA was added to 0.8 ml of CHO cells suspended at a cell concentration of $1 \times 10^7$ cell/ml in PBS (−), and the pulse was given to them by the capacitance of 1,500V and 25 μF. After allowed to recover at room temperature for 10 minutes, the cells subjected to electroporation processing were suspended in a MEM-α culture medium (GIBCO) supplemented with 10% of Fetal Bovine Serum (GIBCO) and cultured in a $CO_2$ incubator using three 96 well plates (Falcon). The culture medium was replaced by a selection culture medium which is MEM-α culture medium supplemented with 10% Fetal Bovine Serum (GIBCO) and 500 mg/ml GENETICIN (G418Sulfate, GIBCO) and free from ribonucleosides and deoxyribonucleosides MEM-α culture medium (GIBCO) on the next day after starting the culturing, and the cells into which the antibody gene was introduced were selected. In about two weeks after the selection culture medium was replaced, the cells were observed under the microscope and after favorable cell proliferation was recognized, the amount of antibody production was measured by the above-mentioned antibody concentration measurement ELISA, and the cells with much antibody production were selected.

Culturing of the established cell line stably producing an antibody was expanded, and extensive culturing was performed using a MEM medium supplemented with 2% of Ultra Low IgG Fetal Bovine Serum by roller bottle and free from ribonucleosides and deoxyribonucleoside. Culturing supernatant was collected on the 3rd or the 4th days after culturing, and the 0.2μ filter (Millipore) may be used to removed the cell fragments.

Purification of the chimeric antibody from culture supernatant of CHO cells was performed using the POROS protein A column (PerSeptive Biosystems) with ConSep LC100 (Millipore) according to the appended instructions, and subjected to measurement of neutralization activity and the drug efficacy in hypercalcemia model animal. The concentration and antigen binding activity of the obtained purified chimeric antibody were measured by the above-mentioned ELISA system.

REFERENTIAL EXAMPLE 4

Construction of Humanized Antibody (1) Construction of Humanized Antibody H Chain
    (i) Construction of Humanized H Chain V Domain
    H chain of humanized #23-57-137-1 antibody H chain was prepared by CDR-grafting in PCR method. Six PCR primers were used for the preparation of the humanized antibody #23-57-137-1 antibody H chain (version "a") having FR derived from human antibody S31679 (NBRF-PDB, Cuisinier A. M. et al., Eur. J. Immunol., 23, 110-118, 1993). CDR-grafting primers MBC1HGP1 (SEQ ID No. 23) and MBC1HGP3 (SEQ ID No. 24) have sense DNA sequence, and CDR grafting primers MBC1HGP2 (SEQ ID No. 25) and MBC1HGP4 (SEQ ID No. 26) have antisense DNA sequence, and each of them has a complementary sequence of 15 to 21 bp from the both ends of primer, respectively. External primers MBC1HVS1 (SEQ ID No. 27) and MBC1HVR1 (SEQ ID No. 28) have homology to CDR grafting primers MBC1HGP1 and MBC1HGP4.

CDR-grafting primers MBC1HGP1, MBC1HGP2, MBC1HGP3 and MBC1HGP4 were separated using urea denaturing polyacrylamide gel (Molecular Cloning: A Laboratory Manual, Sambrook et al., Cold Spring Harbor Laboratory Press, 1989), and extraction from the gel was performed by the crush and soak method (Molecular Cloning: A Laboratory Manual, Sambrook et al., Cold SpringHarbor Laboratory Press, 1989).

That is, 1 nmole each of CDR-grafting primers was separated on 6% denaturing polyacrylamide gel, respectively, ultraviolet ray was irradiated on silica gel thin layer plate, identification of the DNA fragment of the target size was performed, and the fragment was collected from the gel by the crush and soak method, and dissolved in 20 μl of 10 mM Tris-HCl (pH 7.4) and 1 mM EDTA solution. PCR was performed using TaKaRa Ex Taq (TAKARA SHUZO) and the appended buffer solution under the condition where 1 μl each of CDR-grafting primers MBC1HGP1, MBC1HGP2, MBC1HGP3 and MBC1HGP4 prepared as mentioned above, 0.25 mM of dNTP and 2.5 U of TaKaRa Ex Taq were contained in 100 μl of the reaction mixture solution with 5 times of the temperature cycle consisting of 94° C. for 1 minute, 55° C. for 1 minute and 72° C. for 1 minute and further 30 times of the temperature cycle after 50 pmoles of external primers MBC1HVS1 and MBC1HVR1 were added. The DNA fragments amplified by the PCR method as mentioned above were separated by agarose gel electrophoresis using 4% Nu Sieve GTG agarose (FMC Bio. Products).

A piece of agarose containing the DNA fragment of 421 bp length was excised, and the DNA fragment was purified using GENECLEANII Kit (BIO101) according to the instructions appended to the kit. After the purified DNA was precipitated with ethanol, it was dissolved in 10 mM Tris-HCl (pH 7.4) and 20 μl of a 1 mM EDTA solution. The obtained PCR reaction mixture was subcloned into pUC19 prepared by digesting with BamHI and HindIII, and the nucleotide sequence was determined. The plasmid which has the correct sequence was designated as hMBCHv/pUC19.

(ii) Construction of H Chain V Domain for Humanized H Chain cDNA

In order to ligate to cDNA of Cγ1 of human H chain C domain, the humanized H chain V domain constructed as mentioned above was modified by PCR method. The reverse primer MBC1HVS2 was designed so that it might hybridize with the sequence encoding the 5'-side of the leader sequence of V domain and it might have Kozak consensus sequence (Kozak M, et al., J. Mol. Biol. 196, 947-950, 1987), HindIII, and EcoRI recognition sequences. The forward primer MBC1HVR2 for V domain of the H chain was designed so that it might hybridize with the DNA sequence encoding the 3'-side of J domain and encode the 5'-side sequence of C domain and it might have ApaI and SmaI recognition sequences.

PCR was performed using TaKaRa Ex Taq (TAKARA SHUZO) and the appended buffer solution under the condition where 0.4 μg of hMBCHv/pUC19 of as a template DNA, 50 pmoles each of MBC1HVS2 and MBC1HVR2 as primers respectively, 2.5 U of TaKaRa Ex Taq and 0.25 mM of dNTP were contained with 30 times of the temperature cycle consisting of 94° C. for 1 minute, 55° C. for 1 minute and 72° C. for 1 minute. The DNA fragments amplified by PCR method were separated by agarose gel electrophoresis using 3% Nu Sieve GTG agarose (FMC Bio. Products).

A piece of agarose containing the DNA fragment of 456 bp length is excised, and the DNA fragment was purified using GENECLEANII Kit (BIO101) according to the instructions appended to the kit. After the purified DNA was precipitated with ethanol, it was dissolved in 10 mM Tris-HCl (pH 7.4) and 20 μl of a 1 mM EDTA solution. The obtained PCR reaction mixture was subcloned into pUC19 prepared by digesting with EcoRI and SmaI, and the nucleotide sequence was determined. The thus prepared plasmid which contains a gene encoding the mouse H chain V domain derived from hybridoma #23-57-137-1, and has EcoRI and HindIII recognition sequences and Kozak sequence at 5'-side and has ApaI and SmaI recognition sequences at 3'-side was designated as hMBC1Hv/pUC19.

(2) Construction of Expression Vector of Humanized Antibody H Chain

Plasmid RVh-PM1f-cDNA containing the sequence of hPM1 antibody H chain cDNA was digested with ApaI and BamHI, and the DNA fragment containing the H chain C domain was collected, and introduced into hMBC1 Hv/pUC19 prepared by digesting with ApaI and BamHI. The thus prepared plasmid was designated as hMBC1HcDNA/pUC19. This plasmid contains the H chain V domain of humanized #23-57-137-1 antibody, and Cγ1 of human H chain C domain and has EcoRI and HindIII recognition sequences at 5'-end and BamHI recognition sequence at 3'-end. The nucleotide sequence of humanized H chain version "a" contained in plasmid hMBC1HcDNA/pUC19 and the amino acid sequence corresponding thereto are shown in SEQ ID No. 58. In addition, the amino acid sequence of version a is shown in the SEQ ID No. 56.

The DNA fragment containing H chain sequence obtained by digesting hMBC1HcDNA/pUC19 with EcoRI and BamHI was introduced into an expression plasmid pCOS1 prepared by digesting with EcoRI and BamHI. The thus obtained expression plasmid of humanized antibody was designated as hMBC1HcDNA/pCOS1.

Furthermore, in order to prepare a plasmid for using for expression in a CHO cell, hMBC1HcDNA/pUC19 was digested with EcoRI and BamHI and the obtained DNA fragment containing H chain sequence was introduced into an expression plasmid pCHO1 prepared by digesting the DNA fragment with EcoRI and BamHI. The thus obtained expression plasmid of humanized antibody was designated as hMBC1HcDNA/pCHO1.

(3) Construction of L Chain Hybrid Variable Domain (i) Preparation of FR 1, 2/FR3, 4 Hybrid Antibody L chain gene in which FR domain of a humanized antibody and a mouse (chimeric) antibody was recombined was constructed, and each domain for the formation of a humanized antibody was evaluated. By using the restriction enzyme AflII cleaving site in CDR2, a hybrid antibody in which FR 1 and 2 are derived from a human antibody, and FR 3 and 4 are derived from a mouse antibody was prepared.

Ten (10) µg each of plasmids MBC1L(λ)/neo and hMBC1L(λ)/neo were digested at 37° C. for 1 hour in 100 µl of reaction mixture solution containing 10 mM Tris-HCl (pH 7.5), 10 mM MgCl$_2$, 1 mM DTT, 50 mM NaCl, 0.01% (w/v) BSA and 10 U of AflII(TAKARA SHUZO). Electrophoresis of the reaction liquid was carried out on a 2% low melting point agarose gel, a fragment of 6282 bp (designated as c1) and a fragment (designated as c2) of 1022 bp from plasmid MBC1L(λ)/neo, and a fragment of 6282 bp (designated as h1) and a fragment (designated as h2) of 1022 bp from plasmid hMBC1L(λ)/neo were collected and purified from the gel using GENECLEANII Kit (BIO101).

BAP treatment was performed on 1 µg each of c1 and h1 fragments collected. After DNA was extracted with phenol and chloroform and collected by ethanol precipitation, it was dissolved in 10 mM Tris-HCl (pH 7.4) and 10 µl of 1 mM EDTA solution.

One (1) µl each of c1 and h1 fragments subjected to BAP treatment were linked to 4 µl of h2 and c2 fragments, respectively, (4° C., overnight) and transformed into E. coli JM109 competent cells. They were cultured in 2 ml of 2xYT culture media which contains 50 µg/ml of ampicillin, and the plasmid was purified using QIAprep Spin Plasmid Kit (QIAGEN) from the cell body fraction.

The purified plasmids were digested at 37° C. for 1 hour in 20 µl of reaction mixture solution containing 10 mM Tris-HCl (pH 7.5), 10 mM MgCl$_2$, 1 mM DTT, 2 U of ApaLI(TAKARA SHUZO), 8 U of BamHI(TAKARA SHUZO) or 8 U of HindIII(TAKARA SHUZO)8 U. If c1-h2 is correctly linked, digested fragments of 5560/1246/498 bp should arise with ApaLI and digested fragments of 7134/269 bp should arise with BamHI/HindIII. Based on this, the plasmids were confirmed.

These were designated as human FR1, 2/mouse FR3, 4 and an expression vector encoding hybrid antibody L chain was designated as h/mMBC1L(λ)/neo. Because the clone of h1-c2 was not obtained, after recombining on a pUC vector, they were cloned to the HEF vector. Plasmid hMBC1Laλ/pUC19 containing a humanized antibody L chain V domain without amino acid substitution, plasmid hMBC1Ldλ/pUC19 containing the humanized antibody L chain V domain in which tyrosine at the 91st position (the 87th position of the amino acid number according to Kabat designation) in FR3 was replaced by isoleucine were used as templates.

Ten (10) µg each of plasmid MBC1L(λ)/pUC19, hMBC1Laλ/pUC19 and hMBC1Ldλ/pUC19 were digested at 37° C. for 1 hour in 30 µl of the reaction mixture solution containing 10 mM Tris-HCl (pH 7.5), 10 mM MgCl$_2$, 1 mM DTT, 50 mM NaCl, 0.01% (w/v) BSA, 16 U of HindIII and 4 U of AflII. Electrophoresis of the reaction liquid was carried out on a 2% low melting point agarose gel, DNA fragments of 215 bp (c2') from plasmid MBC1L(λ)/pUC19, 3218 bp (ha1', hd1') from plasmids hMBC1Laλ/pUC19 and hMBC1Ldλ/pUC19, respectively were collected and purified from the gel using GENECLEANII Kit (BIO101).

The fragments ha1' and hd1' were linked to the c2' fragment, separately, and transformed into E. coli JM109 competent cells. They were cultured in 2 ml of 2xYT culture media containing 50 µg/ml of ampicillin, and the plasmids were purified using QIAprep Spin Plasmid Kit (QIAGEN) from the cell body fraction. These were designated as plasmids m/hMBC1Laλ/pUC19 and m/hMBC1Ldλ/pUC19, respectively.

The obtained plasmids m/hMBC1Laλ/pUC19 and m/hMBC1Ldλ/pUC19 were digested with EcoRI. After carrying out electrophoresis of the DNA fragments of 743 bp on a 2% low melting point agarose gel, respectively, GENECLEANII Kit (BIO101) was used, and they were collected and purified from the gel and dissolved in 10 mM Tris-HCl (pH 7.4) and 20 µl of 1 mM EDTA solution.

Four (4) µl each of DNA fragments were linked to 1 µl of the above-mentioned HEF vector subjected to BAP treatment, and transformed into E. coli JM109 competent cells. They were cultured in 2 ml of 2xYT culture media containing 50 µg/ml of ampicillin, and the plasmids were purified using QIAprep Spin Plasmid Kit (QIAGEN) from the cell body fraction.

Each of the purified plasmids was digested at 37° C. for 1 hour in 20 µl of the reaction mixture solution containing 20 mM Tris-HCl (pH 8.5), 10 mM MgCl$_2$, 1 mM DTT, 100 mM KCl, 8 U of HindIII(TAKARA SHUZO) and 2 U of PvuI (TAKARA SHUZO). The plasmid inserted in the right direction results in a digested fragment of 5104/2195 bp while the plasmid inserted in the wrong direction results in a digested fragment of 4378/2926 bp, and the plasmids were thus confirmed. The expression vectors encoding a mouse FR1, 2/human FR3, 4 hybrid antibody L chain, respectively were designated as m/hMBC1Laλ/neo and m/hMBC1Ldλ/neo.

(ii) Preparation of FR1/FR2 hybrid Antibody

By using the SnaBI cleaving site in CDR1, hybrid antibodies FR1 and FR2 were similarly prepared.

Ten (10) µg each of plasmid MBC1L(λ)/neo and h/mMBC1L (λ)/neo were digested at 37° C. for 1 hour in 20 µl of a reaction mixture solution containing 10 mM Tris-HCl (pH 7.9), 10 mM MgCl$_2$, 1 mM DTT, 50 mM NaCl, 0.01% (w/v) BSA, and 6 U of SnaBI(TAKARA SHUZO). Next, they were digested at 37° C. for 1 hour in 50 µl of a reaction mixture solution containing 20 mM Tris-HCl (pH 8.5), 10 mM MgCl$_2$, 1 mM DTT, 100 mM KCl, 0.01% (w/v) BSA and 6 U of PvuI.

After the reaction liquid was subjected to electrophoresis on a 1.5% low melting point agarose gel, each of DNA fragments of 4955 bp (m1) and 2349 bp (m2) from plasmid MBC1L(λ)/neo, 4955 bp (hm1) and 2349 bp (hm2) from plasmid h/mMBC1L(λ)/neo were collected and purified from the gel using GENECLEANII Kit (BIO101) and dissolved in 10 mM Tris-HCl (pH 7.4) and 40 µl of a 1 mM EDTA solution.

One (1) µl of m1 and hm1 fragments were linked to 4 µl of hm2 and m2 fragments, respectively, and transformed into E. coli JM109 competent cells. They were cultured in 2 ml of 2xYT culture media containing 50 µg/ml of ampicillin, and the plasmids were purified using QIAprep Spin Plasmid Kit (QIAGEN) from the cell fraction.

Each purified plasmid was digested at 37° C. for 1 hour in 20 μl of the reaction mixture solution containing 10 mM Tris-HCl (pH 7.5), 10 mM MgCl$_2$, 1 mM DTT, 8 U of ApaI (TAKARA SHUZO) or 2 U of ApaLI(TAKARA SHUZO).

If each fragment is linked correctly, digested fragments of 7304 bp by ApaI, 5560/1246/498 bp (m1-hm2) by ApaLI, 6538/766 bp by ApaI and 3535/2025/1246/498 bp (hm1-m2) by ApaLI should be generated, and the plasmids were thus confirmed. The expression vectors encoding human FR1/mouse FR2, 3, 4 hybrid antibody L chain was designated as hmmMBC1L(λ)/neo, and he expression vectors encoding mouse FR1/human FR2/mouse FR3, 4 hybrid antibody L chain was designated as mhmMBC1L(λ)/neo.

(4) Construction of Humanized Antibody L Chain

A humanized #23-57-137-1 antibody L chain was prepared by CDR-grafting in the PCR method. Six PCR primers were used for preparation of the humanized antibody #23-57-137-1 antibody L chain (version "a") having FR1, FR2 and FR3 derived from human antibody HSU03868 (GEN-BANK, Deftos M et al., Scand. J. Immunol., 39, 95-103, 1994) and FR4 derived from human antibody S25755 (NBRF-PDB).

CDR-grafting primers MBC1LGP4 (SEQ ID No. 29) and MBC1LGP3 (SEQ ID No. 30) have a sense DNA sequence, and CDR grafting primers MBC1LGP2 (SEQ ID No. 31) and MBC1LGP4 (SEQ ID No. 32) have an antisense DNA sequence, and each of them has a complementary sequence of 15 to 21 bp from the both ends of primer, respectively. External primers MBC1LVS1 (SEQ ID No. 33) and MBC1LVR1 (SEQ ID No. 34) have homology to CDR grafting primers MBC1LGP1 and MBC1LGP4.

CDR-grafting primers MBC1LGP1, MBC1LGP2, MBC1LGP3 and MBC1LGP4 were separated using urea denaturing polyacrylamide gel electrophoresis (Molecular Cloning: A Laboratory Manual, Sambrook et al., Cold Spring Harbor Laboratory Press, 1989), and extraction from the gel was performed by the crush and soak method (Molecular Cloning: A Laboratory Manual, Sambrook et al., Cold SpringHarbor Laboratory Press, 1989).

That is, 1 nmole each of CDR-grafting primers was separated on a 6% denaturing polyacrylamide gel, respectively, ultraviolet ray was irradiated on silica gel thin layer plate, identification of the DNA fragment of the desired size was performed, and the fragment was collected from the gel by the crush and soak method, and dissolved in 20 μl of 10 mM Tris-HCl (pH 7.4) and a 1 mM EDTA solution.

PCR was performed using TaKaRa Ex Taq (TAKARA SHUZO) and the appended buffer solution under the condition where 1 μl each of CDR-grafting primers MBC1LGP1, MBC1LGP2, MBC1LGP3 and MBC1LGP4 prepared as mentioned above, 0.25 mM of dNTP and 2.5 U of TaKaRa Ex Taq were contained in 100 μl of the reaction mixture solution with 5 times of the temperature cycle consisting of 94° C. for 1 minute, 55° C. for 1 minute and 72° C. for 1 minute and further 30 times of the temperature cycle after 50 pmoles of external primers MBC1LVS1 and MBC1LVR1 were added. The DNA fragments amplified by the PCR method as mentioned above were separated by agarose gel electrophoresis using 3% Nu Sieve GTG agarose (FMC Bio. Products).

A piece of agarose containing the DNA fragment of 421 bp length was excised, and the DNA fragment was purified using GENECLEANII Kit (BIO101) according to the instructions appended to the kit. The obtained PCR reaction mixture was subcloned into pUC19 prepared by digesting with BamHI and HindIII, and the nucleotide sequence was determined. The thus obtained plasmid was designated as hMBCL/pUC19. However, since the amino acid at the 104th position (the 96th position of the amino acid number according to Kabat designation) of CDR4 was arginine, correction primer MBC1LGP10R (SEQ ID No. 35) for correcting this to tyrosine was designed and synthesized. PCR was performed using TaKaRa Ex Taq (TAKARA SHUZO) and the appended buffer solution under the condition where 0.6 μg of plasmid hMBCL/pUC19 as a template DNA, 50 pmoles each of MBC1LVS1 and MBC1LGP10R as primers, 0.25 mM of dNTP and 2.5 U of TaKaRa Ex Taq were contained in 100 μl of the reaction mixture solution with 30 times of the temperature cycle consisting of 94° C. for 1 minute, 55° C. for 1 minute and 72° C. for 1 minute while blanketed with 50 μl of a mineral oil layer. Agarose gel electrophoresis using 3% Nu Sieve GTG agarose (FMC Bio. Products) separated the DNA fragments amplified by the PCR method.

A piece of agarose containing the DNA fragment of 421 bp length was excised, and the DNA fragment was purified using GENECLEANII Kit (BIO101) according to the instructions appended to the kit. The obtained PCR reaction mixture was subcloned into pUC19 prepared by digesting with BamHI and HindIII.

Since the correct sequence was obtained as a result of determining the nucleotide sequence using M13 Primer M4 primer and M13 Primer RV primer, this plasmid was digested with HindIII and BlnI, and 1% agarose gel electrophoresis separated the fragment of 416 bp. The DNA fragment was purified using GENECLEANII Kit (BIO101) according to instructions appended to the kit. The obtained PCR reaction mixture was introduced into plasmid Cλ/pUC19 prepared by digesting with HindIII and BlnI, and was designated as plasmid hMBC1Laλ/pUC19. This plasmid was digested with EcoRI and a sequence containing a sequence encoding the humanized L chain was introduced into a plasmid pCOS1 so that the start codon of the humanized L chain might be located downstream the EF1α promoter. The thus obtained plasmid was designated as hMBC1Laλ/pCOS1. The nucleotide sequence (including the corresponding amino acid) of the humanized L chain version "a" is shown in the SEQ ID No. 66. In addition, the amino acid sequence of version a is shown in the SEQ ID No. 47.

Version "b" was prepared using the mutagenesis by the PCR method. The version "b" was designed so that glycine at the 43rd position (the 43rd position of the amino acid number according to Kabat designation) might be changed to proline and the lysine at the 49th position (the 49th position of the amino acid number according to Kabat designation) might be changed into aspartic acid. PCR was performed with plasmid hMBC1Laλ/pUC19 as a template using mutagenic primer MBC1LGP5R (SEQ ID No. 36) and primer MBC1LVS1, and the obtained DNA fragment was digested with BamHI and HindIII, and subcloned into BamHI and the HindIII sites of pUC19. After the nucleotide sequence was determined, the fragment was digested with restriction enzymes HindIII and AflII and ligated to hMBC1Laλ/pUC19 which was digested with HindIII and AflII.

The obtained plasmid was designated as hMBC1Lbλ/pUC19, and this plasmid was digested with EcoRI, a fragment containing DNA encoding the humanized L chain was introduced into a plasmid pCOS1 so that the start codon of the humanized L chain might be located downstream the EF1α promoter. The obtained plasmid was designated as hMBC1Lbλ/pCOS 1.

Version "c" was prepared using the mutagenesis by the PCR method. The version "c" was designed so that serine at the 84th position (the 80th position of the amino acid number according to Kabat designation) might be changed to proline. PCR was performed with plasmid hMBC1Laλ/pUC19 as a template using mutagenic primer MBC1LGP6S (SEQ ID No. 37) and primer M13 Primer RV, and the obtained DNA fragment was digested with BamHI and HindIII, and subcloned into pUC19 which had been digested with BamHI and HindIII.

After the nucleotide sequence was determined, the fragment was digested with restriction enzymes BstPI and Aor51HI and ligated to hMBC1Laλ/pUC19 which was digested with BstPI and Aor51HI. The thus obtained plasmid was designated as hMBC1L Cλ/pUC19, and this plasmid was digested with restriction enzyme EcoRI, a fragment containing DNA encoding the humanized L chain was introduced into EcoRI site of plasmid pCOS1 so that the start codon of the humanized L chain might be located downstream the EF1α promoter. The thus obtained plasmid was designated as hMBC1Lcλ/pCOS1.

Versions "d", "e" and "f" were prepared using the mutagenesis by the PCR method. The versions "d", "e" and "f" were designed so that tyrosine at the 91st position (the 87th position of the amino acid number according to Kabat designation) in the versions "a", "b" and "c" in this order might be changed to isoleucine. PCR was performed with hMBC1Laλ/pCOS1, hMBC1Lbλ/pCOS1, and hMBC1Lcλ/pCOS1 as a template respectively using mutagenic primer MBC1LGP11R (SEQ ID No. 38) and primer M-S1 (SEQ ID No. 44), and the obtained DNA fragments were digested with BamHI and HindIII, and subcloned into pUC19 which had been digested with BamHI and HindIII. After the nucleotide sequence was determined, the fragments were digested with HindIII and BlnI and ligated to Cλ/pUC19 which was prepared by digestion with HindIII and BlnI.

The thus obtained plasmids were designated as hMBC1Ldλ/pUC19, hMBC1Leλ/pUC19 and hMBC1Lfλ/pUC19, respectively. These plasmids were digested with EcoRI, a fragment containing DNA encoding the humanized L chain was introduced into the EcoRI site of plasmid pCOS1 so that the start codon of the humanized L chain might be located downstream the EF1α promoter. The thus obtained plasmids were designated as in order hMBC1Ldλ/pCOS1, hMBC1Leλ/pCOS1 and hMBC1Lfλ/pCOS1, respectively.

Versions "g" and "h" were prepared using the mutagenesis by the PCR method. The versions "g" and "h" were designed so that histidine at the 36th position (the 36th position of the amino acid number according to Kabat designation) in the versions "a" and "d" in this order might be changed to tyrosine. PCR was performed with hMBC1Laλ/pUC19 as a template using mutagenic primer MBC1LGP9R (SEQ ID No. 39) and M13 Primer RV, and PCR was further performed with plasmid hMBC1Laλ/pUC19 as a template using the obtained PCR products and M13 Primer M4 as primers. The obtained DNA fragments were digested with HindIII and BlnI, and subcloned into a Cλ/pUC19 which was prepared by digestion with HindIII and BlnI. PCR was performed with this plasmid as a template using MBC1LGP13R (SEQ ID No. 40) and MBC1LVS1 as primers. The obtained PCR fragments were digested with ApaI and HindIII, and introduced into plasmid hMBC1Laλ/pUC19 and hMBC1Ldλ/pUC19 which was digested with ApaI and HindIII. The nucleotide sequence was determined, and plasmids containing the correct sequences were designated as hMBC1Lgλ/pUC19 and hMBC1Lhλ/pUC19 in order, these plasmids were digested with restriction enzyme EcoRI and the sequence containing a sequence encoding the humanized L chain was introduced into the EcoRI site of plasmid pCOS1 so that the start codon of the humanized L chain might be located downstream the EF1α promoter. The thus obtained plasmids were designated in order as hMBC1Lgλ/pCOS1 and hMBC1Lhλ/pCOS 1, respectively.

Versions "i", "j", "k", "l", "m", "n", and "o" were prepared using the mutagenesis by the PCR method. PCR was performed with plasmid hMBC1Lgλ/pUC19 as a template using mutagenic primer MBC1LGP14S (SEQ ID No. 41) and primer V1RV (λ) (SEQ ID No. 43), and the obtained DNA fragments were digested with ApaI and BlnI, and subcloned into plasmid hMBC1Lgλ/pUC19 prepared by digesting with ApaI and BlnI. After the nucleotide sequence was determined, and the clones into which the mutation corresponding to each version was introduced were selected. The obtained plasmids were designated as hMBC1Lx/pUC19 (x=i, j, k, l, m, n, o), and subjected to EcoRI digestion, and a sequence containing a sequence which encodes the humanized L chain was introduced into the EcoRI site of plasmid pCOS1 so that the start codon of the humanized L chain might be located downstream the EF1α promoter. The obtained plasmids were designated as hMBC1Lxλ/pCOS1 (x=i, j, k, l, m, n, o). The nucleotide sequence (including corresponding amino acid) of versions "j", "l", "m" and "o" are shown in the SEQ ID Nos. 67, 68, 69 and 70, respectively. In addition, the amino acid sequences of these versions are shown in the SEQ ID Nos. 48, 49, 50 and 51, respectively.

Version "p", "q", "r", "s" and "t" are the version in which tyrosine at the 87th position of the amino acid sequence of version "i", "j", "m", "l", or "o" is replaced by isoleucine, and the restriction enzyme Aor51MI cleaving site in FR3 is used to link version "h" to each version "i", "j", "m", "l", or "o". Namely, in the expression plasmids hMBC1Lxλ/pCOS1 (x=i, j, m, l, o), Aor51HI fragment of 514 bp containing CDR3, a part of FR3, and FR4 is removed and linked here to Aor51HI fragment of 514 bp containing CDR3, a part of FR3, and FR4 in the expression plasmid hMBC1Lhλ/pCOS1 so that tyrosine at the 91st position (the 87th position of the amino acid number according to Kabat designation) might be changed to isoleucine. The nucleotide sequence were determined and the clones of each version "i", "j", "m", "l" and "o" in which tyrosine at the 91st position (the 87th position of the amino acid number according to Kabat designation) is replaced by isoleucine were selected and the corresponding version was designated as "p", "q", "s", "r", and "t", respectively, and the obtained plasmids were designated as hMBC1Lxλ/pCOS1 (x=p, q, s, r, t). The nucleotide sequences (including the corresponding amino acids) of version "q", "r", "s" and "t" are shown in SEQ ID Nos. 71, 72, 73 and 74, respectively. In addition, the amino acid sequences of each of these versions are shown in SEQ ID Nos. 52, 53, 54, and 55, respectively.

The plasmid hMBC1Lqλ/pCOS1 was digested with HindIII and EcoRI and subcloned into the plasmid pUC19 which was digested with HindIII and EcoRI, and was designated as plasmid hMBC1Lqλ/pUC19.

The positions of the substituted amino acid in each version of the humanized L chain are shown in Table 2.

TABLE 2

| Positions of the substituted amino acids in the sequence listing | | | | | | |
|---|---|---|---|---|---|---|
| Version | 36 | 43 | 45 | 47 | 49 | 80 | 87 |
| a | | | | | | | |
| b | | P | | | D | | |
| c | | | | | | | P |

TABLE 2-continued

Positions of the substituted amino acids in the sequence listing

| Version | 36 | 43 | 45 | 47 | 49 | 80 | 87 |
|---|---|---|---|---|---|---|---|
| d |  |  |  |  |  |  | I |
| e |  | P |  |  | D |  | I |
| f |  |  |  |  |  | P | I |
| g | Y |  |  |  |  |  |  |
| h | Y |  |  |  |  |  | I |
| i | Y |  | K |  |  |  |  |
| j | Y |  | K |  | D |  |  |
| k | Y |  | K | V |  |  |  |
| l | Y |  | K | V | D |  |  |
| m | Y |  |  |  | D |  |  |
| n | Y |  |  | V |  |  |  |
| o | Y |  |  | V | D |  |  |
| p | Y |  | K |  |  |  | I |
| q | Y |  | K |  | D |  | I |
| r | Y |  |  |  | D |  | I |
| s | Y |  | K | V | D |  | I |
| t | Y |  |  | V | D |  | I |

In the table, Y represents tyrosine, P represents proline, K represents lysine, V represents varine, D represents aspartic acid and I represents isoleucine.

*E. coli* which having above-mentioned plasmid hMBC1HcDNA/pUC19 and hMBC1Lqλ/pUC19 were internationally deposited as *Escherichia coli* JM109 (hMBC1HcDNA/pUC19) and *Escherichia coli* JM109 (hMBC1Lqλ/pUC19) on Aug. 15, 1996 under the Budapest Treaty with International Patent Organism Depositary, National Institute of Advanced Industrial Science and Technology, an Independent Administrative Institution, located at Tsukuba Central 6, 1-1-1 Higashi, Tsukuba, Ibaraki, Japan under accession number FERM BP-5629 for *Escherichia coli* JM109 (hMBC1HcDNA/pUC19) and FERM BP-5630 for *Escherichia coli* JM109(hMBC1Lqλ/pUC19).

(5) Transfection to COS-7 Cell

In order to evaluate the antigen binding activity and neutralization activity of the hybrid antibody and humanized #23-57-137-1 antibody, the above-mentioned expression plasmid was made to express transiently in COS-7 cell. That is, in the transient expression of L chain hybrid antibody, combinations of plasmids hMBC1HcDNA/pCOS1 and h/mMBC1L(λ)/neo, hMBC1HcDNA/pCOS1 and m/hMBC1Laλ/neo, hMBC1HcDNA/pCOS1 and m/hMBC1Ldλ/neo, hMBC1 HcDNA/pCOS1 and hmmMBC1L(λ)/neo or hMBC1HcDNA/pCOS1 and mhmMBC1L(λ)/neo were simultaneous transduced into COS-7 cell by electroporation using Gene Pulser equipment (Bio Rad). Ten (10) μg of each plasmid DNA was added to 0.8 ml of COS-7 cells suspended by cell concentration of $1 \times 10^7$ cell/ml in PBS (−), and the pulse was given by the capacitance of 1,500V and 25 μF.

After maintained at room temperature for 10 minutes to restore, the cells which had been subjected to electroporation treatment was suspended to DMEM culture solution (GIBCO) containing 2% of Ultra Low IgG Fetal Bovine Serum (GIBCO), and were cultured in $CO_2$ incubator using a 10 cm culturing plate. Culture supernatant was collected after culturing of 72 hours, the cell fragments were centrifugally removed, and the samples were subjected to ELISA.

In transient expression of humanized #23-57-137-1 antibody, transfection of the combination of plasmid hMBC1HcDNA/pCOS1 and hMBC1Lxλ/pCOS1 (x=a to t) to COS-7 cell was carried out using Gene Pulser equipment (Bio Rad) in the same manner as in the case of the above-mentioned hybrid antibody, and the obtained culture supernatants were subjected to ELISA.

In addition, purification of the hybrid antibody or the humanized antibody from the culture supernatant of COS-7 cell was performed using the AffiGel Protein A MAPSII kit (BioRad) according to the instructions appended to the kit.

(6) ELISA (i) Measurement of Antibody Concentration

The ELISA plate used for antibody concentration measurement was prepared as follows. Each well of a 96 well plate for ELISA (Maxisorp, NUNC) is coated with 100 μl of goat anti-man IgG antibody (TAGO) adjusted to a concentration of 1 μg/ml with the coating buffer (0.1M NaHCO3, 0.02% NaN3), and blocked with 200 μl of a dilution buffer (50 mM Tris-HCl, 1 mM $MgCl_2$, 0.1 M NaCl, 0.05% Tween20, 0.02% NaN3 and 1% bovine serum albumin (BSA), pH 7.2). The culture supernatant of the COS-7 cells in which hybrid antibody or humanized antibody was expressed or the purified hybrid antibody or the humanized antibody was stepwise diluted and added to each well. After the plate was incubated at room temperature for 1 hour and washed with PBS-Tween20, 100 μl of alkaline phosphatase (TAGO) conjugated goat anti-man IgG antibody was added. After the plate was incubated at room temperature for 1 hour and washed with PBS-Tween20, 1 mg/ml of a substrate solution (Sigma104, p-nitrophenylphosphate, SIGMA) was added, and 405 nm absorption was then measured on a micro plate reader (Bio Rad). As the standard for concentration measurement, Hu IgG1λ Purified (The Binding Site) was used.

(ii) Measurement of Antigen Binding Ability

The ELISA plate for antigen binding measurement was prepared as follows. Each well of a 96 well plate for ELISA was coated with 100 μl of human PTHrP(1-34) adjusted to 1 μg/ml concentration by the coating buffer. After blocking with 200 μl of the dilution buffer, the culture supernatant of the COS-7 cells in which hybrid antibody or humanized antibody was expressed or the purified hybrid antibody or the humanized antibody was stepwise diluted and added to each well. After the plate was incubated at room temperature and washed with PBS-Tween20, 100 μl of alkaline phosphatase (TAGO) conjugated goat anti-man IgG antibody was added. After the plate was incubated at room temperature and washed with PBS-Tween20, 1 mg/ml of a substrate solution (Sigma104, p-nitrophenylphosphate, SIGMA) was added, and 405 nm absorption was then measured on a micro plate reader (Bio Rad).

(7) Confirmation of Activity (i) Evaluation of Humanized H Chain

The antibody in which humanized H chain version "a" was combined with a chimera L chain had a PTHrP binding ability equivalent to that of the chimeric antibody. This result shows that version "a" is sufficient for forming a humanized of V domain of the H chain. Hereinafter, humanized H chain version "a" was provided as H chain of the humanized antibody.

(ii) Activity of Hybrid Antibody (ii-a) FR 1, 2/FR3, 4 Hybrid Antibody

Although the activity was not recognized at all when L chain was h/mMBC1L (λ), in the case of m/hMBC1Laλ or m/hMBC1Ldλ, the binding activity equivalent to chimera #23-57-137-1 antibody was exhibited. These results suggest that although FR 3, 4 are satisfactory as a humanized antibody, there is amino acid residue(s) which should be replaced in FR1, 2.

(ii-b) FR1/FR2 Hybrid Antibody

Although activity was not accepted at all when L chain was mhmMBC1L (λ), in the case of hmmMBC1L(λ), binding activity equivalent to chimera #23-57-137-1 antibody was exhibited. These results suggest that among FR1 and 2, FR1 is satisfactory as a humanized antibody but there is amino acid residue(s) which should be replaced in FR2.

(iii) Activity of Humanized Antibody

Antigen binding activity was measured for humanized antibodies in which either one of version "a" to "t" was used as an L chain respectively. Consequently, the humanized antibody which has L chain version "j", "l", "m", "o", "q", "r", "s" and "t" exhibited PTHrP binding ability equivalent to a chimeric antibody.

(8) Establishment of Stably Producing CHO Cell Line

In order to establish a cell line stably producing a humanized antibody, the above-mentioned expression plasmid was introduced into the CHO cell (DXB11).

That is, establishment of stably producing a humanized antibody is effected by simultaneous transducing the combination of expression plasmid for CHO cells expression plasmid hMBC1 HcDNA/pCHO1 and hMBC1Lmλ/pCOS1 or hMBC1 HcDNA/pCHO1 and hMBC1Lqλ/pCOS1, or hMBC1HcDNA/pCHO1 and hMBC1Lrλ/pCOS1 into CHO cells by electroporation using Gene Pulser equipment (Bio Rad). Each expression vector was cleaved with a restriction enzyme PvuI to form a linear DNA, and after phenol and chloroform extraction, the DNA was collected by ethanol precipitation and used for electroporation. Ten (10) µg each of plasmid DNA was added to 0.8 ml of CHO cells suspended at a cell concentration of $1 \times 10^7$ cell/ml in PBS (-), and the cells were pulsed at a capacitance of 1,500V and 25 µF. After allowed to recover at room temperature for 10 minutes, the electroporated cells were suspended in a MEM-α culture medium (GIBCO) supplemented with 10% of Fetal Bovine Serum (GIBCO) and cultured in a $CO_2$ incubator using a 96 well plates (Falcon). The culture medium was replaced by a selection culture medium which is MEM-α culture medium supplemented with 10% Fetal Bovine Serum (GIBCO) and 500 mg/ml GENETICIN (G418Sulfate, GIBCO) and free from ribonucleosides and deoxyribonucleosides on the next day after starting the culturing, and the cells into which the antibody gene was introduced were selected. In about two weeks after the selection culture medium was replaced, the cells were observed under the microscope and after favorable cell proliferation was recognized, the amount of antibody production was measured by the above-mentioned antibody concentration measurement ELISA, and the cells with much antibody production were selected.

Culturing of the established cell line which was capable of stably establishing an antibody was expanded, and the roller bottle performed extensive culturing using MEM-α culture medium supplemented with 2% of the Ultra Low IgG Fetal Bovine Serum, and free from ribonucleoside and deoxyribonucleoside. Culture supernatant were collected on day 3 or 4 of the culturing, and cell debris was removed with a 0.2-micrometer filter (Millipore). Purification of the humanized antibody from culture supernatant of a CHO cell was performed according to the appended instructions using POROS protein A column (PerSeptive Biosystems) by ConSep LC100 (Millipore), and measurement of neutralization activity and the efficacy for a hypercalcemia model animal were presented. The concentration and antigen binding activity of a purification humanized antibody which were obtained were measured by the above-mentioned ELISA system.

REFERENTIAL EXAMPLE 5

Measurement of Neutralization Activity

Measurement of the neutralization activity of a mouse antibody, a chimeric antibody, and a humanized antibody was performed using rat osteosarcoma cell line ROS17/2.8-5 cells. That is, ROS17/2.8-5 cells were cultured in Ham'S F-12 culture medium (GIBCO) which contains Fetal Bovine Serum (GIBCO) 10% in a $CO_2$ incubator. ROS17/2.8-5 cells were seeded on 96 well plate in $10^4$ cells/100 µl/well and cultured for one day, and the medium was exchanged to Ham'S F-12 culture medium (GIBCO) which contains 4 mM Hydrocortisone and 10% Fetal Bovine Serum. After culturing for further 3 to 4 days, it was washes with 260 µl of Ham'S F-12 culture medium (GIBCO) and 80 µl of Ham's F-12 containing 1 mM of isobutyl-1-methyl xanthine (IBMX, SIGMA) and 10% of Fetal Bovine Serum and 10 mM of HEPES was added, and incubation was carried out at 37° C. for 30 minutes.

The mouse antibody, chimeric antibody, or humanized antibody for which neutralization activity was to be measured were diluted stepwise beforehand to a group of 10 µg/ml, 3.3 µg/ml, 1.1 µg/ml and 0.37 µg/ml, a group of 10 µg/ml, 2 µg/ml, 0.5 µg/ml and 0.01 µg/ml, a group of 10 µg/ml, 5 µg/ml, 1.25 µg/ml, 0.63 µg/ml and 0.31 µg/ml and mixed with PTHrP (1-34) in equivalent amount, which was adjusted to 4 ng/ml, and 80 µl each of the mixture solution of each antibody and PTHrP (1-34) was added to each well. The final concentration of each antibody decreased to ¼ of the above-mentioned antibody concentration, and the concentration of PTHrP (1-34) was 1 ng/ml. After treating at room temperature for 10 minutes, culture supernatant is discarded, and after washing 3 times with PBS, cAMP in a cell was extracted in 100 µl of 95% ethanol containing 0.3% hydrochloric acid. The hydrochloric acid ethanol was evaporated in stream aspirator, 120 µl of EIA buffer appended to cAMP EIA kit (CAYMAN CHEMICAL'S) was added, and cAMP was measured after extracting cAMP according to the instructions appended to cAMP EIA kit (CAYMAN CHEMICAL'S). Consequently, among the L chain versions having antigen binding activity equivalent to a chimeric antibody, versions "q", "r", "s" and "t" in which tyrosine at the 91st position was replaced by isoleucine exhibited neutralization ability comparable to that of a chimeric antibody and among them, version "q" exhibited the highest neutralization ability.

It should be noted that all the publications, patents and patent applications cited in this specification are incorporated herein by reference.

INDUSTRIAL APPLICABILITY

According to the present invention, an agent for treating chondroma and chondrosarcoma which contains a substance which inhibits binding of parathyroid hormone related peptide and a receptor thereof as an active ingredient is provided. The agent of the present invention controls chondroma and chondrosarcoma by inducing apoptosis of chondroma and chondrosarcoma cells.

Free Text to Sequence Listing

SEQ ID No. 1—description of artificial sequence: synthetic DNA

SEQ ID No. 2—description of artificial sequence: synthetic DNA

SEQ ID No. 3—description of artificial sequence: synthetic DNA
SEQ ID No. 4—description of artificial sequence: synthetic DNA
SEQ ID No. 5—description of artificial sequence: synthetic DNA
SEQ ID No. 6—description of artificial sequence: synthetic DNA
SEQ ID No. 7—description of artificial sequence: synthetic DNA
SEQ ID No. 8—description of artificial sequence: synthetic DNA
SEQ ID No. 9—description of artificial sequence: synthetic DNA
SEQ ID No. 10—description of artificial sequence: synthetic DNA
SEQ ID No. 11—description of artificial sequence: synthetic DNA
SEQ ID No. 12—description of artificial sequence: synthetic DNA
SEQ ID No. 13—description of artificial sequence: synthetic DNA
SEQ ID No. 14—description of artificial sequence: synthetic DNA
SEQ ID No. 15—description of artificial sequence: synthetic DNA
SEQ ID No. 16—description of artificial sequence: synthetic DNA
SEQ ID No. 17—description of artificial sequence: synthetic DNA
SEQ ID No. 18—description of artificial sequence: synthetic DNA
SEQ ID No. 19—description of artificial sequence: synthetic DNA
SEQ ID No. 20—description of artificial sequence: synthetic DNA
SEQ ID No. 21—description of artificial sequence: synthetic DNA
SEQ ID No. 22—description of artificial sequence: synthetic DNA
SEQ ID No. 23—description of artificial sequence: synthetic DNA
SEQ ID No. 24—description of artificial sequence: synthetic DNA
SEQ ID No. 25—description of artificial sequence: synthetic DNA
SEQ ID No. 26—description of artificial sequence: synthetic DNA
SEQ ID No. 27—description of artificial sequence: synthetic DNA
SEQ ID No. 28—description of artificial sequence: synthetic DNA
SEQ ID No. 29—description of artificial sequence: synthetic DNA
SEQ ID No. 30—description of artificial sequence: synthetic DNA
SEQ ID No. 31—description of artificial sequence: synthetic DNA
SEQ ID No. 32—description of artificial sequence: synthetic DNA
SEQ ID No. 33—description of artificial sequence: synthetic DNA
SEQ ID No. 34—description of artificial sequence: synthetic DNA
SEQ ID No. 35—description of artificial sequence: synthetic DNA
SEQ ID No. 36—description of artificial sequence: synthetic DNA
SEQ ID No. 37—description of artificial sequence: synthetic DNA
SEQ ID No. 38—description of artificial sequence: synthetic DNA
SEQ ID No. 39—description of artificial sequence: synthetic DNA
SEQ ID No. 40—description of artificial sequence: synthetic DNA
SEQ ID No. 41—description of artificial sequence: synthetic DNA
SEQ ID No. 42—description of artificial sequence: synthetic DNA
SEQ ID No. 43—description of artificial sequence: synthetic DNA
SEQ ID No. 44—description of artificial sequence: synthetic DNA
SEQ ID No. 76—description of artificial sequence: synthetic DNA
SEQ ID No. 77—description of artificial sequence: synthetic DNA
SEQ ID No. 78—description of artificial sequence: synthetic DNA
SEQ ID No. 79—description of artificial sequence: synthetic DNA
SEQ ID No. 80—description of artificial sequence: synthetic DNA
SEQ ID No. 81—description of artificial sequence: synthetic DNA
SEQ ID No. 82—description of artificial sequence: synthetic DNA
SEQ ID No. 83—description of artificial sequence: synthetic DNA
SEQ ID No. 84—description of artificial sequence: synthetic DNA
SEQ ID No. 85—description of artificial sequence: synthetic DNA

The invention claimed is:

1. A method for treating chondroma and chondrosarcoma, which comprises administering, to a subject in need thereof, a substance which inhibits binding of parathyroid hormone related peptide to a receptor thereof, wherein the substance is humanized anti-PTHrP(1-34) antibody wherein the L chain V domain comprises a polypeptide with any one of the amino acid sequences of SEQ ID NOs: 48-55 and the H chain V domain comprises a polypeptide with the amino acid sequence of SEQ ID NO: 56.

2. A method of inducing apoptosis in chondroma and chondrosarcoma cells by administering a substance which inhibits binding of parathyroid hormone related peptide and a receptor thereof, wherein the substance is humanized anti-PTHrP (1-34) antibody wherein the L chain V domain comprises a polypeptide with any one of the amino acid sequences of SEQ ID NOs: 48-55 and the H chain V domain comprises a polypeptide with the amino acid sequence of SEQ ID NO: 56.

3. The method according to claim 2, wherein the apoptosis is induced through the control of Bcl-2/Bax by the humanized anti-PTHrP(1-34) antibody wherein the L chain V domain comprises a polypeptide with any one of the amino acid sequences of SEQ ID NOs: 48-55 and the H chain V domain comprises a polypeptide with the amino acid sequence of SEQ ID NO: 56.

4. The method according to claim 2, wherein the apoptosis is induced through the control of caspase 3 by humanized the anti-PTHrP(1-34) antibody wherein the L chain V domain comprises a polypeptide with any one of the amino acid sequences of SEQ ID NOs: 48-55 and the H chain V domain comprises a polypeptide with the amino acid sequence of SEQ ID NO: 56.

5. The method according to claim 2, wherein the apoptosis is induced in vivo.

6. The method according to claim 2, wherein the apoptosis is induced in vitro.

* * * * *

SEQUENCE LISTING

<160> NUMBER OF SEQ ID NOS: 85

<210> SEQ ID NO 1
<211> LENGTH: 20
<212> TYPE: DNA
<213> ORGANISM: Artificial Sequence
<220> FEATURE:
<223> OTHER INFORMATION: Inventor; Yoshikawa, Hideki; Miyaji, Takahiro
<220> FEATURE:
<223> OTHER INFORMATION: Description of Artificial Sequence:Synthetic

DNA

<400> SEQUENCE: 1
aaatagccct tgaccaggca                                           20

<210> SEQ ID NO 2
<211> LENGTH: 38
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 2
ctggttcggc ccacctctga aggttccaga atcgatag                       38

<210> SEQ ID NO 3
<211> LENGTH: 28
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 3
ggatcccggg ccagtggata gacagatg                                  28

<210> SEQ ID NO 4
<211> LENGTH: 29
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 4
ggatcccggg tcagrggaag gtggraaca                                 29

<210> SEQ ID NO 5
<211> LENGTH: 17
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 5
gttttcccag tcacgac                                              17

<210> SEQ ID NO 6
<211> LENGTH: 17
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 6
caggaaacag ctatgac                                              17

<210> SEQ ID NO 7
<211> LENGTH: 31
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 7
gtctaagctt ccaccatgaa acttcgggct c                                    31

<210> SEQ ID NO 8
<211> LENGTH: 30
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 8
tgttggatcc ctgcagagac agtgaccaga                                      30

<210> SEQ ID NO 9
<211> LENGTH: 36
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 9
gtctgaattc aagcttccac catggggttt gggctg                               36

<210> SEQ ID NO 10
<211> LENGTH: 41
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 10
tttcccgggc ccttggtgga ggctgaggag acggtgacca g                         41

<210> SEQ ID NO 11
<211> LENGTH: 109
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 11
gtctgaattc aagcttagta cttggccagc ccaaggccaa ccccacggtc accctgttcc     60
cgccctcctc tgaggagctc aagccaaca aggccacact agtgtgtct                  109

<210> SEQ ID NO 12
<211> LENGTH: 110
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 12
ggtttggtgg tctccactcc cgccttgacg gggctgccat ctgccttcca ggccactgtc     60
acagctcccg ggtagaagtc actgatcaga cacactagtg tggccttgtt                110

<210> SEQ ID NO 13
<211> LENGTH: 98
<212> TYPE: DNA
<213> ORGANISM: Artificial Sequence
<220> FEATURE:
<223> OTHER INFORMATION: Description of Artificial Sequence:Synthetic DNA

<400> SEQUENCE: 13
ggagtggaga ccaccaaacc ctccaaacag agcaacaaca agtacgcggc cagcagctac    60
ctgagcctga cgcccgagca gtggaagtcc cacagaag                            98

<210> SEQ ID NO 14
<211> LENGTH: 106
<212> TYPE: DNA
<213> ORGANISM: Artificial Sequence
<220> FEATURE:
<223> OTHER INFORMATION: Description of Artificial Sequence:Synthetic DNA

<400> SEQUENCE: 14
tgttgaattc ttactatgaa cattctgtag gggccactgt cttctccacg gtgctccctt    60
catgcgtgac ctggcagctg tagcttctgt gggacttcca ctgctc                   106

<210> SEQ ID NO 15
<211> LENGTH: 43
<212> TYPE: DNA
<213> ORGANISM: Artificial Sequence
<220> FEATURE:
<223> OTHER INFORMATION: Description of Artificial Sequence:Synthetic DNA

<400> SEQUENCE: 15
gtctgaattc aagcttagta cttggccagc ccaaggccaa ccc                      43

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence:Synthetic DNA

<400> SEQUENCE: 16
tgttgaattc ttactatgaa                                                20

<210> SEQ ID NO 17
<211> LENGTH: 39
<212> TYPE: DNA
<213> ORGANISM: Artificial Sequence
<220> FEATURE:
<223> OTHER INFORMATION: Description of Artificial Sequence:Synthetic DNA

<400> SEQUENCE: 17
caacaagtac gcggccagca gctacctgag cctgacgcc                           39

<210> SEQ ID NO 18
<211> LENGTH: 39
<212> TYPE: DNA
<213> ORGANISM: Artificial Sequence
<220> FEATURE:
<223> OTHER INFORMATION: Description of Artificial Sequence:Synthetic DNA

<400> SEQUENCE: 18
gtagctgctg gccgcgtact tgttgttgct ctgtttgga                           39

<210> SEQ ID NO 19

```
<211> LENGTH: 46
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 19
gtctgaattc aagcttagtc ctaggtcgaa ctgtggctgc accatc              46

<210> SEQ ID NO 20
<211> LENGTH: 34
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 20
tgttgaattc ttactaacac tctccctgt tgaa                            34

<210> SEQ ID NO 21
<211> LENGTH: 35
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 21
gtctaagctt ccaccatggc ctggactcct ctctt                          35

<210> SEQ ID NO 22
<211> LENGTH: 48
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 22
tgttgaattc agatctaact acttacctag gacagtgacc ttggtccc            48

<210> SEQ ID NO 23
<211> LENGTH: 128
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 23
gtctaagctt ccaccatggg gtttgggctg agctgggttt cctcgttgc tcttttaaga    60 ggtgtccagt gtcaggtgca gctggtggag tctgggggag gcgtggtcca gcctgggagg  120
tccctgag                                                          128

<210> SEQ ID NO 24
<211> LENGTH: 125
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 24
accattagta gtggtggtag ttacacctac tatccagaca gtgtgaaggg gcgattcacc   60
```

```
atctccagag acaattccaa gaacacgctg tatctgcaaa tgaacagcct gagagctgag      120
gacac                                                                  125

<210> SEQ ID NO 25
<211> LENGTH: 132
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 25
ctaccaccac tactaatggt tgccacccac tccagcccct tgcctggagc ctggcggacc      60
caagacatgc catagctact gaaggtgaat ccagaggctg cacaggagag tctcagggac     120
ctcccaggct gg                                                         132

<210> SEQ ID NO 26
<211> LENGTH: 110
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 26
tgttggatcc ctgaggagac ggtgaccagg gttccctggc cccagtaagc aaagtaagtc      60
atagtagtct gtctcgcaca gtaatacaca gccgtgtcct cagctctcag                110

<210> SEQ ID NO 27
<211> LENGTH: 30
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 27
gtctaagctt ccaccatggg gtttgggctg                                       30

<210> SEQ ID NO 28
<211> LENGTH: 30
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 28
tgttggatcc ctgaggagac ggtgaccagg                                       30

<210> SEQ ID NO 29
<211> LENGTH: 133
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 29
acaaagcttc caccatggcc tggactcctc tcttcttctt ctttgttctt cattgctcag      60 gttcttctc ccagcttgtg ctgactcaat cgccctctgc ctctgcctcc ctgggagcct     120
cggtcaagct cac                                                        133
```

-continued

<210> SEQ ID NO 30
<211> LENGTH: 118
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 30
agcaagatgg aagccacagc acaggtgatg ggattcctga tcgcttctca ggctccagct    60
ctggggctga gcgctacctc accatctcca gcctccagtc tgaggatgag gctgacta     118

<210> SEQ ID NO 31
<211> LENGTH: 128
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 31
ctgtggcttc catcttgctt aagtttcatc aagtaccgag ggcccttctc tggctgctgc    60
tgatgccatt caatggtgta cgtactgtgc tgactactca aggtgcaggt gagcttgacc   120
gaggctcc                                                            128

<210> SEQ ID NO 32
<211> LENGTH: 114
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 32
cttggatccg ggctgaccta ggacggtcag tttggtccct ccgccgaaca ccctcacaaa    60
ttgttcctta attgtatcac ccacaccaca gtaatagtca gcctcatcct caga          114

<210> SEQ ID NO 33
<211> LENGTH: 17
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 33
acaaagcttc caccatg                                                   17

<210> SEQ ID NO 34
<211> LENGTH: 19
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 34
cttggatccg ggctgacct                                                 19

<210> SEQ ID NO 35
<211> LENGTH: 75
<212> TYPE: DNA
<213> ORGANISM: Artificial Sequence

```
<220> FEATURE:
<223> OTHER INFORMATION: Description of Artificial Sequence:Synthetic
      DNA

<400> SEQUENCE: 35
cttggatccg ggctgaccta ggacggtcag tttggtccct ccgccgaaca cgtacacaaa      60
ttgttcctta attgt                                                      75

<210> SEQ ID NO 36
<211> LENGTH: 43
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 36
aaaggatcct taagatccat caagtaccga gggggcttct ctg                       43

<210> SEQ ID NO 37
<211> LENGTH: 46
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 37
acaaagctta gcgctacctc accatctcca gcctccagcc tgagga                    46

<210> SEQ ID NO 38
<211> LENGTH: 111
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 38
cttggatccg ggctgaccta ggacggtcag tttggtccct ccgccgaaca cgtacacaaa      60
ttgttcctta attgtatcac ccacaccaca gatatagtca gcctcatcct c              111

<210> SEQ ID NO 39
<211> LENGTH: 42
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 39
cttctctggc tgctgctgat accattcaat ggtgtacgta ct                        42

<210> SEQ ID NO 40
<211> LENGTH: 26
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 40
cgagggccct tctctggctg ctgctg                                          26

<210> SEQ ID NO 41
```

<211> LENGTH: 35
<212> TYPE: DNA
<213> ORGANISM: Artificial Sequence
<220> FEATURE:
<223> OTHER INFORMATION: Description of Artificial Sequence:Synthetic DNA

<400> SEQUENCE: 41
gagaagggcc ctargtacst gatgrawctt aagca    35

<210> SEQ ID NO 42
<211> LENGTH: 35
<212> TYPE: DNA
<213> ORGANISM: Artificial Sequence
<220> FEATURE:
<223> OTHER INFORMATION: Description of Artificial Sequence:Synthetic DNA

<400> SEQUENCE: 42
cacgaattca ctatcgattc tggaaccttc agagg    35

<210> SEQ ID NO 43
<211> LENGTH: 18
<212> TYPE: DNA
<213> ORGANISM: Artificial Sequence
<220> FEATURE:
<223> OTHER INFORMATION: Description of Artificial Sequence:Synthetic DNA

<400> SEQUENCE: 43
ggcttggagc tcctcaga    18

<210> SEQ ID NO 44
<211> LENGTH: 20
<212> TYPE: DNA
<213> ORGANISM: Artificial Sequence
<220> FEATURE:
<223> OTHER INFORMATION: Description of Artificial Sequence:Synthetic DNA

<400> SEQUENCE: 44
gacagtggtt caaagttttt    20

<210> SEQ ID NO 45
<211> LENGTH: 118
<212> TYPE: PRT
<213> ORGANISM: Mus musculus

<400> SEQUENCE: 45

Gln Leu Val Leu Thr Gln Ser Ser Ala Ser Phe Ser Leu Gly Ala
 1               5                  10                  15

Ser Ala Lys Leu Thr Cys Thr Leu Ser Ser Gln His Ser Thr Tyr Thr
                20                  25                  30

Ile Glu Trp Tyr Gln Gln Pro Leu Lys Pro Pro Lys Tyr Val Met
            35                  40                  45

Asp Leu Lys Gln Asp Gly Ser His Ser Thr Gly Asp Gly Ile Pro Asp
        50                  55                  60

Arg Phe Ser Gly Ser Ser Ser Gly Ala Asp Arg Tyr Leu Ser Ile Ser
 65                  70                  75                  80

Asn Ile Gln Pro Glu Asp Glu Ala Met Tyr Ile Cys Gly Val Gly Asp
                85                  90                  95

Thr Ile Lys Glu Gln Phe Val Tyr Val Phe Gly Gly Gly Thr Lys Val
            100                 105                 110

```
Thr Val Leu Gly Gln Pro
        115

<210> SEQ ID NO 46
<211> LENGTH: 118
<212> TYPE: PRT
<213> ORGANISM: Mus musculus

<400> SEQUENCE: 46

Glu Val Gln Leu Val Glu Ser Gly Gly Asp Leu Val Lys Pro Gly Gly
  1               5                  10                  15

Ser Leu Lys Leu Ser Cys Ala Ala Ser Gly Phe Thr Phe Ser Ser Tyr
             20                  25                  30

Gly Met Ser Trp Ile Arg Gln Thr Pro Asp Lys Arg Leu Glu Trp Val
         35                  40                  45

Ala Thr Ile Ser Ser Gly Gly Ser Tyr Thr Tyr Tyr Pro Asp Ser Val
     50                  55                  60

Lys Gly Arg Phe Thr Ile Ser Arg Asp Asn Ala Lys Asn Thr Leu Tyr
 65                  70                  75                  80

Leu Gln Met Ser Ser Leu Lys Ser Glu Asp Thr Ala Met Phe Tyr Cys
                 85                  90                  95

Ala Arg Gln Thr Thr Met Thr Tyr Phe Ala Tyr Trp Gly Gln Gly Thr
            100                 105                 110

Leu Val Thr Val Ser Ala
        115

<210> SEQ ID NO 47
<211> LENGTH: 116
<212> TYPE: PRT
<213> ORGANISM: Homo sapiens

<400> SEQUENCE: 47

Gln Leu Val Leu Thr Gln Ser Pro Ser Ala Ser Ala Ser Leu Gly Ala
  1               5                  10                  15

Ser Val Lys Leu Thr Cys Thr Leu Ser Ser Gln His Ser Thr Tyr Thr
             20                  25                  30

Ile Glu Trp His Gln Gln Pro Glu Lys Gly Pro Arg Tyr Leu Met
         35                  40                  45

Lys Leu Lys Gln Asp Gly Ser His Ser Thr Gly Asp Gly Ile Pro Asp
     50                  55                  60

Arg Phe Ser Gly Ser Ser Ser Gly Ala Glu Arg Tyr Leu Thr Ile Ser
 65                  70                  75                  80

Ser Leu Gln Ser Glu Asp Glu Ala Asp Tyr Tyr Cys Gly Val Gly Asp
                 85                  90                  95

Thr Ile Lys Glu Gln Phe Val Tyr Val Phe Gly Gly Gly Thr Lys Leu
            100                 105                 110

Thr Val Leu Gly
        115

<210> SEQ ID NO 48
<211> LENGTH: 118
<212> TYPE: PRT
<213> ORGANISM: Homo sapiens

<400> SEQUENCE: 48

Gln Leu Val Leu Thr Gln Ser Pro Ser Ala Ser Ala Ser Leu Gly Ala
  1               5                  10                  15

Ser Val Lys Leu Thr Cys Thr Leu Ser Ser Gln His Ser Thr Tyr Thr
             20                  25                  30
```

-continued

```
                    20                  25                  30
Ile Glu Trp Tyr Gln Gln Pro Glu Lys Gly Pro Lys Tyr Leu Met
            35                  40                  45

Asp Leu Lys Gln Asp Gly Ser His Ser Thr Gly Asp Gly Ile Pro Asp
        50                  55                  60

Arg Phe Ser Gly Ser Ser Gly Ala Glu Arg Tyr Leu Thr Ile Ser
 65                  70                  75                  80

Ser Leu Gln Ser Glu Asp Glu Ala Asp Tyr Tyr Cys Gly Val Gly Asp
                85                  90                  95

Thr Ile Lys Glu Gln Phe Val Tyr Val Phe Gly Gly Gly Thr Lys Leu
            100                 105                 110

Thr Val Leu Gly Gln Pro
        115

<210> SEQ ID NO 49
<211> LENGTH: 118
<212> TYPE: PRT
<213> ORGANISM: Homo sapiens

<400> SEQUENCE: 49

Gln Leu Val Leu Thr Gln Ser Pro Ser Ala Ser Ala Ser Leu Gly Ala
 1               5                  10                  15

Ser Val Lys Leu Thr Cys Thr Leu Ser Ser Gln His Ser Thr Tyr Thr
            20                  25                  30

Ile Glu Trp Tyr Gln Gln Pro Glu Lys Gly Pro Lys Tyr Val Met
            35                  40                  45

Asp Leu Lys Gln Asp Gly Ser His Ser Thr Gly Asp Gly Ile Pro Asp
        50                  55                  60

Arg Phe Ser Gly Ser Ser Gly Ala Glu Arg Tyr Leu Thr Ile Ser
 65                  70                  75                  80

Ser Leu Gln Ser Glu Asp Glu Ala Asp Tyr Tyr Cys Gly Val Gly Asp
                85                  90                  95

Thr Ile Lys Glu Gln Phe Val Tyr Val Phe Gly Gly Gly Thr Lys Leu
            100                 105                 110

Thr Val Leu Gly Gln Pro
        115

<210> SEQ ID NO 50
<211> LENGTH: 118
<212> TYPE: PRT
<213> ORGANISM: Homo sapiens

<400> SEQUENCE: 50

Gln Leu Val Leu Thr Gln Ser Pro Ser Ala Ser Ala Ser Leu Gly Ala
 1               5                  10                  15

Ser Val Lys Leu Thr Cys Thr Leu Ser Ser Gln His Ser Thr Tyr Thr
            20                  25                  30

Ile Glu Trp Tyr Gln Gln Pro Glu Lys Gly Pro Arg Tyr Leu Met
            35                  40                  45

Asp Leu Lys Gln Asp Gly Ser His Ser Thr Gly Asp Gly Ile Pro Asp
        50                  55                  60

Arg Phe Ser Gly Ser Ser Gly Ala Glu Arg Tyr Leu Thr Ile Ser
 65                  70                  75                  80

Ser Leu Gln Ser Glu Asp Glu Ala Asp Tyr Tyr Cys Gly Val Gly Asp
                85                  90                  95

Thr Ile Lys Glu Gln Phe Val Tyr Val Phe Gly Gly Gly Thr Lys Leu
```

```
                100             105              110
Thr Val Leu Gly Gln Pro
        115

<210> SEQ ID NO 51
<211> LENGTH: 118
<212> TYPE: PRT
<213> ORGANISM: Homo sapiens

<400> SEQUENCE: 51

Gln Leu Val Leu Thr Gln Ser Pro Ser Ala Ser Ala Ser Leu Gly Ala
  1               5                  10                  15

Ser Val Lys Leu Thr Cys Thr Leu Ser Ser Gln His Ser Thr Tyr Thr
                 20                  25                  30

Ile Glu Trp Tyr Gln Gln Pro Glu Lys Gly Pro Arg Tyr Val Met
             35                  40                  45

Asp Leu Lys Gln Asp Gly Ser His Ser Thr Gly Asp Gly Ile Pro Asp
         50                  55                  60

Arg Phe Ser Gly Ser Ser Ser Gly Ala Glu Arg Tyr Leu Thr Ile Ser
 65                  70                  75                  80

Ser Leu Gln Ser Glu Asp Glu Ala Asp Tyr Tyr Cys Gly Val Gly Asp
                 85                  90                  95

Thr Ile Lys Glu Gln Phe Val Tyr Val Phe Gly Gly Gly Thr Lys Leu
                100                 105                 110

Thr Val Leu Gly Gln Pro
        115

<210> SEQ ID NO 52
<211> LENGTH: 118
<212> TYPE: PRT
<213> ORGANISM: Homo sapiens

<400> SEQUENCE: 52

Gln Leu Val Leu Thr Gln Ser Pro Ser Ala Ser Ala Ser Leu Gly Ala
  1               5                  10                  15

Ser Val Lys Leu Thr Cys Thr Leu Ser Ser Gln His Ser Thr Tyr Thr
                 20                  25                  30

Ile Glu Trp Tyr Gln Gln Pro Glu Lys Gly Pro Lys Tyr Leu Met
             35                  40                  45

Asp Leu Lys Gln Asp Gly Ser His Ser Thr Gly Asp Gly Ile Pro Asp
         50                  55                  60

Arg Phe Ser Gly Ser Ser Ser Gly Ala Glu Arg Tyr Leu Thr Ile Ser
 65                  70                  75                  80

Ser Leu Gln Ser Glu Asp Glu Ala Asp Tyr Ile Cys Gly Val Gly Asp
                 85                  90                  95

Thr Ile Lys Glu Gln Phe Val Tyr Val Phe Gly Gly Gly Thr Lys Leu
                100                 105                 110

Thr Val Leu Gly Gln Pro
        115

<210> SEQ ID NO 53
<211> LENGTH: 118
<212> TYPE: PRT
<213> ORGANISM: Homo sapiens

<400> SEQUENCE: 53

Gln Leu Val Leu Thr Gln Ser Pro Ser Ala Ser Ala Ser Leu Gly Ala
  1               5                  10                  15
```

Ser Val Lys Leu Thr Cys Thr Leu Ser Ser Gln His Ser Thr Tyr Thr
                20                  25                  30

Ile Glu Trp Tyr Gln Gln Pro Glu Lys Gly Pro Arg Tyr Leu Met
            35                  40                  45

Asp Leu Lys Gln Asp Gly Ser His Ser Thr Gly Asp Gly Ile Pro Asp
        50                  55                  60

Arg Phe Ser Gly Ser Ser Ser Gly Ala Glu Arg Tyr Leu Thr Ile Ser
65                  70                  75                  80

Ser Leu Gln Ser Glu Asp Glu Ala Asp Tyr Ile Cys Gly Val Gly Asp
                85                  90                  95

Thr Ile Lys Glu Gln Phe Val Tyr Val Phe Gly Gly Gly Thr Lys Leu
            100                 105                 110

Thr Val Leu Gly Gln Pro
        115

<210> SEQ ID NO 54
<211> LENGTH: 118
<212> TYPE: PRT
<213> ORGANISM: Homo sapiens

<400> SEQUENCE: 54

Gln Leu Val Leu Thr Gln Ser Pro Ser Ala Ser Ala Ser Leu Gly Ala
1               5                   10                  15

Ser Val Lys Leu Thr Cys Thr Leu Ser Ser Gln His Ser Thr Tyr Thr
                20                  25                  30

Ile Glu Trp Tyr Gln Gln Pro Glu Lys Gly Pro Lys Tyr Val Met
            35                  40                  45

Asp Leu Lys Gln Asp Gly Ser His Ser Thr Gly Asp Gly Ile Pro Asp
        50                  55                  60

Arg Phe Ser Gly Ser Ser Ser Gly Ala Glu Arg Tyr Leu Thr Ile Ser
65                  70                  75                  80

Ser Leu Gln Ser Glu Asp Glu Ala Asp Tyr Ile Cys Gly Val Gly Asp
                85                  90                  95

Thr Ile Lys Glu Gln Phe Val Tyr Val Phe Gly Gly Gly Thr Lys Leu
            100                 105                 110

Thr Val Leu Gly Gln Pro
        115

<210> SEQ ID NO 55
<211> LENGTH: 118
<212> TYPE: PRT
<213> ORGANISM: Homo sapiens

<400> SEQUENCE: 55

Gln Leu Val Leu Thr Gln Ser Pro Ser Ala Ser Ala Ser Leu Gly Ala
1               5                   10                  15

Ser Val Lys Leu Thr Cys Thr Leu Ser Ser Gln His Ser Thr Tyr Thr
                20                  25                  30

Ile Glu Trp Tyr Gln Gln Pro Glu Lys Gly Pro Arg Tyr Val Met
            35                  40                  45

Asp Leu Lys Gln Asp Gly Ser His Ser Thr Gly Asp Gly Ile Pro Asp
        50                  55                  60

Arg Phe Ser Gly Ser Ser Ser Gly Ala Glu Arg Tyr Leu Thr Ile Ser
65                  70                  75                  80

Ser Leu Gln Ser Glu Asp Glu Ala Asp Tyr Ile Cys Gly Val Gly Asp
                85                  90                  95

```
Thr Ile Lys Glu Gln Phe Val Tyr Val Phe Gly Gly Thr Lys Leu
            100                 105                 110
Thr Val Leu Gly Gln Pro
            115

<210> SEQ ID NO 56
<211> LENGTH: 118
<212> TYPE: PRT
<213> ORGANISM: Homo sapiens

<400> SEQUENCE: 56

Gln Val Gln Leu Val Glu Ser Gly Gly Gly Val Val Gln Pro Gly Arg
  1               5                  10                  15

Ser Leu Arg Leu Ser Cys Ala Ala Ser Gly Phe Thr Phe Ser Ser Tyr
            20                  25                  30

Gly Met Ser Trp Val Arg Gln Ala Pro Gly Lys Gly Leu Glu Trp Val
        35                  40                  45

Ala Thr Ile Ser Ser Gly Gly Ser Tyr Thr Tyr Tyr Pro Asp Ser Val
    50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Arg Gln Thr Thr Met Thr Tyr Phe Ala Tyr Trp Gly Gln Gly Thr
            100                 105                 110

Leu Val Thr Val Ser Ser
            115

<210> SEQ ID NO 57
<211> LENGTH: 411
<212> TYPE: DNA
<213> ORGANISM: Mus musculus
<220> FEATURE:
<221> NAME/KEY: CDS
<222> LOCATION: (1)..(411)
<220> FEATURE:
<221> NAME/KEY: mat_peptide
<222> LOCATION: (58)..(411)

<400> SEQUENCE: 57 atg aac ttc ggg ctc agc ttg att ttc ctt gcc ctc att tta aaa ggt       48
Met Asn Phe Gly Leu Ser Leu Ile Phe Leu Ala Leu Ile Leu Lys Gly
        -15                 -10                  -5 gtc cag tgt gag gtg caa ctg gtg gag tct ggg gga gac tta gtg aag       96
Val Gln Cys Glu Val Gln Leu Val Glu Ser Gly Gly Asp Leu Val Lys
         -1   1               5                  10 cct gga ggg tcc ctg aaa ctc tcc tgt gca gcc tct gga ttc act ttc      144
Pro Gly Gly Ser Leu Lys Leu Ser Cys Ala Ala Ser Gly Phe Thr Phe
         15                  20                  25 agt agc tat ggc atg tct tgg att cgc cag act cca gac aag agg ctg      192
Ser Ser Tyr Gly Met Ser Trp Ile Arg Gln Thr Pro Asp Lys Arg Leu
     30                  35                  40                  45 gag tgg gtc gca acc att agt agt ggt ggt agt tac acc tac tat cca      240
Glu Trp Val Ala Thr Ile Ser Ser Gly Gly Ser Tyr Thr Tyr Tyr Pro
                 50                  55                  60 gac agt gtg aag ggg cga ttc acc atc tcc aga gac aat gcc aag aac      288
Asp Ser Val Lys Gly Arg Phe Thr Ile Ser Arg Asp Asn Ala Lys Asn
             65                  70                  75 acc cta tac ctg caa atg agc agt ctg aag tct gag gac aca gcc atg      336
Thr Leu Tyr Leu Gln Met Ser Ser Leu Lys Ser Glu Asp Thr Ala Met
```

-continued

```
                      80                  85                  90
ttt tac tgt gca aga cag act act atg act tac ttt gct tac tgg ggc    384
Phe Tyr Cys Ala Arg Gln Thr Thr Met Thr Tyr Phe Ala Tyr Trp Gly
 95                 100                 105 caa ggg act ctg gtc act gtc tct gca                                411
Gln Gly Thr Leu Val Thr Val Ser Ala
110                 115

<210> SEQ ID NO 58
<211> LENGTH: 411
<212> TYPE: DNA
<213> ORGANISM: Homo sapiens
<220> FEATURE:
<221> NAME/KEY: CDS
<222> LOCATION: (1)..(411)
<220> FEATURE:
<221> NAME/KEY: mat_peptide
<222> LOCATION: (58)..(411)

<400> SEQUENCE: 58 atg ggg ttt ggg ctg agc tgg gtt ttc ctc gtt gct ctt tta aga ggt    48
Met Gly Phe Gly Leu Ser Trp Val Phe Leu Val Ala Leu Leu Arg Gly
            -15                 -10                  -5 gtc cag tgt cag gtg cag ctg gtg gag tct ggg gga ggc gtg gtc cag    96
Val Gln Cys Gln Val Gln Leu Val Glu Ser Gly Gly Gly Val Val Gln
 -1   1               5                  10 cct ggg agg tcc ctg aga ctc tcc tgt gca gcc tct gga ttc acc ttc    144
Pro Gly Arg Ser Leu Arg Leu Ser Cys Ala Ala Ser Gly Phe Thr Phe
         15                  20                  25 agt agc tat ggc atg tct tgg gtc cgc cag gct cca ggc aag ggg ctg    192
Ser Ser Tyr Gly Met Ser Trp Val Arg Gln Ala Pro Gly Lys Gly Leu
 30                  35                  40                  45 gag tgg gtg gca acc att agt agt ggt ggt agt tac acc tac tat cca    240
Glu Trp Val Ala Thr Ile Ser Ser Gly Gly Ser Tyr Thr Tyr Tyr Pro
                 50                  55                  60 gac agt gtg aag ggg cga ttc acc atc tcc aga gac aat tcc aag aac    288
Asp Ser Val Lys Gly Arg Phe Thr Ile Ser Arg Asp Asn Ser Lys Asn
             65                  70                  75 acg ctg tat ctg caa atg aac agc ctg aga gct gag gac acg gct gtg    336
Thr Leu Tyr Leu Gln Met Asn Ser Leu Arg Ala Glu Asp Thr Ala Val
         80                  85                  90 tat tac tgt gcg aga cag act act atg act tac ttt gct tac tgg ggc    384
Tyr Tyr Cys Ala Arg Gln Thr Thr Met Thr Tyr Phe Ala Tyr Trp Gly
 95                 100                 105 cag gga acc ctg gtc acc gtc tcc tca                                411
Gln Gly Thr Leu Val Thr Val Ser Ser
110                 115

<210> SEQ ID NO 59
<211> LENGTH: 11
<212> TYPE: PRT
<213> ORGANISM: Homo sapiens

<400> SEQUENCE: 59

Lys Ala Ser Gln Asp Val Asn Thr Ala Val Ala
 1               5                  10

<210> SEQ ID NO 60
<211> LENGTH: 7
<212> TYPE: PRT
<213> ORGANISM: Homo sapiens

<400> SEQUENCE: 60
```

```
Ser Ala Ser Asn Arg Tyr Thr
 1               5

<210> SEQ ID NO 61
<211> LENGTH: 9
<212> TYPE: PRT
<213> ORGANISM: Homo sapiens

<400> SEQUENCE: 61

Gln Gln His Tyr Ser Thr Pro Phe Thr
 1               5

<210> SEQ ID NO 62
<211> LENGTH: 5
<212> TYPE: PRT
<213> ORGANISM: Homo sapiens

<400> SEQUENCE: 62

Pro Tyr Trp Met Gln
 1               5

<210> SEQ ID NO 63
<211> LENGTH: 16
<212> TYPE: PRT
<213> ORGANISM: Homo sapiens

<400> SEQUENCE: 63

Ser Ile Phe Gly Asp Gly Asp Thr Arg Tyr Ser Gln Lys Phe Lys Gly
 1               5                  10                  15

<210> SEQ ID NO 64
<211> LENGTH: 11
<212> TYPE: PRT
<213> ORGANISM: Homo sapiens

<400> SEQUENCE: 64

Gly Leu Arg Arg Gly Gly Tyr Tyr Phe Asp Tyr
 1               5                  10

<210> SEQ ID NO 65
<211> LENGTH: 411
<212> TYPE: DNA
<213> ORGANISM: Mus musculus
<220> FEATURE:
<221> NAME/KEY: CDS
<222> LOCATION: (1)..(411)
<220> FEATURE:
<221> NAME/KEY: mat_peptide
<222> LOCATION: (58)..(411)

<400> SEQUENCE: 65 atg gcc tgg act cct ctc ttc ttc ttc ttt gtt ctt cat tgc tca ggt       48
Met Ala Trp Thr Pro Leu Phe Phe Phe Phe Val Leu His Cys Ser Gly
            -15                 -10                 -5 tct ttc tcc caa ctt gtg ctc act cag tca tct tca gcc tct ttc tcc       96
Ser Phe Ser Gln Leu Val Leu Thr Gln Ser Ser Ser Ala Ser Phe Ser
     -1  1               5                  10 ctg gga gcc tca gca aaa ctc acg tgc acc ttg agt agt cag cac agt      144
Leu Gly Ala Ser Ala Lys Leu Thr Cys Thr Leu Ser Ser Gln His Ser
     15                  20                  25 acg tac acc att gaa tgg tat cag caa cag cca ctc aag cct cct aag      192
Thr Tyr Thr Ile Glu Trp Tyr Gln Gln Gln Pro Leu Lys Pro Pro Lys
 30                  35                  40                  45 tat gtg atg gat ctt aag caa gat gga agc cac agc aca ggt gat ggg      240
Tyr Val Met Asp Leu Lys Gln Asp Gly Ser His Ser Thr Gly Asp Gly
```

```
att cct gat cgc ttc tct gga tcc agc tct ggt gct gat cgc tac ctt     288
Ile Pro Asp Arg Phe Ser Gly Ser Ser Ser Gly Ala Asp Arg Tyr Leu
            65                  70                  75 agc att tcc aac atc cag cca gaa gat gaa gca atg tac atc tgt ggt     336
Ser Ile Ser Asn Ile Gln Pro Glu Asp Glu Ala Met Tyr Ile Cys Gly
        80                  85                  90 gtg ggt gat aca att aag gaa caa ttt gtg tat gtt ttc ggc ggt ggg     384
Val Gly Asp Thr Ile Lys Glu Gln Phe Val Tyr Val Phe Gly Gly Gly
    95                  100                 105 acc aag gtc act gtc cta ggt cag ccc                                 411
Thr Lys Val Thr Val Leu Gly Gln Pro
110                 115

<210> SEQ ID NO 66
<211> LENGTH: 411
<212> TYPE: DNA
<213> ORGANISM: Homo sapiens
<220> FEATURE:
<221> NAME/KEY: CDS
<222> LOCATION: (1)..(411)
<220> FEATURE:
<221> NAME/KEY: mat_peptide
<222> LOCATION: (58)..(411)

<400> SEQUENCE: 66 atg gcc tgg act cct ctc ttc ttc ttc ttt gtt ctt cat tgc tca ggt     48
Met Ala Trp Thr Pro Leu Phe Phe Phe Phe Val Leu His Cys Ser Gly
                -15                 -10                 -5 tct ttc tcc cag ctt gtg ctg act caa tcg ccc tct gcc tct gcc tcc     96
Ser Phe Ser Gln Leu Val Leu Thr Gln Ser Pro Ser Ala Ser Ala Ser
        -1  1                   5                   10 ctg gga gcc tcg gtc aag ctc acc tgc acc ttg agt agt cag cac agt     144
Leu Gly Ala Ser Val Lys Leu Thr Cys Thr Leu Ser Ser Gln His Ser
    15                  20                  25 acg tac acc att gaa tgg cat cag cag cag cca gag aag ggc cct cgg     192
Thr Tyr Thr Ile Glu Trp His Gln Gln Gln Pro Glu Lys Gly Pro Arg
30                  35                  40                  45 tac ttg atg aaa ctt aag caa gat gga agc cac agc aca ggt gat ggg     240
Tyr Leu Met Lys Leu Lys Gln Asp Gly Ser His Ser Thr Gly Asp Gly
            50                  55                  60 att cct gat cgc ttc tca ggc tcc agc tct ggg gct gag cgc tac ctc     288
Ile Pro Asp Arg Phe Ser Gly Ser Ser Ser Gly Ala Glu Arg Tyr Leu
            65                  70                  75 acc atc tcc agc ctc cag tct gag gat gag gct gac tat tac tgt ggt     336
Thr Ile Ser Ser Leu Gln Ser Glu Asp Glu Ala Asp Tyr Tyr Cys Gly
        80                  85                  90 gtg ggt gat aca att aag gaa caa ttt gtg tac gtg ttc ggc gga ggg     384
Val Gly Asp Thr Ile Lys Glu Gln Phe Val Tyr Val Phe Gly Gly Gly
    95                  100                 105 acc aaa ctg acc gtc cta ggt cag ccc                                 411
Thr Lys Leu Thr Val Leu Gly Gln Pro
110                 115

<210> SEQ ID NO 67
<211> LENGTH: 411
<212> TYPE: DNA
<213> ORGANISM: Homo sapiens
<220> FEATURE:
<221> NAME/KEY: CDS
<222> LOCATION: (1)..(411)
<220> FEATURE:
<221> NAME/KEY: mat_peptide
<222> LOCATION: (58)..(411)
```

<400> SEQUENCE: 67

```
atg gcc tgg act cct ctc ttc ttc ttc ttt gtt ctt cat tgc tca ggt      48
Met Ala Trp Thr Pro Leu Phe Phe Phe Val Leu His Cys Ser Gly
                -15             -10                 -5 tct ttc tcc cag ctt gtg ctg act caa tcg ccc tct gcc tct gcc tcc      96
Ser Phe Ser Gln Leu Val Leu Thr Gln Ser Pro Ser Ala Ser Ala Ser
         -1   1               5                   10 ctg gga gcc tcg gtc aag ctc acc tgc acc ttg agt agt cag cac agt     144
Leu Gly Ala Ser Val Lys Leu Thr Cys Thr Leu Ser Ser Gln His Ser
         15                  20                  25 acg tac acc att gaa tgg tat cag cag cag cca gag aag ggc cct aag     192
Thr Tyr Thr Ile Glu Trp Tyr Gln Gln Gln Pro Glu Lys Gly Pro Lys
     30                  35                  40                 45 tac ctg atg gat ctt aag caa gat gga agc cac agc aca ggt gat ggg     240
Tyr Leu Met Asp Leu Lys Gln Asp Gly Ser His Ser Thr Gly Asp Gly
             50                  55                  60 att cct gat cgc ttc tca ggc tcc agc tct ggg gct gag cgc tac ctc     288
Ile Pro Asp Arg Phe Ser Gly Ser Ser Ser Gly Ala Glu Arg Tyr Leu
                 65                  70                  75 acc atc tcc agc ctc cag tct gag gat gag gct gac tat tac tgt ggt     336
Thr Ile Ser Ser Leu Gln Ser Glu Asp Glu Ala Asp Tyr Tyr Cys Gly
             80                  85                  90 gtg ggt gat aca att aag gaa caa ttt gtg tac gtg ttc ggc gga ggg     384
Val Gly Asp Thr Ile Lys Glu Gln Phe Val Tyr Val Phe Gly Gly Gly
         95                  100                 105 acc aaa ctg acc gtc cta ggc cag ccc                                 411
Thr Lys Leu Thr Val Leu Gly Gln Pro
110                 115
```

<210> SEQ ID NO 68
<211> LENGTH: 411
<212> TYPE: DNA
<213> ORGANISM: Homo sapiens
<220> FEATURE:
<221> NAME/KEY: CDS
<222> LOCATION: (1)..(411)
<220> FEATURE:
<221> NAME/KEY: mat_peptide
<222> LOCATION: (58)..(411)

<400> SEQUENCE: 68

```
atg gcc tgg act cct ctc ttc ttc ttc ttt gtt ctt cat tgc tca ggt      48
Met Ala Trp Thr Pro Leu Phe Phe Phe Val Leu His Cys Ser Gly
                -15             -10                 -5 tct ttc tcc cag ctt gtg ctg act caa tcg ccc tct gcc tct gcc tcc      96
Ser Phe Ser Gln Leu Val Leu Thr Gln Ser Pro Ser Ala Ser Ala Ser
         -1   1               5                   10 ctg gga gcc tcg gtc aag ctc acc tgc acc ttg agt agt cag cac agt     144
Leu Gly Ala Ser Val Lys Leu Thr Cys Thr Leu Ser Ser Gln His Ser
         15                  20                  25 acg tac acc att gaa tgg tat cag cag cag cca gag aag ggc cct aag     192
Thr Tyr Thr Ile Glu Trp Tyr Gln Gln Gln Pro Glu Lys Gly Pro Lys
     30                  35                  40                 45 tac gtg atg gat ctt aag caa gat gga agc cac agc aca ggt gat ggg     240
Tyr Val Met Asp Leu Lys Gln Asp Gly Ser His Ser Thr Gly Asp Gly
             50                  55                  60 att cct gat cgc ttc tca ggc tcc agc tct ggg gct gag cgc tac ctc     288
Ile Pro Asp Arg Phe Ser Gly Ser Ser Ser Gly Ala Glu Arg Tyr Leu
                 65                  70                  75 acc atc tcc agc ctc cag tct gag gat gag gct gac tat tac tgt ggt     336
Thr Ile Ser Ser Leu Gln Ser Glu Asp Glu Ala Asp Tyr Tyr Cys Gly
```

|  |  |  |  |  |  |  |  |  | 80 |  |  |  |  | 85 |  |  |  |  | 90 |  |  |  |
|---|---|---|---|---|---|---|---|---|---|---|---|---|---|---|---|---|---|---|---|---|---|---|

```
gtg ggt gat aca att aag gaa caa ttt gtg tac gtg ttc ggc gga ggg      384
Val Gly Asp Thr Ile Lys Glu Gln Phe Val Tyr Val Phe Gly Gly Gly
         95                 100                 105 acc aaa ctg acc gtc cta ggc cag ccc                                  411
Thr Lys Leu Thr Val Leu Gly Gln Pro
110             115

<210> SEQ ID NO 69
<211> LENGTH: 411
<212> TYPE: DNA
<213> ORGANISM: Homo sapiens
<220> FEATURE:
<221> NAME/KEY: CDS
<222> LOCATION: (1)..(411)
<220> FEATURE:
<221> NAME/KEY: mat_peptide
<222> LOCATION: (58)..(411)

<400> SEQUENCE: 69 atg gcc tgg act cct ctc ttc ttc ttc ttt gtt ctt cat tgc tca ggt      48
Met Ala Trp Thr Pro Leu Phe Phe Phe Phe Val Leu His Cys Ser Gly
                -15                 -10                 -5 tct ttc tcc cag ctt gtg ctg act caa tcg ccc tct gcc tct gcc tcc      96
Ser Phe Ser Gln Leu Val Leu Thr Gln Ser Pro Ser Ala Ser Ala Ser
         -1  1               5                  10 ctg gga gcc tcg gtc aag ctc acc tgc acc ttg agt agt cag cac agt     144
Leu Gly Ala Ser Val Lys Leu Thr Cys Thr Leu Ser Ser Gln His Ser
         15                  20                  25 acg tac acc att gaa tgg tat cag cag cag cca gag aag ggc cct agg     192
Thr Tyr Thr Ile Glu Trp Tyr Gln Gln Gln Pro Glu Lys Gly Pro Arg
 30                  35                  40                  45 tac ctg atg gat ctt aag caa gat gga agc cac agc aca ggt gat ggg     240
Tyr Leu Met Asp Leu Lys Gln Asp Gly Ser His Ser Thr Gly Asp Gly
                 50                  55                  60 att cct gat cgc ttc tca ggc tcc agc tct ggg gct gag cgc tac ctc     288
Ile Pro Asp Arg Phe Ser Gly Ser Ser Ser Gly Ala Glu Arg Tyr Leu
                 65                  70                  75 acc atc tcc agc ctc cag tct gag gat gag gct gac tat tac tgt ggt     336
Thr Ile Ser Ser Leu Gln Ser Glu Asp Glu Ala Asp Tyr Tyr Cys Gly
         80                  85                  90 gtg ggt gat aca att aag gaa caa ttt gtg tac gtg ttc ggc gga ggg     384
Val Gly Asp Thr Ile Lys Glu Gln Phe Val Tyr Val Phe Gly Gly Gly
         95                 100                 105 acc aaa ctg acc gtc cta ggc cag ccc                                  411
Thr Lys Leu Thr Val Leu Gly Gln Pro
110             115

<210> SEQ ID NO 70
<211> LENGTH: 411
<212> TYPE: DNA
<213> ORGANISM: Homo sapiens
<220> FEATURE:
<221> NAME/KEY: CDS
<222> LOCATION: (1)..(411)
<220> FEATURE:
<221> NAME/KEY: mat_peptide
<222> LOCATION: (58)..(411)

<400> SEQUENCE: 70 atg gcc tgg act cct ctc ttc ttc ttc ttt gtt ctt cat tgc tca ggt      48
Met Ala Trp Thr Pro Leu Phe Phe Phe Phe Val Leu His Cys Ser Gly
                -15                 -10                 -5 tct ttc tcc cag ctt gtg ctg act caa tcg ccc tct gcc tct gcc tcc      96
```

```
                    Ser Phe Ser Gln Leu Val Leu Thr Gln Ser Pro Ser Ala Ser Ala Ser
                        -1   1               5                      10 ctg gga gcc tcg gtc aag ctc acc tgc acc ttg agt agt cag cac agt       144
Leu Gly Ala Ser Val Lys Leu Thr Cys Thr Leu Ser Ser Gln His Ser
         15                  20                  25 acg tac acc att gaa tgg tat cag cag cag cca gag aag ggc cct agg       192
Thr Tyr Thr Ile Glu Trp Tyr Gln Gln Gln Pro Glu Lys Gly Pro Arg
 30                  35                  40                  45 tac gtg atg gat ctt aag caa gat gga agc cac agc aca ggt gat ggg       240
Tyr Val Met Asp Leu Lys Gln Asp Gly Ser His Ser Thr Gly Asp Gly
                 50                  55                  60 att cct gat cgc ttc tca ggc tcc agc tct ggg gct gag cgc tac ctc       288
Ile Pro Asp Arg Phe Ser Gly Ser Ser Ser Gly Ala Glu Arg Tyr Leu
             65                  70                  75 acc atc tcc agc ctc cag tct gag gat gag gct gac tat tac tgt ggt       336
Thr Ile Ser Ser Leu Gln Ser Glu Asp Glu Ala Asp Tyr Tyr Cys Gly
         80                  85                  90 gtg ggt gat aca att aag gaa caa ttt gtg tac gtg ttc ggc gga ggg       384
Val Gly Asp Thr Ile Lys Glu Gln Phe Val Tyr Val Phe Gly Gly Gly
     95                  100                 105 acc aaa ctg acc gtc cta ggc cag ccc                                   411
Thr Lys Leu Thr Val Leu Gly Gln Pro
110                 115

<210> SEQ ID NO 71
<211> LENGTH: 411
<212> TYPE: DNA
<213> ORGANISM: Homo sapiens
<220> FEATURE:
<221> NAME/KEY: CDS
<222> LOCATION: (1)..(411)
<220> FEATURE:
<221> NAME/KEY: mat_peptide
<222> LOCATION: (58)..(411)

<400> SEQUENCE: 71 atg gcc tgg act cct ctc ttc ttc ttc ttt gtt ctt cat tgc tca ggt        48
Met Ala Trp Thr Pro Leu Phe Phe Phe Phe Val Leu His Cys Ser Gly
                -15                 -10                  -5 tct ttc tcc cag ctt gtg ctg act caa tcg ccc tct gcc tct gcc tcc        96
Ser Phe Ser Gln Leu Val Leu Thr Gln Ser Pro Ser Ala Ser Ala Ser
     -1   1               5                      10 ctg gga gcc tcg gtc aag ctc acc tgc acc ttg agt agt cag cac agt       144
Leu Gly Ala Ser Val Lys Leu Thr Cys Thr Leu Ser Ser Gln His Ser
         15                  20                  25 acg tac acc att gaa tgg tat cag cag cag cca gag aag ggc cct aag       192
Thr Tyr Thr Ile Glu Trp Tyr Gln Gln Gln Pro Glu Lys Gly Pro Lys
 30                  35                  40                  45 tac ctg atg gat ctt aag caa gat gga agc cac agc aca ggt gat ggg       240
Tyr Leu Met Asp Leu Lys Gln Asp Gly Ser His Ser Thr Gly Asp Gly
                 50                  55                  60 att cct gat cgc ttc tca ggc tcc agc tct ggg gct gag cgc tac ctc       288
Ile Pro Asp Arg Phe Ser Gly Ser Ser Ser Gly Ala Glu Arg Tyr Leu
             65                  70                  75 acc atc tcc agc ctc cag tct gag gat gag gct gac tat atc tgt ggt       336
Thr Ile Ser Ser Leu Gln Ser Glu Asp Glu Ala Asp Tyr Ile Cys Gly
         80                  85                  90 gtg ggt gat aca att aag gaa caa ttt gtg tac gtg ttc ggc gga ggg       384
Val Gly Asp Thr Ile Lys Glu Gln Phe Val Tyr Val Phe Gly Gly Gly
     95                  100                 105 acc aaa ctg acc gtc cta ggc cag ccc                                   411
Thr Lys Leu Thr Val Leu Gly Gln Pro
```

<210> SEQ ID NO 72
<211> LENGTH: 411
<212> TYPE: DNA
<213> ORGANISM: Homo sapiens
<220> FEATURE:
<221> NAME/KEY: CDS
<222> LOCATION: (1)..(411)
<220> FEATURE:
<221> NAME/KEY: mat_peptide
<222> LOCATION: (58)..(411)

<400> SEQUENCE: 72

| atg gcc tgg act cct ctc ttc ttc ttt gtt ctt cat tgc tca ggt | 48 |
| Met Ala Trp Thr Pro Leu Phe Phe Phe Val Leu His Cys Ser Gly | |
|             -15                   -10                 -5 | |

| tct ttc tcc cag ctt gtg ctg act caa tcg ccc tct gcc tct gcc tcc | 96 |
| Ser Phe Ser Gln Leu Val Leu Thr Gln Ser Pro Ser Ala Ser Ala Ser | |
|     -1  1               5                       10 | |

| ctg gga gcc tcg gtc aag ctc acc tgc acc ttg agt agt cag cac agt | 144 |
| Leu Gly Ala Ser Val Lys Leu Thr Cys Thr Leu Ser Ser Gln His Ser | |
|      15                 20                25 | |

| acg tac acc att gaa tgg tat cag cag cag cca gag aag ggc cct agg | 192 |
| Thr Tyr Thr Ile Glu Trp Tyr Gln Gln Gln Pro Glu Lys Gly Pro Arg | |
| 30                35                   40                 45 | |

| tac ctg atg gat ctt aag caa gat gga agc cac agc aca ggt gat ggg | 240 |
| Tyr Leu Met Asp Leu Lys Gln Asp Gly Ser His Ser Thr Gly Asp Gly | |
|              50                 55                 60 | |

| att cct gat cgc ttc tca ggc tcc agc tct ggg gct gag cgc tac ctc | 288 |
| Ile Pro Asp Arg Phe Ser Gly Ser Ser Ser Gly Ala Glu Arg Tyr Leu | |
|           65                   70                75 | |

| acc atc tcc agc ctc cag tct gag gat gag gct gac tat atc tgt ggt | 336 |
| Thr Ile Ser Ser Leu Gln Ser Glu Asp Glu Ala Asp Tyr Ile Cys Gly | |
|               80                 85               90 | |

| gtg ggt gat aca att aag gaa caa ttt gtg tac gtg ttc ggc gga ggg | 384 |
| Val Gly Asp Thr Ile Lys Glu Gln Phe Val Tyr Val Phe Gly Gly Gly | |
|      95                 100                 105 | |

| acc aaa ctg acc gtc cta ggc cag ccc | 411 |
| Thr Lys Leu Thr Val Leu Gly Gln Pro | |
| 110                 115 | |

<210> SEQ ID NO 73
<211> LENGTH: 411
<212> TYPE: DNA
<213> ORGANISM: Homo sapiens
<220> FEATURE:
<221> NAME/KEY: CDS
<222> LOCATION: (1)..(411)
<220> FEATURE:
<221> NAME/KEY: mat_peptide
<222> LOCATION: (58)..(411)

<400> SEQUENCE: 73

| atg gcc tgg act cct ctc ttc ttc ttt gtt ctt cat tgc tca ggt | 48 |
| Met Ala Trp Thr Pro Leu Phe Phe Phe Val Leu His Cys Ser Gly | |
|             -15                   -10                 -5 | |

| tct ttc tcc cag ctt gtg ctg act caa tcg ccc tct gcc tct gcc tcc | 96 |
| Ser Phe Ser Gln Leu Val Leu Thr Gln Ser Pro Ser Ala Ser Ala Ser | |
|     -1  1               5                       10 | |

| ctg gga gcc tcg gtc aag ctc acc tgc acc ttg agt agt cag cac agt | 144 |
| Leu Gly Ala Ser Val Lys Leu Thr Cys Thr Leu Ser Ser Gln His Ser | |
|      15                 20                25 | |

| acg tac acc att gaa tgg tat cag cag cag cca gag aag ggc cct aag | 192 |

```
Thr Tyr Thr Ile Glu Trp Tyr Gln Gln Gln Pro Glu Lys Gly Pro Lys
        30                  35                  40                  45 tac gtg atg gat ctt aag caa gat gga agc cac agc aca ggt gat ggg        240
Tyr Val Met Asp Leu Lys Gln Asp Gly Ser His Ser Thr Gly Asp Gly
                50                  55                  60 att cct gat cgc ttc tca ggc tcc agc tct ggg gct gag cgc tac ctc        288
Ile Pro Asp Arg Phe Ser Gly Ser Ser Ser Gly Ala Glu Arg Tyr Leu
            65                  70                  75 acc atc tcc agc ctc cag tct gag gat gag gct gac tat atc tgt ggt        336
Thr Ile Ser Ser Leu Gln Ser Glu Asp Glu Ala Asp Tyr Ile Cys Gly
        80                  85                  90 gtg ggt gat aca att aag gaa caa ttt gtg tac gtg ttc ggc gga ggg        384
Val Gly Asp Thr Ile Lys Glu Gln Phe Val Tyr Val Phe Gly Gly Gly
    95                  100                 105 acc aaa ctg acc gtc cta ggc cag ccc                                    411
Thr Lys Leu Thr Val Leu Gly Gln Pro
110                 115

<210> SEQ ID NO 74
<211> LENGTH: 411
<212> TYPE: DNA
<213> ORGANISM: Homo sapiens
<220> FEATURE:
<221> NAME/KEY: CDS
<222> LOCATION: (1)..(411)
<220> FEATURE:
<221> NAME/KEY: mat_peptide
<222> LOCATION: (58)..(411)

<400> SEQUENCE: 74 atg gcc tgg act cct ctc ttc ttc ttc ttt gtt ctt cat tgc tca ggt         48
Met Ala Trp Thr Pro Leu Phe Phe Phe Phe Val Leu His Cys Ser Gly
                -15                 -10                 -5 tct ttc tcc cag ctt gtg ctg act caa tcg ccc tct gcc tct gcc tcc         96
Ser Phe Ser Gln Leu Val Leu Thr Gln Ser Pro Ser Ala Ser Ala Ser
            -1  1                   5                   10 ctg gga gcc tcg gtc aag ctc acc tgc acc ttg agt agt cag cac agt        144
Leu Gly Ala Ser Val Lys Leu Thr Cys Thr Leu Ser Ser Gln His Ser
    15                  20                  25 acg tac acc att gaa tgg tat cag cag cag cca gag aag ggc cct agg        192
Thr Tyr Thr Ile Glu Trp Tyr Gln Gln Gln Pro Glu Lys Gly Pro Arg
        30                  35                  40                  45 tac gtg atg gat ctt aag caa gat gga agc cac agc aca ggt gat ggg        240
Tyr Val Met Asp Leu Lys Gln Asp Gly Ser His Ser Thr Gly Asp Gly
                50                  55                  60 att cct gat cgc ttc tca ggc tcc agc tct ggg gct gag cgc tac ctc        288
Ile Pro Asp Arg Phe Ser Gly Ser Ser Ser Gly Ala Glu Arg Tyr Leu
            65                  70                  75 acc atc tcc agc ctc cag tct gag gat gag gct gac tat atc tgt ggt        336
Thr Ile Ser Ser Leu Gln Ser Glu Asp Glu Ala Asp Tyr Ile Cys Gly
        80                  85                  90 gtg ggt gat aca att aag gaa caa ttt gtg tac gtg ttc ggc gga ggg        384
Val Gly Asp Thr Ile Lys Glu Gln Phe Val Tyr Val Phe Gly Gly Gly
    95                  100                 105 acc aaa ctg acc gtc cta ggc cag ccc                                    411
Thr Lys Leu Thr Val Leu Gly Gln Pro
110                 115

<210> SEQ ID NO 75
<211> LENGTH: 34
<212> TYPE: PRT
<213> ORGANISM: Homo sapiens
```

```
<400> SEQUENCE: 75

Ala Val Ser Glu His Gln Leu Leu His Asp Lys Gly Lys Ser Ile Gln
 1               5                  10                  15

Asp Leu Arg Arg Arg Phe Phe Leu His His Leu Ile Ala Glu Ile His
            20                  25                  30

Thr Ala

<210> SEQ ID NO 76
<211> LENGTH: 20
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 76
cagatgcacc tgacgccctt                                            20

<210> SEQ ID NO 77
<211> LENGTH: 21
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 77
cccagccgtg gttatcctgg a                                          21

<210> SEQ ID NO 78
<211> LENGTH: 20
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 78
gtccaccaag aagctgagcg                                            20

<210> SEQ ID NO 79
<211> LENGTH: 20
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 79
ttggtgcaca gggccttgag                                            20

<210> SEQ ID NO 80
<211> LENGTH: 21
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 80
caggaaaacc aggtctcgat g                                          21

<210> SEQ ID NO 81
<211> LENGTH: 21
<212> TYPE: DNA
```

```
<213> ORGANISM: Artificial Sequence
<220> FEATURE:
<223> OTHER INFORMATION: Description of Artificial Sequence:Synthetic
      DNA

<400> SEQUENCE: 81
ttgaggccct tagttgctat g                                              21

<210> SEQ ID NO 82
<211> LENGTH: 30
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 82
agagtgctgc cccatctgcc caactgacct                                     30

<210> SEQ ID NO 83
<211> LENGTH: 30
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 83
cattactccc aactgggcgc caccagcctt                                     30

<210> SEQ ID NO 84
<211> LENGTH: 22
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 84
cggactcgtc atactcctgc tt                                             22

<210> SEQ ID NO 85
<211> LENGTH: 21
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 85
cactcttcca gccttccttc c                                              21
```